(12) United States Patent
Cui et al.

(10) Patent No.: US 12,310,968 B2
(45) Date of Patent: *May 27, 2025

(54) CHIRAL DIARYL MACROCYCLES AND USES THEREOF

(71) Applicant: TURNING POINT THERAPEUTICS, INC., Princeton, NJ (US)

(72) Inventors: Jingrong J. Cui, Princeton, NJ (US); Yishan Li, Princeton, NJ (US); Evan W. Rogers, Princeton, NJ (US); Dayong Zhai, Princeton, NJ (US); Wei Deng, Princeton, NJ (US); Zhongdong Huang, Princeton, NJ (US)

(73) Assignee: Turning Point Therapeutics, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/819,858

(22) Filed: Aug. 15, 2022

(65) Prior Publication Data

US 2023/0346786 A1 Nov. 2, 2023

Related U.S. Application Data

(63) Continuation of application No. 16/998,763, filed on Aug. 20, 2020, now Pat. No. 11,452,725, which is a continuation of application No. 15/745,915, filed as application No. PCT/US2016/043132 on Jul. 20, 2016, now abandoned.

(Continued)

(51) Int. Cl.
*A61K 31/519* (2006.01)
*A61P 35/00* (2006.01)

(52) U.S. Cl.
CPC ............ *A61K 31/519* (2013.01); *A61P 35/00* (2018.01)

(58) Field of Classification Search
CPC .... A61K 31/519; A61K 31/52; A61K 31/395; A61P 35/00; C07D 491/12
See application file for complete search history.

(56) References Cited

U.S. PATENT DOCUMENTS 5,639,778 A 6/1997 Andersson et al.
8,497,270 B2 7/2013 Thuring et al.
(Continued)

FOREIGN PATENT DOCUMENTS

CL 2012003227 A1 2/2013
CN 102143750 A 8/2011
(Continued)

OTHER PUBLICATIONS

Ravi et al. (2011) "Treatment of Tenosynovial Giant Cell Tumor and Pigmented Villonodular Synovitis", Current Opinion in Oncology, 23(4):361-366.

(Continued)

*Primary Examiner* — San Ming R Hui
(74) *Attorney, Agent, or Firm* — Mintz, Levin, Cohn, Ferris, Glovsky and Popeo, P.C.

(57) ABSTRACT

This disclosure relates to the use of certain diaryl macrocycle compounds, specifically (7S13R)-11-fluoro-7,13-dimethyl-6,7,13,14-tetrahydro-1,15-ethenopyrazolo[4,3-f][1,4,8,10]benzoxatriazacyclotridecin-4(5H)-one in the treatment of disease in mammals. This disclosure also relates to compositions including such compounds, and to methods of using such compositions in the treatment of diseases in mammals, especially in humans.

27 Claims, 14 Drawing Sheets

Related U.S. Application Data

(60) Provisional application No. 62/302,231, filed on Mar. 2, 2016, provisional application No. 62/195,081, filed on Jul. 21, 2015.

(56) References Cited

U.S. PATENT DOCUMENTS

| | | |
|---|---|---|
| 8,680,111 B2 | 3/2014 | Bailey et al. |
| 8,791,123 B2 | 7/2014 | Allen et al. |
| 8,815,872 B2 | 8/2014 | Yu et al. |
| 8,933,084 B2 | 1/2015 | Andrews et al. |
| 8,969,565 B2 | 3/2015 | Bi et al. |
| 9,238,604 B2 | 1/2016 | Xu et al. |
| 9,714,258 B2 | 7/2017 | Cui et al. |
| 10,246,466 B2 | 4/2019 | Cui et al. |
| 10,294,242 B2 | 5/2019 | Cui et al. |
| 10,316,044 B2 | 6/2019 | Cui et al. |
| 11,452,725 B2 | 9/2022 | Cui et al. |
| 2011/0294801 A1 | 12/2011 | Yu et al. |
| 2013/0143895 A1 | 6/2013 | McAllister et al. |
| 2013/0203776 A1 | 8/2013 | Andrews et al. |
| 2013/0245021 A1 | 9/2013 | Bi et al. |
| 2013/0252961 A1 | 9/2013 | Bailey et al. |
| 2014/0107099 A1 | 4/2014 | Blaney et al. |
| 2014/0206605 A1 | 7/2014 | Beutner et al. |
| 2016/0339027 A1 | 11/2016 | Carter et al. |
| 2017/0002023 A1 | 1/2017 | Cui et al. |
| 2017/0334929 A1 | 11/2017 | Cui et al. |
| 2018/0186813 A1 | 7/2018 | Cui et al. |
| 2018/0194777 A1 | 7/2018 | Cui et al. |
| 2018/0325901 A1 | 11/2018 | Cui et al. |
| 2021/0030756 A1 | 2/2021 | Cui et al. |

FOREIGN PATENT DOCUMENTS

| | | |
|---|---|---|
| CN | 102971322 A | 3/2013 |
| JP | 2012502043 A | 1/2012 |
| WO | 2009024332 A1 | 2/2009 |
| WO | 2010028116 A1 | 3/2010 |
| WO | 2010033941 A1 | 3/2010 |
| WO | 2010048314 A1 | 4/2010 |
| WO | 2010051549 A1 | 5/2010 |
| WO | 2011006074 A1 | 1/2011 |
| WO | 2011146336 A1 | 11/2011 |
| WO | 2012/34091 A1 | 3/2012 |
| WO | 2012136859 A1 | 10/2012 |
| WO | 2013001310 A1 | 1/2013 |
| WO | 2013028465 A1 | 2/2013 |
| WO | 2013045653 A1 | 4/2013 |
| WO | 2013132376 A1 | 9/2013 |
| WO | 2013134219 A1 | 9/2013 |
| WO | 2013134228 A1 | 9/2013 |
| WO | 2013147711 A1 | 10/2013 |
| WO | 2015112806 A2 | 7/2015 |
| WO | 2017004342 A1 | 1/2017 |
| WO | 2017007759 A1 | 1/2017 |
| WO | 2017015367 A1 | 1/2017 |
| WO | 2018022911 A1 | 2/2018 |
| WO | 2018140554 A1 | 8/2018 |
| WO | 2019023417 A1 | 1/2019 |

OTHER PUBLICATIONS

Reiter et al. (Apr. 1, 2005) "The t(8;9)(p. 22;p. 24) Is a Recurrent Abnormality in Chronic and Acute Leukemia that Fuses PCM1 to JAK2", Cancer Research, 65(7):2662-2667.
Ries et al. (2014) "Targeting Tumor-associated Macrophages with Anti-CSF-1R Antibody Reveals a Strategy for Cancer Therapy", Cancer Cell, 25(6):846-859.
Rudd et al. (2014) "Mutational Analysis of the Tyrosine Kinome in Serous and Clear Cell Endometrial Cancer Uncovers Rare Somatic Mutations in TNK2 and DDR1", BMC Cancer Article No. 884, 14:9 pages.
Sancier et al. (Feb. 24, 2011) "Specific Oncogenic Activity of the Src-Family Tyrosine Kinase c-Yes in Colon Carcinoma Cells", PLoS One, 6(2):e17237(10 pages).
Sawyers Charles (Nov. 18, 2004) "Targeted Cancer Therapy", Nature, 432(7015):294-297.
Schiller et al. (Jan. 10, 2002) "Comparison of Four Chemotherapy Regimens for Advanced Non-Small-Cell Lung Cancer", The New England Journal of Medicine, 346(2):92-98.
Schuchardt et al. (1994) "Defects in the Kidney and Enteric Nervous System of Mice Lacking the Tyrosine Kinase Receptor Ret", Nature, 367:380-383.
Schwarz et al. (2014) "LYN-activating Mutations Mediate Antiestrogen Resistance in Estrogen Receptor—positive Breast Cancer", The Journal of Clinical Investigation, 124(12):5490-5502.
Sen et al. (Feb. 2011) "Distinct Interactions Between c-Src and c-Met in Mediating Resistance to c-Src Inhibition in Head and Neck Cancer", Clinical Cancer Research, 17(3):514-524(28 Pages).
Verma et al. (Oct. 2011) "Targeting Axl and Mer Kinases in Cancer", Molecular Cancer Therapeutics, 10(10):1763-1773.
Vergani et al. (Dec. 2011) "Identification of MET and SRC Activation in Melanoma Cell Lines Showing Primary Resistance to PLX4032", Neoplasia, 13(12):1132-1142.
Vaishnavi et al. (2015) "TRKing Down an Old Oncogene in a New era of Targeted Therapy", Cancer Discovery, 5(1):25-34(19 Pages).
Shaw et al. (Nov. 20, 2014) "Crizotinib in ROS1-Rearranged Non-Small-Cell Lung Cancer", The New England Journal of Medicine, 371(21):1963-1971.
Shi et al. (2014) "MiR-204 Inhibits Human NSCLC Metastasis Through Suppression of NUAK1", British Journal of Cancer, 111(12):2316-2327.
Smolen et al. (2006) "Amplification of MET may Identify a Subset of Cancers with Extreme Sensitivity to the Selective Tyrosine Kinase Inhibitor PHA-665752", Proceedings of the National Academy of Sciences, 103(7):2316-2321.
Soda et al. (Aug. 2, 2007) "Identification of the Transforming EML4-ALK Fusion Gene in Non-small-cell Lung Cancer", Nature, 448(7153):561-566.
Sonbol et al. (2013) "Comprehensive Review of JAK Inhibitors in Myeloproliferative Neoplasms", Therapeutic Advances in Hematology, 4(1):15-35.
Song et al. (2014) "Cetuximab-Induced MET Activation Acts as a Novel Resistance Mechanism in Colon Cancer Cells", International Journal of Molecular Sciences, 15(4):5838-5851.
Stabile et al. (Jan. 2013) "c-Src Activation Mediates Erlotinib Resistance in Head and Neck Cancer by Stimulating c-Met", Clinical Cancer Research, 19(2):380-392(28 Pages).
Stransky et al. (2014) "The Landscape of Kinase Fusions in Cancer", Nature Communications Article No. 4846, 5:10 pages.
Straussman (2012) "Tumour Micro-environment Elicits Innate Resistance to RAF Inhibitors through HGF Secretion", Nature, 487(7408):500-504.
Summy et al. (2003) "Src Family Kinases in Tumor Progression and Metastasis", Cancer and Metastasis Reviews, 22(4):337-358.
Takahashi et al. (Sep. 1, 1985) "Activation of a Novel Human Transforming Gene, ret, by DNA Rearrangement", Cell, vol. 42(2):581-588.
Takeuchi et al. (Nov. 2012) "RET, ROS1 and ALK Fusions in Lung Cancer", Nature Medicine, 18(3):378-381.
Thiele et al. (Oct. 2009) "On Trk—The TrkB Signal Transduction Pathway is an Increasingly Important Target in Cancer Biology", Clinical Cancer Research, 15(19):5962-5967.
Tomasson et al. (2008) "Somatic Mutations and Germline Sequence Variants in the Expressed Tyrosine Kinase Genes of Patients with De Novo Acute Myeloid Leukemia", Blood, 111(9):4797-4808.
Toso et al. (Oct. 9, 2014) "Enhancing Chemotherapy Efficacy in Pten-deficient Prostate Tumors by Activating the Senescence-associated Antitumor Immunity", Cell Reports, 9(1):75-89.
Trusolino et al. (Dec. 2010) "MET Signalling: Principles and Functions in Development, Organ Regeneration and Cancer", Nature Reviews Molecular Cell Biology, 11(12):834-848.
Vainchenker et al. (Aug. 2008) "JAKs in Pathology: Role of Janus Kinases in Hematopoietic Malignancies and Immunodeficiencies", Seminars in Cell & Developmental Biology, 19(4):385-393.

(56) References Cited

OTHER PUBLICATIONS

Vaishnavi et al. (2013) "Oncogenic and Drug-Sensitive NTRK1 Rearrangements in Lung Cancer", Nature Medicine, 19(11):1469-1472.
Extended European Search Report issued in European Application No. 16828471.9, mailed on Mar. 26, 2019, 7 Pages.
Extended European Search Report issued in European Application No. 16818768.0, mailed on Jan. 30, 2019, 12 Pages.
Quintás-Cardama et al. (2010) "Preclinical Characterization of the Selective JAK1/2 Inhibitor INCB018424: Therapeutic Implications for the Treatment of Myeloproliferative Neoplasms", Blood, 115(15):3109-3117.
Quintás-Cardama et al. (Feb. 2011) "Janus Kinase Inhibitors for the Treatment of Myeloproliferative Neoplasias and Beyond", Nature Reviews Drug Discovery, 10(2):127-140.
Zou et al. (2007) "An Orally Available Small-Molecule Inhibitor of C-Met, PF-2341066, Exhibits Cytoreductive Antitumor Efficacy through Anti Proliferative and Antiangiogenic Mechanisms", Cancer Research, 67(9):4408-4417.
Zhang et al. (2012) "Targeting Src Family Kinases in Anti-Cancer Therapies: Turning Promise into Triumph", Trends in Pharmacological Sciences, 33(3):122-128.
Hammerman et al. (2011) "Mutations in the DDR2 Kinase Gene Identify a Novel Therapeutic Target in Squamous Cell Lung Cancer", Cancer Discovery, 1(1):78-89.
Harbinski et al. (2012) "Rescue Screens with Secreted Proteins Reveal Compensatory Potential of Receptor Tyrosine Kinases in Driving Cancer Growth", Cancer Discovery, 2(10):948-959.
Heynen et al. (Dec. 15, 2014) "Resistance to Targeted Cancer Drugs through Hepatocyte Growth Factor Signaling", Cell Cycle, 13(24):3808-3817.
James et al. (2005) "A Unique Clonal JAK2 Mutation Leading to Constitutive Signalling Causes Polycythaemia Vera", Nature, 434(7037):1144-1148.
Wilson et al. (Dec. 1, 2012) "Widespread Potential for Growth-Factor-Driven Resistance to Anticancer Kinase Inhibitors", Nature, 487(7408):505-509.
Johnson et al. (Jun. 12, 2014) "Discovery of (10R)-7-Amino-12-fluoro-2,10, 16-Irimethyl-15—0xo-10, 15, 16, 17-tetrahydro-2H-8,4-6 methane )pyrazolo[4,3-h][2,5, 11 ]-benzoxadiazacycloletradecine-3-carbonilrile (PF-06463922), a Macrocyclic Inhibitor Jf Anaplastic Lymphoma Kinase (ALK) an", Journal of Medicinal Chemistry, 57(11):4720-4744.
Jordan Craig V. (Mar. 2003) "Tamoxifen: A Most Unlikely Pioneering Medicine", Nature Reviews Drug Discovery, 2(3):205-213.
Katayama et al. (Feb. 2012) "Mechanisms of Acquired Crizotinib Resistance in ALK-rearranged Lung Cancers", Science Translational Medicine, 4(120):25 Pages.
Kentsis et al. (2012) "Autocrine Activation of the MET Receptor Tyrosine Kinase in Acute Myeloid Leukemia", Nature Medicine, 18(7):1118-1122.
Kiselyov Alexander S. (Apr. 2005) "Solid Support Synthesis of 15-Membered Macrocycles Containing a Serotonin Unit", Tetrahedron Letters, 46(17):3007-3010.
Kralovics et al. (Apr. 2005) "A Gain-of-function Mutation of JAK2 in Myeloproliferative Disorders", The New England Journal of Medicine, 352(17):1779-1790.
Lacronique et al. (1997) "A TEL-JAK2 Fusion Protein with Constitutive Kinase Activity in Human Leukemia", Science, 278(5341):1309-1312.
Lafave et al. (2012) "JAK2 The Future: Therapeutic Strategies for JAK-Dependent Malignancies", Trends in Pharmacological Sciences, 33(11):574-582.
Levine et al. (Apr. 2005) "Activating Mutation in the Tyrosine Kinase JAK2 in Polycythemia Vera, Essential Thrombocythemia, and Myeloid Metaplasia with Myelofibrosis", Cancer Cell, 7(4):387-397.
Lim et al. (2015) "Discovery of 5-Amino-N-(1H-pyrazol-4-yl)pyrazolo[1,5-a]pyrimidine-3-carboxamide Inhibitors of IRAK4", ACS Medicinal Chemistry Letters, 6(6):683-688.
Liu et al. (Jul. 2004) "Antiproliferative Effects of Src Inhibition on Medullary Thyroid Cancer", The Journal of Clinical Endocrinology & Metabolism, 89(7):3503-3509.
Liu et al. (2012) "Deregulated MYC Expression Induces Dependence Upon AMPK-Related Kinase 5", Nature, 483:608-612.
Verstovsek et al. (2012) "A Double-Blind, Placebo-Controlled Trial of Ruxolitinib for Myelofibrosis", The New England Journal of Medicine, 366(9):799-807.
Vetrie et al. (1993) "The Gene Involved in X-Linked Agammaglobulinaemia is a Member of the Src Family of Protein-Tyrosine Kinases", Nature, 361:226-233.
Zhang et al. (Jul. 1, 2012) "Activation of the AXL Kinase Causes Resistance to EGFR-Targeted Therapy in Lung Cancer", Nature Genetics, 44(8):852-860.
Ma et al. (2008) "Expression and Mutational Analysis of MET in Human Solid Cancers", Genes Chromosomes Cancer, 47(12):1025-1037.
Manning et al. (Dec. 6, 2002) "The Protein Kinase Complement of the Human Genome", Science, 298(5600):1912-1934.
Maulik et al. (2002) "Role of the Hepatocyte Growth Factor Receptor, c-Met, in Oncogenesis and Potential for Therapeutic Inhibition", Cytokine & Growth Factor Reviews, 13(1):41-59.
Mccarthy et al. (May 2014) "Tropomyosin Receptor Kinase Inhibitors: A Patent Update 2009-2013", Expert Opinion on Therapeutic Patents, 24(7):731-744.
Miller et al. (2007) "Solvent Systems for Crystallization and Polymorph Selection", Chapter 3 in Solvent Systems and Their Selection in Pharmaceutics and Biopharmaceutics Series Biotechnology: Pharmaceutical Aspects vol. VI Auguslijns, Patrick; Brewster, Marcus (Eds.), 53-109.
Mohamed et al. (2009) "Bruton's Tyrosine Kinase (Btk): Function, Regulation, and Transformation with Special Emphasis on the PH Domain", Immunological Reviews, 228(1):58-73.
Monti Elena (2007) "Molecular Determinants of Intrinsic Multidrug Resistance in Cancer Cells and Tumors", Cancer Drug Resistance, 241-260.
Morris et al. (1994) "Fusion of a Kinase Gene, ALK, to a Nucleolar Protein Gene, NPM, in Non-Hodgkin's Lymphoma", Science, 263(5151):1281-1284.
Mossé et al. (Oct. 16, 2008) "Identification of ALK as a Major Familial Neuroblastoma Predisposition Gene", Nature, 455(7215):930-935.
Müller et al. (Nov. 11, 1993) "The Protein Tyrosine Kinase JAK1 Complements Defects in Interferon-alpha/beta and -gamma Signal Transduction", Nature, 366(6451):129-135.
Mulligan Lois M. (2014) "RET Revisited: Expanding the Oncogenic Portfolio", Nature Reviews Cancer, 14(3):173-186.
Murray Peter J. (2007) "The JAK-STAT Signaling Pathway: Input and Output Integration", Journal of Immunology, 178(5):2623-2629.
Nefedova et al. (Oct. 15, 2005) "Regulation of Dendritic Cell Differentiation and Antitumor Immune Response in Cancer by Pharmacologic-Selective Inhibition of the Janus-Activated Kinase 2/signal Transducers and Activators of Transcription 3 Pathway", Cancer Research, 65(20):9525-9535.
Neubauer et al. (May 1998) "Jak2 Deficiency Defines an Essential Developmental Checkpoint in Definitive Hematopoiesis", Cell, 93(3):397-409.
Nosaka et al. (Jan. 1, 1995) "Defective Lymphoid Development in Mice Lacking Jak3", Biochemistry, Molecular Biology, and Biophysics (CBS), 270(5237):800-802.
Okamoto et al. (May 2010) "Identification Of c-Src as a Potential Therapeutic Target for Gastric Cancer and of Met Activation as a Cause of Resistance to c-Src Inhibition", Molecular Cancer Therapeutics, 9(5):1188-1197.
Ongusaha et al. (2003) "P53 Induction and Activation of DDR1 Kinase Counteract P53-Mediated Apoptosis and Influence P53 Regulation through a Positive Feedback Loop", The EMBO Journal, 22(6):1289-1301.
Otsuka et al. (Nov. 15, 1998) "c-Met Autocrine Activation Induces Development of Malignant Melanoma and Acquisition of the Metastatic Phenotype1", Cancer Research, 58:5157-5167.

(56) References Cited

OTHER PUBLICATIONS

Pachnis et al. (1993) "Expression of the c-ret Proto-oncogene during Mouse Embryogenesis", Development, 119:1005-1017.
Pachter et al. (Feb. 1, 1961) "The Chemistry of Hortiamine and 6-Methoxyrhetsinine1", Journal of the American Chemical Society, 83(3):635-642.
Park et al. (2014) "CRIPTO1 Expression in EGFR-mutant NSCLC Elicits Intrinsic EGFR-inhibitor Resistance", The Journal of Clinical Investigation, 124(7):3003-3015.
Park et al. (Jun. 20, 1986) "Mechanism of Met Oncogene Activation", Cell, 45(6):895-904.
Parsons et al. (2004) "Src Family Kinases, Key Regulators of Signal Transduction", Oncogene, 23:7906-7909.
Pennacchietti et al. (Nov. 2014) "Microenvironment-Derived HGF Overcomes Genetically Determined Sensitivity to Anti-MET Drugs", Cancer Research, 74(22):6598-6609.
Pesu et al. (Jul. 2008) "Therapeutic Targeting of Janus Kinases", Immunological Reviews, 223(1):132-142.
Peterson et al. (2006) "Expanding the Scope of Crystal Form Evaluation in Parmaceutical Science", Journal of Pharmacy & Pharmaceutical Science, 9(3):317-326.
Pierotti et al. (Jan. 2006) "Oncogenic Rearrangements of the NTRK1/NGF Receptor", Cancer Letters, 232(1):90-98.
Politi et al. (2014) "Perfect ALKemy: Optimizing the Use of ALK-Directed Therapies in Lung Cancer", Clinical Cancer Research, 20(22):5576-5578.
Pulford et al. (2004) "Oncogenic Protein Tyrosine Kinases", Cellular and Molecular Life Sciences CMLS vol. 61:2939-2953.
International Preliminary Report on Patentability received for Application No. PCT/US2016/043132, mailed on Feb. 1, 2018, 7 Pages.
International Search Report and Written Opinion received for Application No. PCT/US2015/012597, mailed on Aug. 28, 2015, 11 Pages.
International Search Report and Written Opinion received for Application No. PCT/US2016/043132, mailed on Sep. 28, 2016, 8 Pages.
International Search Report and Written Opinion received for Application No. PCT/US2016/040329, mailed on Sep. 7, 2016, 13 pages.
International Search Report and Written Opinion received for Application No. PCT/US2016/040972, mailed on Sep. 13, 2016, 8 Pages.
International Search Report and Written Opinion received for Application No. PCT/US2017/044214, mailed on Dec. 1, 2017, 11 Pages.
Advani et al. (Aug. 2002) "Bcr-Abl Variants: Biological and Clinical Aspects", Leukemia Research, 26(8):713-720.
Zardan et al. (2014) "Lyn Tyrosine Kinase Regulates Androgen Receptor Expression and Activity in Castrate-resistant Prostate Cancer", Oncogenesis e115, 3:10 pages.
Anastassiadis et al. (2011) "Comprehensive Assay of Kinase Catalytic Activity Reveals Features of Kinase Inhibitor Selectivity", Nature Biotechnology, 29(11):1039-1045.
Awad et al. (2013) "Acquired Resistance to Crizotinib from a Mutation in CD74-ROS1", The New England Journal of Medicine, 368(25):2395-2401.
Yu et al. (Apr. 2013) "Analysis of Tumor Specimens at the Time of Acquired Resistance to EGFR-TKI Therapy in 155 Patients with EGFR-Mutant Lung Cancers", Clinical Cancer Research, 19(8):2240-2247.
Baldanzi et al. (Mar. 2015) "Physiological Signaling and Structure of the HGF Receptor MET", Biomedicines, 3(1):1-31.
Yu et al. (2010) "An Integrated Network of Androgen Receptor, Polycomb, and TMPRSS2-ERG Gene Fusions in Prostate Cancer Progression", Cancer Cell, 17(5):443-454.
Bardelli et al. (2013) "Amplification of the MET Receptor Drives Resistance to Anti-EGFR Therapies in Colorectal Cancer", Cancer Discovery, 3(6):658-673.

Baxter et al. (2005) "Acquired Mutation of the Tyrosine Kinase JAK2 in Human Myeloproliferative Disorders", Lancet, 365(9464):1054-1061.
Yano et al. (2008) "Hepatocyte Growth Factor Induces Gefitinib Resistance of Lung Adenocarcinoma with Epidermal Growth Factor Receptor-activating Mutations", Cancer Research, 68(22):9479-9487.
Xie et al. (Jan. 10, 2012) "Hepatocyte Growth Factor (HGF) Autocrine Activation Predicts Sensitivity to MET Inhibition in Glioblastoma", Proceedings of the National Academy of Sciences, 109(2):570-575.
Bertotti et al. (Aug. 2010) "Inhibition of Src Impairs the Growth of Met-Addicted Gastric Tumors", Clinical Cancer Research, 16(15):3933-3943.
Bischof et al. (Apr. 1997) "Role of the Nucleophosmin (NPM) Portion of the Non-Hodgkin's Lymphoma-Associated NPM-Anaplastic Lymphoma Kinase Fusion Protein in Oncogenesis", Molecular And Cellular Biology, 17(4):2312-2325.
Boccaccio et al. (2006) "Invasive Growth: A MET-driven Genetic Programme for Cancer and Stem Cells", Nature Reviews Cancer, 6(8):637-645.
Wrobel et al. (2004) "Autocrine CSF-1R Activation Promotes Src-dependent Disruption of Mammary Epithelial Architecture", Journal of Cell Biology, 165(2):263-273.
Bottaro et al. (Feb. 15, 1991) "Identification of the Hepatocyte Growth Factor Receptor as the c-met Proto-Oncogene Product", Science, 251(4995):802-804.
Bromann et al. (2004) "The Interplay between Src Family Kinases and Receptor Tyrosine Kinases", Oncogene, 2004, 23:7957-7968.
Buchert et al. (2016) "Targeting JAK Kinase in Solid Tumors: Emerging Opportunities and Challenges", Oncogene, 35:939-951.
Charest et al. (May 2003) "Fusion of FIG to the Receptor Tyrosine Kinase ROS in a Glioblastoma wth an Interstitial Del(6)(Q21q21)", Genes Chromosomes Cancer, 37(1):58-71.
Chiron et al. (2014) "Cell-Cycle Reprogramming for PI3K Inhibition Overrides a Relapse-Specific C481S BTK Mutation Revealed by Longitudinal Functional Genomics in Mantle Cell Lymphoma", Cancer Discovery, 4(9):1022-1035.
Cooper et al. (1984) "Molecular Cloning of a New Transforming Gene from a Chemically Transformed Human Cell Line", Nature, 311:29-33.
Couronne et al. (Nov. 15, 2013) "Activating Mutations in fyn Kinase in Peripheral T-Cell Lymphomas", Blood, 122(21):811.
Crystal et al. (2014) "Patient-derived Models of Acquired Resistance Can Identify Effective Drug Combinations for Cancer", Science, 346(6216):1480-1486.
Cui et al. (Aug. 3, 2011) "Structure Based Drug Design of Crizotinib (PF-02341066), a Potent and Selective Dual Inhibitor of Mesenchymal-Epithelial Transition Factor (c-MET) Kinase and Anaplastic Lymphoma Kinase (ALK)", Journal of Medicinal Chemistry, 54(18):6342-6363.
Davies et al. (Aug. 1, 2013) "Molecular Pathways: ROS1 Fusion Proteins in Cancer", Clinical Cancer Research, 19(15):4040-4045.
Di Paolo et al. (Jan. 2011) "Specific Btk Inhibition Suppresses B Cell- and Myeloid Cell-mediated Arthritis", Nature Chemical Biology, 7:41-50.
Dulak et al. (2011) "HGF-independent Potentiation of EGFR Action by c-met", Oncogene, 30(33):3625-3635.
Woyach et al. (2014) "Resistance Mechanisms for the Bruton's Tyrosine Kinase Inhibitor Ibrutinib", The New England Journal of Medicine, 370(24):2286-2294.
Engelman et al. (May 18, 2007) "MET Amplification Leads to Gefitinib Resistance in Lung Cancer by Activating ERBB3 Signaling", Science, 316(5827):1039-1043.
Fujita-Sato et al. (2015) "Enhanced MET Translation and Signaling Sustains K-Ras-Driven Proliferation under Anchorage-Independent Growth Conditions", Cancer Research, 75(14):2851-2862.
Furman et al. (2014) "Ibrutinib Resistance in Chronic Lymphocytic Leukemia", The New England Journal of Medicine, 370(24):2352-2354.
Gainor et al. (2013) "Novel Targets in Non-small Cell Lung Cancer: ROS1 and RET Fusions", Oncologist, 18(7):865-875.

(56) References Cited

OTHER PUBLICATIONS

Wojcik et al. (2006) "A Novel Activating Function of c-Src and Stat3 on HGF Transcription in Mammary Carcinoma Cells", Oncogene, 25(19):2773-2784.
Gargalionis et al. (Jun. 21, 2013) "The Molecular Rationale Of Src Inhibition in Colorectal Carcinomas", International Journal of Cancer, 134(9):2019-2029.
Gherardi et al. (2012) "Targeting MET in Cancer: Rationale and Progress", Nature Reviews Cancer, 12(2):89-103.
Ghiso et al. (Aug. 2013) "Targeting MET: Why, Where and How?", Current Opinion in Pharmacology, 13(4):511-518.
Golubovskaya et al. (2014) "Targeting FAK in Human Cancer: From Finding to First Clinical Trials", Frontiers in Bioscience (Landmark Ed), 19:687-706.
Gottesman Michael M. (2002) "Mechanisms of Cancer Drug Resistance", Annual Review of Medicine, 53:615-627.
Grande et al. (2011) "Targeting Oncogenic ALK: A Promising Strategy for Cancer Treatment", Molecular Cancer Therapeutics, 10:569-579.
Gridelli et al. (Mar. 2014) "ALK inhibitors in the treatment of advanced NSCLC", Cancer Treatment Reviews, 40(2):300-306.
Grieco et al. (1990) "PTC Is a Novel Rearranged form of the ret Proto-Oncogene and Is Frequently Detected In Vivo In Human Thyroid Papillary Carcinomas", Cell, 60(4):557-563.
Gu et al. (2011) "Survey of Tyrosine Kinase Signaling Reveals ROS Kinase Fusions in Human Cholangiocarcinoma", PLoS One, 6(1):9 Pages.
Hackam et al. (Oct. 11, 2006) "Translation of Research Evidence From Animals to Humans", JAMA, 296(14):1731-1732.
Halland et al. (Feb. 13, 2014) "Small Macrocycles As Highly Active Integrin α2β1 Antagonists", ACS Medicinal Chemistry Letters, 5(2):193-198.
Kim et al. (2014) "Guideline Recommendations for Testing of ALK Gene Rearrangement in Lung Cancer: A Proposal of the Korean Cardiopulmonary Pathology Study Group", The Korean Journal of Pathology, 48(1): 1-9.
Zou et al. (Mar. 17, 2015) "Pf-06463922 is a Potent and Selective Next-Generation Ros1/Alk Inhibitor Capable of Blocking Crizolinibesislanl Ros1 Mutations", Proceedings of the National Academy of Sciences, 112(11):3493-3498.

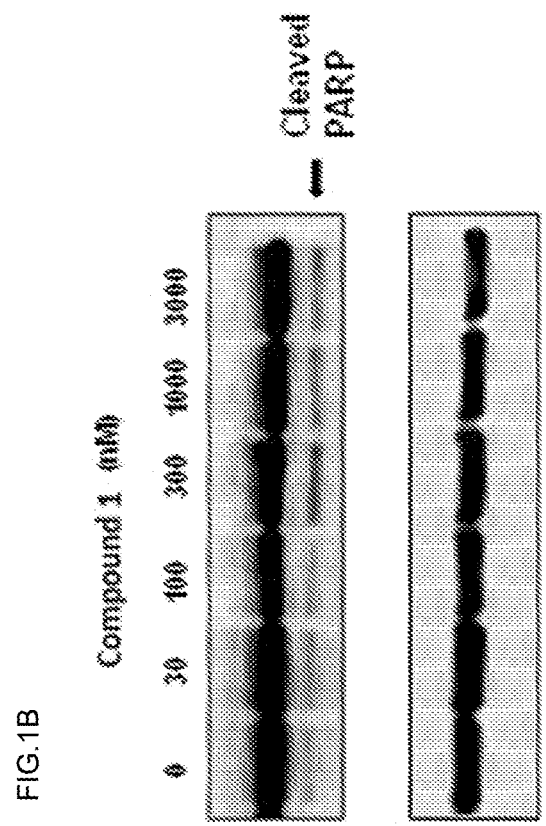
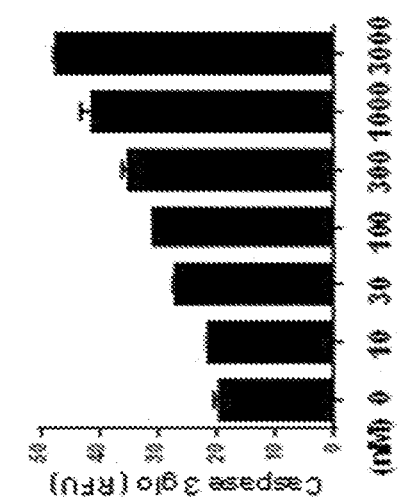
FIG. 1A
FIG. 1B

CHIRAL DIARYL MACROCYCLES AND USES THEREOF

CROSS REFERENCE TO RELATED APPLICATIONS

This application is a continuation of U.S. application Ser. No. 16/998,763, filed Aug. 20, 2020, issued as U.S. Pat. No. 11,452,725, which is a continuation of U.S. application Ser. No. 15/745,915, filed Jan. 18, 2018, which is a national stage entry of PCT/US2016/043132, filed Jul. 20, 2016, which claims priority under 35 U.S.C. § 119(e) to U.S. Provisional Application Ser. No. 62/195,081, filed Jul. 21, 2015 and U.S. Provisional Application Ser. No. 62/302,231, filed Mar. 2, 2016, each which are incorporated herein by reference in their entirety.

TECHNICAL FIELD

This disclosure relates to the use of certain diaryl macrocycle compounds, specifically (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one in the treatment of disease in mammals. This disclosure also relates to compositions including such compounds, and to methods of using such compositions in the treatment of diseases in mammals, especially in humans.

BACKGROUND

Protein kinases are key regulators for cell growth, proliferation and survival. Genetic and epigenetic alterations accumulate in cancer cells leading to abnormal activation of signal transduction pathways which drive malignant processes. (Manning, G.; Whyte, D. B.; Martinez, R.; Hunter, T.; Sudarsanam, S. The protein kinase complement of the human genome. *Science* 2002, 298, 1912-1934). Pharmacological inhibition of these signaling pathways presents promising intervention opportunities for targeted cancer therapies. (Sawyers, C. Targeted cancer therapy. *Nature* 2004, 432, 294-297).

Anaplastic lymphoma kinase (ALK), along with leukocyte tyrosine kinase (LTK), belongs to the insulin receptor (IR) superfamily of receptor tyrosine kinases. ALK is mainly expressed in the central and peripheral nervous systems suggesting a potential role in normal development and function of the nervous system. (Pulford K, et al *Cell Mol. Life Sci.* 2004, 61, 2939). ALK was first discovered as a fusion protein, NPM (nucleophosmin)-ALK encoded by a fusion gene arising from the t(2;5)(p23;q35) chromosomal translocation in anaplastic large cell lymphoma (ALCL) cell lines in 1994. (Morris S W, et al *Science* 1994, 263, 1281.) More than twenty distinct ALK translocation partners have been discovered in many cancers, including ALCL (60-90% incidence), inflammatory myofibroblastic tumours (IMT, 50-60%), non-small cell lung carcinomas (NSCLC, 3-7%), colorectal cancers (CRC, 0-2.4%), breast cancers (0-2.4%), and other carcinomas with rare incidence. (Grande E, et al *Mol. Cancer Ther.* 2011, 10, 569.) Oncogenic point mutations of ALK have been discovered in both familial and sporadic cases of neuroblastoma. (Mossé Y P, et al *Nature* 2008, 455, 930-935.) Both fusion and mutant ALKs are highly oncogenic, which generate considerable interest and efforts in developing ALK inhibitors for the treatment of haematopoietic, solid, and mesenchymal tumors with abnormal ALK gene. (Grande, E, et al *Mol. Cancer Ther.* 2011, 10, 569-579.). Crizotinib was approved by the US Food and Drug Administration for the treatment of ALK-positive non-small cell lung cancer. Similar with many targeted therapies of kinase inhibitors, crizotinib drug resistance developed in about 10 months. Mechanisms of drug resistance include target gene amplification or overexpression, development of secondary missense mutations, and use of alternative signaling pathway (so-called "bypass resistance"). As a result, second-generation ALK inhibitors have been developed to be more potent against wild and many mutant ALKs. One such mutation is the gatekeeper mutation $ALK^{L1196M}$. Ceritinib was approved by the US Food and Drug Administration for the treatment of patients with ALK-positive non-small cell lung cancer showing disease progression or who are intolerant to crizotinib. Although many second generation ALK inhibitors have been investigated in clinical trials, new ALK mutations resistant to the second generation ALK inhibitors have emerged. For example, the G1202R mutation has been found in tumors resistant to crizotinib, ceritinib, and alectinib. (Politi K, *Clin Cancer Res.* 2014, 20, 5576.) Novel isoforms of ALK consisting primarily of the intracellular tyrosine kinase domain was found to express in ~ 11% of melanomas and sporadically in other human cancer types, but not in normal tissues (Wiesner T, et al *Nature* 2015, 526, 453-457). These new ALK isoforms stimulate multiple oncogenic signalling pathways, and are sensitive to ALK inhibitors, suggesting potential clinical benefits from ALK inhibition.

Non-small cell lung cancers harboring ALK gene rearrangements are sensitive to treatment with the ALK inhibitor crizotinib. However, the emergence of drug resistance is universal and rapidly limits clinical applicability. The mechanisms of resistance include ALK gene amplification, acquired ALK missense mutations, bypass pathway activation, and epithelial-mesenchymal transition (EMT) (Katayama R 2012). (Katayama R., et al Sci Transl Med. 2012, 4(120):120ra17) Bypass and EMT constitute majority of the acquired resistant population. It is worth to note that 30-40% of ALK fusion positive patients have intrinsic resistance to ALK inhibitor treatment. ALK rearranged NSCLCs are typically adenocarcinoma characterized by a solid signetring cell pattern that is frequently associated with a metastatic phenotype and linked to an epithelial-mesenchymal transition (EMT) phenotype. (Voena C, et al. *Oncotarget*, 2016, Apr. 23, 8955) The H2228 cell line with EML4-ALK v3 fusion gene displayed a mesenchymal phenotype with directly suppressing E-cadherin and up-regulating vimentin expression, as well as expression of other genes involved in EMT. H2228 cell line confers intrinsic resistance to crizotinib and other ALK inhibitors. Therefore, it is necessary to develop a polypharmacology ALK inhibitor being able to target EMT and metastasis. Bypass resistance occurs when the original driver oncogene and a secondary bypass track redundantly maintain downstream signaling to promote cell survival and proliferation. For example, ALK inhibition in patient-derived ALK models has been shown to up-regulate SRC activity. The combination of a Src tyrosine kinase inhibitor with an ALK inhibitor was shown to effectively suppress downstream signaling, generated a synergistic inhibition effect, and re-sensitized the ALK inhibitors in the patient-derived ALK models in vitro and in vivo. (Crystal A S, *Science.* 2014, 346, 1480.) The identification of new ALK inhibitors that can counter broad secondary ALK mutations including $ALK^{G1202R}$ and inhibit Src signaling will be important and highly desired for effectively overcoming ALK drug resistance and sustaining the response to ALK inhibitor treatment.

ROS1 protein is a receptor tyrosine kinase, closely related to the ALK/LTK and insulin receptor kinase family. Although normal physiologic functions of human ROS1 kinase have not been fully understood, the abnormal expression and variable constitutively activating fusion forms of ROS1 kinase have been reported in a number of cancers including glioblastoma, non-small cell lung cancer, cholangiocarcinoma, ovarian cancer, gastric adenocarcinoma, colorectal cancer, inflammatory myofibroblastic tumor, angiosarcoma, and epithelioid hemangioendothelioma. (Kurtis D D, et al *Clin Cancer Res* 2013, 19 (15), 1.) FIG-ROS1 fusion protein was the first fusion protein of ROS1 discovered in 2003 in a human glioblastoma multiforme. (Charest A, et al *Genes Chromosomes Cancer* 2003, 37, 58) Several fusion proteins with ROS1 kinase including TPM3, SDC4, SLC34A2, CD74, EZR, and LRIG3 have been reported from human lung cancers, suggesting the oncogenic role of ROS1 kinase in lung cancers. (Takeuchi K, et al *Nat. Med.* 2012, 18, 378) The survey of activated tyrosine kinases signaling in 23 cholangiocarcinoma patients confirmed the presence of FIG-ROS kinase fusion in 8.7% of cholangiocarcinoma patients. (Gu T L, et al *PLoS One.* 2011, 6, e15640.) More and more ROS1 fusion partners including KDELR2, CCDC6, MSN, LIMA1, CLTC, NFκB2, NCOR2, CEP85L, TMEM106B, HLA-A, MYO5A, PPFIBP1, ERC1, PWWP2A, CLIP1, ZCCHC8, SHTN1, TFG, and YWHAE have been reported from various human cancers (Uquen A, et al *Future Oncol.* 2016, June 3, Epub ahead of print) Taken together, ROS1 kinase is a promising molecular based target candidate for cancers with aberrant ROS kinase activities. The ALK/MET/ROS1 inhibitor crizotinib has demonstrated marked efficacy in patients with NSCLC whose tumors are positive for ROS1 genetic abnormalities. (Shaw A T, et al *N Engl J Med* 2015, 372, 683). As expected ROS1 rearrangement-positive patients who responded to crizotinib eventually experienced disease progression. The secondary $ROS1^{G2032R}$ mutation and bypass signaling are associated with the resistance. (Awad M M, et al *N Engl J Med* 2013, 368, 2395) It is desired to develop the next generation of ROS1 inhibitor to overcome the resistance.

The tropomyosin-related receptor tyrosine kinases (Trks) are high-affinity receptors for neurotrophins (NTs), a nerve growth factor (NGF) family. Trk was originally cloned as an oncogene fused with the tropomyosin gene in the extracellular domain. The activating mutations caused by chromosomal rearrangements or mutations in TRK family have been reported in many cancers. (Vaishnavi A, et al *Cancer Discov.* 2015, 5, 25) Because Trks play important roles in pain sensation as well as tumour cell growth and survival signaling, inhibitors of Trk receptor kinases might provide benefit for pain and cancer treatment.

The Janus family of kinases (JAKs) include JAK1, JAK2, JAK3 and TYK2, and are cytoplastic non-receptor tyrosine kinases required for the physiologic signaling of cytokines and growth factors. (Quintas-Cardama A, et al., *Nat. Rev. Drug Discov.* 2011, 10(2), 127) Aberrant regulation of JAK/STAT pathways has been implicated in multiple human pathological diseases, including cancer (JAK2) and rheumatoid arthritis (JAK1, JAK3). A gain-of-function mutation of JAK2 (JAK2V617F) has been discovered with high frequency in MPN patients. (Levine R L, et al. *Cancer Cell* 2005, 7, 387) The mutation in the JH2 pseudokinase domain of JAK2 leads to constitutively kinase activity. Cells containing the JAK2V617F mutation acquire cytokine-independent growth ability and often become tumor, providing strong rationale for the development of JAK inhibitors as a targeted therapy. In addition, hyperactivation of the JAK2/signal transducers and activators of transcription 3 (JAK2/STAT3) is responsible for abnormal dendritic cell differentiation leading to abnormal dendritic cell differentiation and accumulation of immunosuppressive myeloid cells in cancer (Nefedova Y, et al. *Cancer Res* 2005, 65, 9525). In Pten-null senescent tumors, activation of the JAK2/STAT3 pathway establishes an immunosuppressive tumor microenvironment that contributes to tumor growth and chemoresistance (Toso A, et al. *Cell Reports* 2014, 9, 75). JAK2 gene fusions with the TEL(ETV6) (TEL-JAK2) and PCM1 genes have been found in leukemia patients. (Lacronique V, et al. *Science* 1997, 278, 5341, 1309-12. Reiter A, et al. *Cancer Res.* 2005, 65, 7, 2662-7.) It was reported that JAK/STAT3 signaling pathway was aberrantly increased in EGFR inhibitor-resistant EGFR-mutant non-small cell lung cancer (NSCLC) cells, and JAK2 inhibition overcomes acquired resistance to EGFR inhibitors that support the use of combination therapy with JAK and EGFR inhibitors for the treatment of EGFR-dependent NSCLC. (Gao S P, et al. *Sci Signal.* 2016, 9 (421):ra33) JAK/STAT3 signaling promotes cancer hallmarks in the tumor and its environment, including proliferation, survival, angiogenesis, tumor metabolism while suppressing antitumor immunity. (Buchert M, et al. *Oncogene,* 2016, 35, 939-951) Inhibition of cytokine-dependent activation of the JAK/STAT3 pathway with JAK inhibitors may also afford orthogonal treatment opportunities for other oncogene-addicted cancer cells that have gained drug resistance. Focal amplification of JAK2 gene was observed in postchemotherapy triple-negative breast cancers (TNBCs) in a group of 9p24-amplified tumors, suggesting a role in tumorigenicity and chemoresistance. (Balko J M, et al. Sci Transl Med. 2016, 8(334):ra53) Therefore, pharmacologic inhibition of the JAK2 signaling pathway can be an important new therapeutic strategy to enhance antitumor activity.c-Src is a nonreceptor tyrosine kinase. The Src family (SFK) comprises of eight members in humans (Src, Fyn, Yes, Lyn, Lck, Hck, Blk and Fgr) with a molecular weight between 52-62 KDa. Src and its family members are deregulated in many types of cancer. Src is a key downstream transducer of many RTKs, including EGFR, HER2, and c-Met. Activation of Src signaling has been implicated in conferring therapeutic resistance to targeted antiendocrine therapies, receptor tyrosine kinase therapies, traditional chemotherapies, and radiation therapies. (Zhang S, et al Trends Pharmacol Sci. 2012, 33, 122). SRC can promote signaling from growth factor receptors in a number of ways including participation in signaling pathways required for DNA synthesis, control of receptor turn-over, actin cytoskeleton rearrangement, migration, adhesion, invasion, motility, and survival. (Bromann P A, Oncogene 2004, 23, 7957-7968) A prominent role of Src in tumor progression-related events such as the epithelial-mesenchymal transition (EMT) and the development of metastasis have been reported through the interaction with the potent metastasis suppressor, N-myc downstream regulated gene 1 (NDRG1), that regulates cancer cell migration by inhibiting Src activity. (Liu W, et al. Oncotarget. 2015, 6: 35522-35541) Although EGFR inhibitors have achieved a significant success in the majority of NSCLC patients harbor EGFR-activating mutations, a subset of patients with EGFR mutations are refractory to EGFR-TKIs. Resistance to EGFR inhibitors reportedly involves SRC activation and induction of epithelial-to-mesenchymal transition (EMT). The primary resistance to EGFR-TKIs is associated with higher levels of CRIPTO1 expression. CRIPTO1 activated SRC and ZEB1 to promote EMT via microRNA-205 (miR-205) downregulation. Therefore, co-targeting EGFR and SRC may overcome intrinsic EGFR-inhibitor resistance in patients with CRIPTO1-positive, EGFR-mutated NSCLC. (Park, K-S, et al. J Clin Invest. 2014, 124(7):3003-3015) Focal Adhesion Kinase (FAK) is a 125 kDa non-receptor tyrosine kinase and plays a significant role in adhesion, survival, motility, metastasis, angiogenesis, lymphangiogenesis, cancer stem cell functions, tumor microenvironment and epithelial to mesenchymal transition (EMT). (Golubovskaya V M, Front Biosci (Landmark Ed). 19: 687-706) Nuclear FAK controls chemokine transcription, Tregs, and evasion of antitumor immunity, and the small-molecule FAK kinase inhibitor VS-4718 drives depletion of Tregs and promotes a CD8+ T cell-mediated antitumor response. (Serrels A, et al, Cells 2015, 163, 160-173) .Therefore, FAK inhibitors may trigger immune-mediated tumor regression. FAK is hyperactivated in human pancreatic ductal adenocarcinoma (PDAC) and correlates with immunosuppressive tumor microenvironment (TME). Targeting focal adhesion kinase renders pancreatic cancers responsive to checkpoint immunotherapy by overcoming the fibrotic and immunosuppressive PDAC TME in mouse models. (Jiang H, et al. Nat Med. 2016, Jul. 4 [Epub ahead of print]). Recently it was reported that saracatinib, a selective SRC inhibitor, can re-sensitize ALK inhibitor-resistant cell lines, demonstrating a therapeutic role of SRC inhibition in overcoming ALK inhibitor resistance. (Crystal A S, et al. Science 2014, 346, 1480-1486) Therefore, Src/FAK inhibitor may play important roles in combinatorial regimens in overcoming resistance to current anticancer therapies and in preventing metastatic recurrence, EMT and cancer treatment resistance. AMP-activated protein kinase family member 5 (ARK5), also called NAUK1 is an upstream regulator of AMPK and limits protein synthesis via inhibition of rapamycin 1 (mTORC1) signalling pathway. ARK5 maintains expression of mitochondrial respiratory chain complexes and respiratory capacity for efficient glutamine metabolism. ARK5 is highly expressed in both primary NSCLC tissues and cell lines, that is functionally associated with NSCLC metastasis and a predictor of poor prognosis for NSCLC patients. ARK5 modulated the migration and invasion of NSCLC cells and played crucial roles in mTOR pathway. (Shi L, et al. Br J Cancer. 2014, 111(12):2316-27) It was reported that ARK5 confers doxorubicinresistance in HCC via inducing EMT. (Xu T, et al. Cancer Lett. 2016, 377(2): 140-8) Deregulated expression of the MYC oncoprotein is associated with many human tumors. MYC promotes cell growth and proliferation, and alters cellular metabolism. Inhibition of ARK5 leads to a collapse of cellular ATP levels in cells expressing deregulated MYC, and prolongs survival in MYC-driven mouse models of hepatocellular carcinoma. (Liu L, et al. Nature, 2012, 483, 608-612) Therefore, Targeting cellular energy homeostasis by ARK5 inhibitor is a valid therapeutic strategy to eliminate tumor cells with deregulated MYC expression.

Src is a non-receptor tyrosine kinase that is deregulated in many types of cancer, and a key downstream transducer of many RTKs, including EGFR, HER2, and c-Met. Activation of Src signaling has been implicated in conferring therapeutic resistance to targeted antiendocrine therapies, receptor tyrosine kinase therapies, traditional chemotherapies, and radiation therapies. (Zhang S, et al Trends Pharmacol Sci. 2012, 33, 122). Src inhibitor may play important roles in combinatorial regimens in overcoming resistance to current anticancer therapies and in preventing metastatic recurrence. Cytoplasmic tyrosine kinases (also known as non-receptor tyrosine kinases) of the Src family (SFKs) play important roles in signal transduction induced by a large number of extracellular stimuli including growth factors and integrins. Elevated SFK activity is found in more than 80% of human colorectal cancer (CRC) and this has been associated with poor clinical outcome. (Summy J M, et al. Cancer Metastasis Rev. 2003, 22, 337-358) The SFK member Yes regulates specific oncogenic signalling pathways important for colon cancer progression that is not shared with c-Src. (Scancier F. et al. PLoS One. 2011, 6(2): e17237) WASF2-FGR fusion genes were found in lung squamous carcinoma, ovarian serous cystadenocarcinoma, and skin cutaneous melanoma. (Stransky N, et al. Nature Communications 2014, 5, 4846) Estrogen receptor-positive (ER$^+$) breast cancers adapt to hormone deprivation and become resistant to antiestrogen therapy. Mutations in the inhibitory SH2 domain of the SRC family kinase (SFK) LYN were related to ER$^+$ tumors that remained highly proliferative after treatment with the aromatase inhibitor letrozole. LYN was upregulated in multiple ER$^+$ breast cancer lines resistant to long-term estrogen deprivation. (Schwarz L J, et al. J Clin Invest. 2014, 124, 5490-5502) Therefore, targeting LYN will be a rational strategy overcoming the escape from antiestrogens in a subset of ER$^+$ breast cancers. It was reported that LYN was overexpressed in castrate-resistant prostate cancer (CRPC), enhanced AR transcriptional activity, and accelerated CRPC progression, and targeting Lyn kinase induced AR dissociation from the molecular chaperone Hsp90, leading to its ubiquitination and proteasomal degradation. (Zardan A., et al. Oncogenesis 2014, 3, e115) The Lyn tyrosine kinase is a potential therapeutic target for the treatment of CRPC. The Src family kinase FYN is involved in signal transduction pathways in the nervous system, as well as the development and activation of T lymphocytes under normal physiological conditions. Activation of Fyn is observed in various cancers, including melanoma, glioblastoma, squamous cell carcinoma, prostate and breast cancers. (Elias D., et al. Pharmacological Research 2015, 100, 250-254) Fyn was upregulated in tamoxifen-resistant breast cancer cell lines and plays a key role in the resistance mechanism. Peripheral T-cell lymphomas (PTCLs) are a heterogeneous group of aggressive non Hodgkin lymphomas with poor prognosis. FYN activating mutations were found in PTCL, and promoted the growth of cells transformed via expression of activated FYN mutant alleles. SRC kinase inhibitors may play important roles in the treatment of PTCLs. (Couronne L, et al. Blood 2013, 122, 811).

Discoidin domain receptors (DDRs) are activated by matrix collagens and have been implicated in numerous cellular functions such as proliferation, differentiation, adhesion, migration, and invasion. DDRs play a role in cancer progression by regulating the interactions of tumor cells with their surrounding collagen matrix. DDR1 is a direct p53 transcriptional target, and the activation of DDR1 is associated with p53-dependent DNA damage. DDR1 activated the MAPK cascade in a Ras-dependent manner. Inhibition of DDR1 function led to increased apoptosis of wild-type p53-containing cells in response to genotoxic stress through a caspase-dependent pathway. (Ongusaha P P, et al. EMBO J. 2003, 22, 1289-1301) DDRs were identified as one of several major activated tyrosine kinases carrying somatic mutations in lung cancer (Hammerman P S, et al. Cancer Discov. 2011, 1, 78-89.), serous and clear cell endometrial cancer (Rudd M L, et al. BMC Cancer 2014, 14, 884), as well as in acute myeloid leukemia. (Tomasson M H, et al. Blood 2008, 111:4797-4808) Advanced Kirsten rat sarcoma viral oncogene homolog (KRAS)-mutant lung adenocarcinoma is challenging because of a lack of effective targeted therapies. The concomitant inhibition of both DDR1 and Notch signaling induced the regression of KRAS;TP53-mutant patient-derived lung xenografts (PDX), indicating the combined inhibition of DDR1 and Notch signaling could be an effective targeted therapy for patients with KRAS-mutant lung adenocarcinoma. (Ambrogia C, et al, Nature Medicine, 2016, 22, 270-277).

It is desirable to prepare compounds that have activity against disease-driving kinase inhibitors, especially compounds that have activity against multiple kinases, including against multiple genetically altered kinases for use as therapeutic agents in treating diseases. New compounds with polypharmacology profiles are also desired for targeting the primary oncogene drivers and their acquired resistance mechanisms including secondary mutations, bypath signaling, EMT, cancer stemness, and metastasis.

SUMMARY

Compounds of the formula I wherein $X^1$, $X^2$, $Z^1$, $Z^2$, $Z^3$, $Z^4$, $Z^5$, $Z^6$, $Z^7$, M, $R^1$, $R^2$, $R^3$, $R^4$, $R^5$ and $R^6$ are defined as described herein have been shown to have activity against wild-type and mutant ALK (anaplastic lymphoma kinase), wild-type and mutant ROS1 (ROS1 proto-oncogene receptor tyrosine kinase), the TRK family of kinases (tropomyosin-related receptor tyrosine kinases, TRKA/B/C), JAK2 of the Janus family of kinases and SRC (c-Src family of protein tyrosine kinases (SFKs)).

One such compound is (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one (also herein referred to as "Compound 1"), represented by the formula has been shown to be a potent small-molecule multi-target kinase inhibitor showing activity against wild-type and mutant ALK (anaplastic lymphoma kinase), wild-type and mutant ROS1 (ROS1 proto-oncogene receptor tyrosine kinase), the TRK family of kinases (tropomyosin-related receptor tyrosine kinases, TRKA/B/C), JAK2 of the Janus family of kinases and SRC (c-Src family of protein tyrosine kinases (SFKs)). Compound 1 has properties, including anti-tumor properties, which are pharmacologically mediated through inhibition of receptor and non-receptor tyrosine kinases. Compound 1 is disclosed in International Patent Application No. PCT/US2015/012597, which is incorporated herein by reference in its entirety.

In one aspect, the present disclosure provide a method of treating disease in a patient comprising, administering to the patient a therapeutically effective amount of a compound of the formula I wherein M is $CR^{4a}$ or N;

$X^1$ and $X^2$ are independently S, S(O), S(O)$_2$, O or N($R^9$)

$R^1$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each of $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS (O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS (O)$_2$NH$_2$, —N(C$_1$-C$_6$ alkyl)S(O)NH$_2$, —N(C$_1$-C$_6$ alkyl)S (O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH (C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, cycloalkyl, or monocyclic heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —OC$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

In another aspect, the present disclosure provides a method of treating cancer in a patient previously shown to express a genetically altered tyrosine or serine/throenine kinase comprising, administering to the patient a therapeutically effective amount of a compound of the formula I

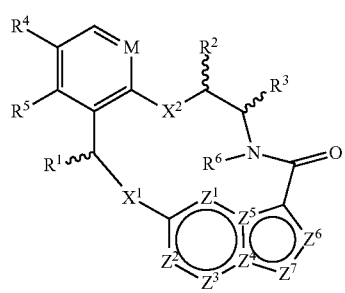

I wherein

M is CR$^{4a}$ or N;

X$^1$ and X$^2$ are independently S, S(O), S(O)$_2$, O or N(R$^9$)

R$^1$ is C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C (O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each of R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O) OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7 0173 membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, cycloalkyl, or monocyclic heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or heteroaryl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

each $Z^1$, $Z^2$, $Z^3$, $Z^4$, $Z^5$, $Z^6$ or $Z^7$ is independently N, NH, or $C(R^{10})$, wherein each $R^{10}$ is independently H, deuterium, halogen, $C_1$-$C_6$ alkyl, —$OC_1$-$C_6$ alkyl, —OH, —$NH_2$, —$NH(C_1$-$C_6$ alkyl), —NH(phenyl), —NH(heteroaryl), —CN, or —$CF_3$, and provided that at least one of $Z^1$, $Z^2$, $Z^3$, $Z^4$, $Z^5$, $Z^6$ or $Z^7$ is N or NH;

or a pharmaceutically acceptable salt thereof.

In another aspect, the present disclosure provides a method of treating cancer in a patient comprising;

i. identifying a genetically altered tyrosine or serine threonine kinase in the patient, and ii. administering to the patient a therapeutically effective amount of a compound of the formula I

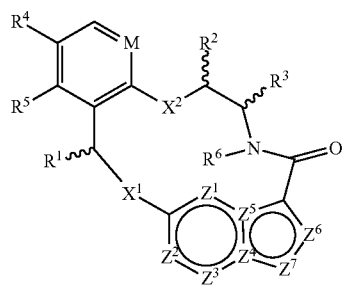

I wherein

M is $CR^{4a}$ or N;

$X^1$ and $X^2$ are independently S, S(O), $S(O)_2$, O or $N(R^9)$ $R^1$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$C(O)OR^7$ or —$C(O)NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, $NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, —$SC_1$-$C_6$ alkyl, —$S(O)C_1$-$C_6$ alkyl, —$S(O)_2C_1$-$C_6$ alkyl, —$S(O)$ $NH(C_1$-$C_6$ alkyl), —$S(O)_2NH(C_1$-$C_6$ alkyl), —$S(O)N(C_1$-$C_6$ alkyl)$_2$, —$S(O)_2N(C_1$-$C_6$ alkyl)$_2$, —$P(C_1$-$C_6$ alkyl)$_2$, —$P(O)(C_1$-$C_6$ alkyl)$_2$, $C_3$-$C_6$ cycloalkyl, or 3- to 7-membered heterocycloalkyl;

each of $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$C(O)OR^7$ or —$C(O)NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —$NH_2$, —$NH(C_1$-$C_6$ alkyl), —$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$-$C_6$ alkyl, —$N(C_1$-$C_6$ alkyl)$C(O)NH_2$, —$N(C_1$-$C_6$ alkyl)$C(O)NHC_1$-$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$-$C_6$ alkyl, —$N(C_1$-$C_6$ alkyl)$C(O)OC_1$-$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, NHS $(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)OC_1$-$C_6$ alkyl, —$C(O)NH_2$, —$C(O)NH(C_1$-$C_6$ alkyl), —$C(O)N(C_1$-$C_6$ alkyl)$_2$, —$SC_1$-$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl)$_2$, —$S(O)_2N(C_1$-$C_6$ alkyl)$_2$, —$P(C_1$-$C_6$ alkyl)$_2$, —$P(O)(C_1$-$C_6$ alkyl)$_2$, $C_3$-$C_6$ cycloalkyl, or 3- to 7-membered heterocycloalkyl;

$R^4$, $R^{4a}$ and $R^5$ are each independently H, fluoro, chloro, bromo, $C_1$-$C_6$ alkyl, —OH, —CN, —$OC_1$-$C_6$ alkyl, —$NHC_1$-$C_6$ alkyl, —$N(C_1$-$C_6$ alkyl)$_2$ or —$CF_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —$OC_1$-$C_6$ alkyl, —$NH_2$, —$NH(C_1$-$C_6$ alkyl), —$N(C_1$-$C_6$ alkyl)$_2$, —$CO_2H$, —$CO_2C_1$-$C_6$ alkyl, —$CONH_2$, —$CONH(C_1$-$C_6$ alkyl), —$CON(C_1$-$C_6$ alkyl)$_2$, cycloalkyl, or monocyclic heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or heteroaryl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —$OR^7$;

each $Z^1$, $Z^2$, $Z^3$, $Z^4$, $Z^5$, $Z^6$ or $Z^7$ is independently N, NH, or $C(R^{10})$, wherein each $R^{10}$ is independently H, deuterium, halogen, $C_1$-$C_6$ alkyl, —$OC_1$-$C_6$ alkyl, —OH, —$NH_2$, —$NH(C_1$-$C_6$ alkyl), —NH(phenyl), —NH(heteroaryl), —CN, or —$CF_3$, and provided that at least one of $Z^1$, $Z^2$, $Z^3$, $Z^4$, $Z^5$, $Z^6$ or $Z^7$ is N or NH;

or a pharmaceutically acceptable salt thereof.

In another aspect, the present disclosure provides a method of identifying a patient for treatment with a compound of the formula I

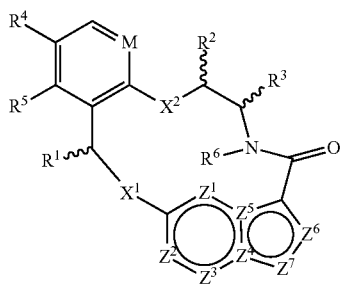

wherein

M is CR$^{4a}$ or N;

X$^1$ and X$^2$ are independently S, S(O), S(O)$_2$, O or N(R$^9$)

R$^1$ is C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each of R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, cycloalkyl, or monocyclic heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —OC$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof, comprising diagnosing the patient with a cancer mediated by a genetically altered tyrosine or serine/threonine kinase.

In another aspect, the present disclosure provides a use of compound of the formula I

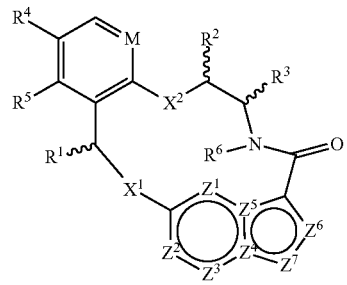

wherein

M is CR$^{4a}$ or N;

X$^1$ and X$^2$ are independently S, S(O), S(O)$_2$, O or N(R$^9$)

R$^1$ is C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C (O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each of R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, cycloalkyl, or monocyclic heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —OC$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof, in the preparation of a medicament for the treatment of a disease in a patient.

In another aspect, the present disclosure provides a use of compound of the formula I

I wherein

M is CR$^{4a}$ or N;

X$^1$ and X$^2$ are independently S, S(O), S(O)$_2$, O or N(R$^9$)

R$^1$ is C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each of R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, cycloalkyl, or monocyclic heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof, for treating cancer in a patient.

In another aspect, the present disclosure provides the use of compound of the formula I

I wherein

M is CR$^{4a}$ or N;

X$^1$ and X$^2$ are independently S, S(O), S(O)$_2$, O or N(R$^9$)

R$^1$ is C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each of R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, cycloalkyl, or monocyclic heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof, for treating pain in a patient.

In another aspect, the present disclosure provides use of a compound of the formula I

I wherein
M is CR$^{4a}$ or N;

X$^1$ and X$^2$ are independently S, S(O), S(O)$_2$, O or N(R$^9$)

R$^1$ is C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O) NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each of R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, cycloalkyl, or monocyclic heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —OC$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof, for treating cancer in a patient previously shown to express a genetically altered tyrosine or serine/threonine kinase.

In another aspect, the present disclosure provide a use a compound of the formula I

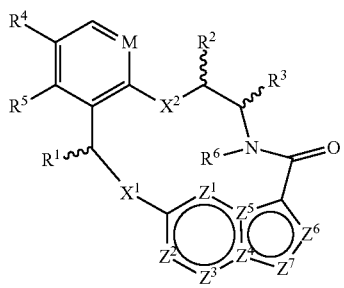

wherein

M is CR$^{4a}$ or N;

X$^1$ and X$^2$ are independently S, S(O), S(O)$_2$, O or N(R$^9$)

R$^1$ is C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each of R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, cycloalkyl, or monocyclic heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —OC$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof, for treating cancer in a patient, wherein the patient has been previously treated with a cancer therapeutic, and the cancer has developed resistance to the cancer therapeutic.

In another aspect, the present disclosure provides the use of a compound of the formula I

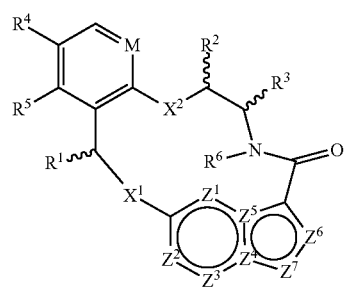

wherein

M is CR$^{4a}$ or N;

X$^1$ and X$^2$ are independently S, S(O), S(O)$_2$, O or N(R$^9$)

R$^1$ is C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-

C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each of R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$, R$^{4a}$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, cycloalkyl, or monocyclic heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^7$;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —OC$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof, for treating cancer in a patient previously shown to express a genetically altered tyrosine or serine/threonine kinase, wherein the patient has been previously treated with a cancer therapeutic, and the cancer has developed resistance to the cancer therapeutic.

In some embodiments of the aspects described above, the compound is (7S,13R)-11-fluoro-7,13-dimethyl-6,7,13,14-tetrahydro-1,15-ethenopyrazolo[4,3-f][1,4,8,10]benzoxatriaza-cyclotridecin-4(5H)-one, or a pharmaceutically acceptable salt thereof.

In some embodiments, the disease is mediated by a tyrosine or serine/threonine kinase selected from the group consisting of ALK, ROS1, TRKA, TRKB, TRKC, JAK2, SRC, FAK, ARK5, and combinations thereof. In some embodiments the disease is mediated by a receptor tyrosine kinase. In some embodiments, the receptor tyrosine kinase is selected from the group consisting of ALK, ROS1, TRKA, TRKB and TRKC. In some embodiments, the receptor tyrosine kinase is selected from the group consisting of ALK, ROS1, TRKA, TRKB and TRKC. In some embodiments, the disease is mediated by a non-receptor kinase. In some embodiments, the non-receptor kinase is JAK2, FYN, LYN, YES, FGR, SRC, FAK or ARK5. In some embodiments, the non-receptor kinase is JAK2, SRC, FAK or ARK5. In some embodiments, the disease is mediated by a non-receptor tyrosine kinase. In some embodiments, the non-receptor tyrosine kinase is JAK2, SRC or FAK. In some embodiments, the disease is mediated by a non-receptor serine/threonine kinase. In some embodiments, the non-receptor serine/threonine kinase is ARK5. In some embodiments, the disease is mediated by a protein tyrosine kinase. In some embodiments, the protein tyrosine kinase is TXK. In some embodiments, the disease is mediated by a discoidin domain receptor. In some embodiments, the discoidin domain receptor is DDR1. In some embodiments, the disease is selected from the group consisting of cancer, psoriasis, rheumatoid arthritis, polycythemia vera, essential thrombocythemia, ulcerative colitis, and myeloid metaplasia with myelofibrosis and pain.

In some embodiments, the disease or cancer is a cancer mediated by ALK. In some embodiments, the disease or cancer is a cancer mediated by a genetically altered ALK. In some embodiments, the disease or cancer is a cancer mediated by a fusion protein comprising a fragment of a protein encoded by an ALK gene and a fragment of a protein which will form coiled-coil interaction to facilitate the protein dimerization or oligomerization. In some embodiments, the disease or cancer is a cancer mediated by a fusion protein comprising a fragment of a protein encoded by an ALK gene and a fragment of a protein encoded by a gene selected from the group consisting of NPM, EML4, TPR, TFG, ATIC, CLTC1, TPM4, MSN ALO17 and MYH9. In some embodiments, the fusion protein comprises a fragment of a protein encoded by an ALK gene and a fragment of a protein encoded by an EML4 gene. In some embodiments, the genetically altered ALK is an EML4-ALK fusion protein. In some embodiments, the EML4-ALK fusion protein is a wild-type protein. In some embodiments, the EML4-ALK fusion protein comprises at least one resistance mutation. In some embodiments, the EML4-ALK fusion protein comprises at least one mutation selected from the group consisting of L1196M, G1202R, D1203R, L1152P/R, F1174C/L/V, C1156Y, I1171N, G1123S, S1206Y, G1269S/A, and 1151T insertion.

In some embodiments, the fusion protein comprises a fragment of a protein encoded by an ALK gene and a fragment of a protein encoded by a NPM gene. In some embodiments, the genetically altered ALK is a NPM-ALK fusion protein. In some embodiments, the fusion protein comprises a fragment of a protein encoded by an ALK gene and a fragment of a protein encoded by a TPR gene. In some embodiments, the genetically altered ALK is a TPR-ALK fusion protein. In some embodiments, the TPR-ALK fusion protein is a wild-type protein. In some embodiments, the TPR-ALK fusion protein comprises at least one resistance mutation. In some embodiments, the TPR-ALK fusion protein comprises a L1196M point mutation.

In some embodiments, the disease or cancer is a cancer mediated by ALK. In some embodiments, the disease or cancer is a cancer mediated by a genetically altered ALK. In some embodiments, the disease or cancer is a cancer mediated by ALK having one or more point mutations. In some embodiments, the disease or cancer is a cancer mediated by ALK having one or more point mutations selected from the group consisting of R1050H, F1174C/I/L/S/V, F1245C/I/L/V, R1275L/Q, T1151M, M1166R, I1170N, I1170S, I1171N, I1183T, L1196M, A1200V, L1204F, L1240V, D1270G, Y1278S, R1192P, G1128A, G1286R, and T1343I. In some embodiments, the point mutation is a mutation at F1174. In some embodiments, the point mutation is a mutation of ALK at F1245. In some embodiments, the point mutation is a mutation of ALK at R1275.

In some embodiments, the disease or cancer is a cancer mediated by ROS1. In some embodiments, the disease or cancer is a cancer mediated by a genetically altered ROS1. In some embodiments, the disease or cancer is a cancer mediated by a fusion protein comprising a fragment of a protein encoded by an ROS1 gene and a fragment of a protein which will form coiled-coil interaction to facilitate the protein dimerization or oligomerization. In some embodiments, the disease or cancer is a cancer mediated by a fusion protein comprising a fragment of a protein encoded by a ROS1 gene and a fragment of a protein encoded by a gene selected from the group consisting of FIG, TPM3, SDC4, SLC34A2, CD74, EZR, and LRIG3. In some embodiments, the fusion protein comprises a fragment of a protein encoded by an ROS1 gene and a fragment of a protein encoded by a CD74 gene. In some embodiments, the genetically altered ROS1 is a CD74-ROS1 fusion protein. In some embodiments, the CD74-ROS1 fusion protein is a wild-type protein. In some embodiments, the CD74-ROS1 fusion protein comprises at least one resistance mutation. In some embodiments, the CD74-ROS1 fusion protein comprises a G2032R point mutation. In some embodiments, the CD74-ROS1 fusion protein comprises a L2026M point mutation. In some embodiments, the CD74-ROS1 fusion protein comprises a D2033N point mutation. In some embodiments, the genetically altered ROS1 is a SDC4-ROS1 fusion protein. In some embodiments, the SDC4-ROS1 fusion protein is a wild-type protein. In some embodiments, the SDC4-ROS1 fusion protein comprises at least one resistance mutation. In some embodiments, the SDC4-ROS1 fusion protein comprises a G2032R point mutation. In some embodiments, the genetically altered ROS1 is a SLC34A2-ROS1 fusion protein. In some embodiments, the SLC34A2-ROS1 fusion protein is a wild-type protein. In some embodiments, the SLC34A2-ROS1 fusion protein comprises at least one resistance mutation. In some embodiments, the SLC34A2-ROS1 fusion protein comprises a G2032R point mutation.

In some embodiments, the disease or cancer is a cancer mediated by TRKA. In some embodiments, the disease or cancer is a cancer mediated by a genetically altered TRKA. In some embodiments, the disease or cancer is a cancer mediated by a fusion protein comprising a fragment of a protein encoded by a TRKA gene and a fragment of a protein which will form coiled-coil interaction to facilitate the protein dimerization or oligomerization. In some embodiments, the disease or cancer is a cancer mediated by a fusion protein comprising a fragment of a protein encoded by a TRKA gene and a fragment of a protein encoded by a TPM3 gene. In some embodiments, the genetically altered TRKA is a TPM3-TRKA fusion protein. In some embodiments, the TPM3-TRKA fusion protein is a wild-type protein. In some embodiments, the TPM3-TRKA fusion protein comprises at least one resistance mutation.

In some embodiments, the disease or cancer is a cancer mediated by a fusion protein comprising a fragment of a protein encoded by a TRKA gene and a fragment of a protein encoded by a LMNA gene. In some embodiments, the genetically altered TRKA is a LMNA-TRKA fusion protein. In some embodiments, the LMNA-TRKA fusion protein is a wild-type protein. In some embodiments, the LMNA-TRKA fusion protein comprises at least one resistance mutation. In some embodiments, the LMNA-TRKA fusion protein is a wild-type protein. In some embodiments, the LMNA-TRKA fusion protein comprises at least one resistance mutation comprising a G595R point mutation.

In some embodiments, the disease or cancer is a cancer mediated by TRKB. In some embodiments, the disease or cancer is a cancer mediated by a genetically altered TRKB. In some embodiments, the disease or cancer is a cancer mediated by a fusion protein comprising a fragment of a protein encoded by a TRKB gene and a fragment of a protein which will form coiled-coil interaction to facilitate the protein dimerization or oligomerization. In some embodiments, the disease or cancer is a cancer mediated by a fusion protein comprising a fragment of a protein encoded by a TRKB gene and a fragment of a protein encoded by a QKI gene or TEL gene. In some embodiments, the disease or cancer is a cancer mediated by a fusion protein comprising a fragment of a protein encoded by a TRKB gene and a fragment of a protein encoded by a QKI gene. In some embodiments, the disease or cancer is a cancer mediated by a fusion protein comprising a fragment of a protein encoded by a TRKB gene and a fragment of a protein encoded by a TEL gene. In some embodiments, the genetically altered TRKB is a QKI-TRKB or TEL-TRKB fusion protein. In some embodiments, the genetically altered TRKB is a TEL-TRKB fusion protein. In some embodiments, the genetically altered TRKB is a QKI-TRKB fusion protein. In some embodiments, the QKI-TRKB or TEL-TRKB fusion protein is a wild-type protein. In some embodiments, the QKI-TRKB fusion protein is a wild-type protein. In some embodiments, the TEL-TRKB fusion protein is a wild-type protein. In some embodiments, the QKI-TRKB or TEL-TRKB fusion protein comprises at least one resistance mutation. In some embodiments, the QKI-TRKB fusion protein comprises at least one resistance mutation. In some embodiments, the TEL-TRKB fusion protein comprises at least one resistance mutation. In some embodiments, the TEL-TRKB fusion protein comprises a G639R point mutation.

In some embodiments, the disease or cancer is a cancer mediated by TRKC. In some embodiments, the disease or cancer is a cancer mediated by a genetically altered TRKC. In some embodiments, the disease or cancer is a cancer mediated by a fusion protein comprising a fragment of a protein encoded by a TRKC gene and a fragment of a protein which will form coiled-coil interaction to facilitate the protein dimerization or oligomerization. In some embodiments, the disease or cancer is a cancer mediated by a fusion protein comprising a fragment of a protein encoded by a TRKC gene and a fragment of a protein encoded by an ETV6 gene. In some embodiments, the genetically altered TRKC is an ETV6-TRKC fusion protein. In some embodiments, the ETV6-TRKC fusion protein is a wild-type protein. In some embodiments, the ETV6-TRKC fusion protein comprises at least one resistance mutation. In some embodiments, the ETV6-TRKC fusion protein comprises a G623R point mutation.

In some embodiments, the disease or cancer is a cancer mediated by JAK1, JAK2 or JAK3. In some embodiments, the disease or cancer is a cancer mediated by a genetically altered JAK2. In some embodiments, the disease or cancer is a cancer mediated by a fusion protein comprising a fragment of a protein encoded by a JAK2 gene and a fragment of a protein which will form coiled-coil interaction to facilitate the protein dimerization or oligomerization. In some embodiments, the disease or cancer is a cancer mediated by a fusion protein comprising a fragment of a protein encoded by a JAK2 gene and a fragment of a protein encoded by a TEL or PCM1 gene. In some embodiments, the genetically altered JAK2 is a TEL-JAK2 fusion protein. In some embodiments, the genetically altered JAK2 is a PCM1-JAK2 fusion protein. In some embodiments, the disease or cancer is a cancer mediated by point mutation(s) of JAK2. In some embodiments, the genetically altered JAK2 has the JAK2V617F mutation.

In some embodiments, the disease is pain. In some embodiments, the disease is pain mediated by TRKA, TRKB or TRKC. In some embodiments, the pain is mediated by TRKA. In some embodiments, the pain is mediated by TRKB. In some embodiments, the pain is mediated by TRKC. In some embodiments, the disease is selected from the group consisting of psoriasis, rheumatoid arthritis, polycythemia vera, essential thrombocythemia, ulcerative colitis, and myeloid metaplasia with myelofibrosis. In some embodiments, the disease or cancer is a cancer exhibiting bypass resistance.

In some embodiments, the disease or cancer is a cancer mediated by FGR. In some embodiments, the disease or cancer is a cancer mediated by a genetically altered FGR. In some embodiments, the fusion protein comprises a fragment of a protein encoded by a FGR gene and a fragment of a protein encoded by a WASF2 gene. In some embodiments, the genetically altered FGR is a WASF2-FGR fusion protein. In some embodiments, the WASF2-FGR fusion protein is a wild-type protein. In some embodiments, the WASF2-FGR fusion protein comprises at least one resistance mutation.

In some embodiments, the cancer is selected from the group consisting of ALCL, NSCLC, neuroblastoma, inflammatory myofibroblastic tumor, adult renal cell carcinoma, pediatric renal cell carcinoma, breast cancer, colonic adenocarcinoma, glioblastoma, glioblastoma multiforme and anaplastic thyroid cancer.

In some embodiments, the cancer is selected from the group consisting of glioblastoma, glioblastoma multiforme, NSCLC, cholangiocarcinoma, ovarian cancer, gastric adenocarcinoma, colorectal cancer, inflammatory myofibroblastic tumor, angiosarcoma, and epithelioid hemangioendothelioma.

In some embodiments, the cancer is selected from the group consisting of glioblastoma, glioblastoma multiforme, NSCLC, cholangiocarcinoma, intrahepatic cholangiocarcinoma, colorectal cancer, thyroid papillary cancer, spitzoid neoplasms, sarcoma, astrocytoma, brain lower grade glioma, secretory breast carcinoma, mammary analogue carcinoma, breast cancer, acute myeloid leukemia, congenital mesoblastic nephroma, congenital fibrosarcomas, Ph-like acute lymphoblastic leukemia, colon adenocarcinoma, thyroid carcinoma, skin cutaneous melanoma, head and neck squamous cell carcinoma and pediatric glioma.

In some embodiments, the cancer is selected from the group consisting of NSCLC, neuroblastoma, breast cancer, colon cancer and prostate cancer. In some embodiments, the cancer is NSCLC. In some embodiments, the cancer is neuroblastoma. In some embodiments, the cancer is colorectal cancer.

In some embodiments, the patient has been previously treated with a cancer therapeutic. In some embodiments, the patient has been previously treated with a cancer therapeutic, and the cancer has developed resistance to the cancer therapeutic. In some embodiments, the resistance is a primary intrinsic resistance. In some embodiments, the resistance is an acquired resistance from mutation(s). In some embodiments, the resistance is a bypass resistance. In some embodiments, the resistance is an EMT-based resistance.

Additional embodiments, features, and advantages of the disclosure will be apparent from the following detailed description and through practice of the disclosure. The compounds of the present disclosure can be described as embodiments in any of the following enumerated clauses. It will be understood that any of the embodiments described herein can be used in connection with any other embodiments described herein to the extent that the embodiments do not contradict one another.

1. A method of treating disease in a patient comprising, administering to the patient a therapeutically effective amount of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one, or a pharmaceutically acceptable salt thereof.
2. The method of clause 1, wherein the disease is mediated by a tyrosine or serine/threonine kinase selected from the group consisting of ALK, ROS1, TRKA, TRKB, TRKC, JAK2, SRC, FYN, LYN, YES, FGR, FAK, and ARK5, and combinations thereof; or ALK, ROS1, TRKA, TRKB, TRKC, JAK2, SRC, FAK, and ARK5, and combinations thereof.
3. The method of clause 1, wherein the disease is mediated by a receptor tyrosine kinase.
4. The method of clause 3, wherein the receptor tyrosine kinase is selected from the group consisting of ALK, ROS1, TRKA, TRKB and TRKC.
5. The method of clause 1, wherein the disease is mediated by a non-receptor kinase.
6. The method of clause 5, wherein the non-receptor kinase is JAK2, FYN, LYN, YES, FGR, SRC, FAK or ARK5, including the non-receptor tyrosine kinase JAK2, FYN, LYN, YES, FGR, SRC or FAK, or the non-receptor serine/threonine kinase ARK5.

7. The method of any one of clauses 1 to 6, wherein the disease is selected from the group consisting of cancer, psoriasis, rheumatoid arthritis, polycythemia vera, essential thrombocythemia, ulcerative colitis, and myeloid metaplasia with myelofibrosis and pain.
8. The method of any one of clauses 1 to 6, wherein the disease is cancer.
9. The method of any one of clauses 1 to 4, 7 or 8, wherein the disease is a cancer mediated by ALK.
10. The method of any one of clauses 1 to 4, 7 or 8, wherein the disease is a cancer mediated by a genetically altered ALK.
11. The method of any one of clauses 1 to 4, 7 or 8, wherein the disease is a cancer mediated by a fusion protein comprising a fragment of a protein encoded by an ALK gene and a fragment of a protein encoded by a gene selected from the group consisting of NPM, EML4, TPR, TFG, ATIC, CLTC1, TPM4, MSN ALO17 and MYH9.
12. The method of clause 11, wherein the fusion protein comprises a fragment of a protein encoded by an ALK gene and a fragment of a protein encoded by an EML4 gene.
13. The method of clause 10, wherein the genetically altered ALK is an EML4-ALK fusion protein.
14. The method of clause 13, wherein the EML4-ALK fusion protein is a wild-type protein.
15. The method of clause 13, wherein the EML4-ALK fusion protein comprises at least one resistance mutation.
16. The method of clause 13, wherein the EML4-ALK fusion protein comprises at least one mutation selected from the group consisting of L1196M, G1202R, D1203R, L1152P/R, F1174C/L/V, C1156Y, I1171N, G1123S, S1206Y, G1269S/A, and 1151T insertion.
17. The method of clause 16, wherein the mutation is L1196M.
18. The method of clause 16, wherein the mutation is G1202R.
19. The method of clause 16, wherein the mutation is L1152P.
20. The method of clause 16, wherein the mutation is F1174C.
21. The method of clause 16, wherein the mutation is C1156Y.
22. The method of clause 16, wherein the mutation is I1171N.
23. The method of clause 16, wherein the mutation is G1269S.
24. The method of clause 16, wherein the mutation is 1151T insertion.
25. The method of clause 11, wherein the fusion protein comprises a fragment of a protein encoded by an ALK gene and a fragment of a protein encoded by a NPM gene.
26. The method of clause 10, wherein the genetically altered ALK is a NPM-ALK fusion protein.
27. The method of clause 11, wherein the fusion protein comprises a fragment of a protein encoded by an ALK gene and a fragment of a protein encoded by a TPR gene.
28. The method of clause 10, wherein the genetically altered ALK is a TPR-ALK fusion protein.
29. The method of clause 28, wherein the TPR-ALK fusion protein is a wild-type protein.
30. The method of clause 28, wherein the TPR-ALK fusion protein comprises at least one resistance mutation.
31. The method of clause 28, wherein the TPR-ALK fusion protein comprises a L1196M point mutation.
32. The method of any one of clauses 1 to 4, wherein the disease is a cancer mediated by ALK having one or more point mutations.

The method of any one of claims 1 to 4 or 32, wherein the disease is a cancer mediated by ALK having one or more point mutations selected from the group consisting of R1050H, F1174C/I/L/S/V, F1245C/I/L/V, R1275L/Q, T1151M, M1166R, I1170N, I1170S, I1171N, I1183T, L1196M, A1200V, L1204F, L1240V, D1270G, Y1278S, R1192P, G1128A, G1286R, and T1343I.
34. The method of any one of clauses 1 to 4, 32 or 33, wherein the point mutation is a mutation of ALK at F1174.
35. The method of any one of clauses 1 to 4, 32 or 33, wherein the point mutation is a mutation of ALK at F1245.
36. The method of any one of clauses 1 to 4, 32 or 33, wherein the point mutation is a mutation of ALK at R1275.
37. The method of any one of clauses 9 to 36, wherein the cancer is selected from the group consisting of ALCL, NSCLC, neuroblastoma, inflammatory myofibroblastic tumor, adult renal cell carcinoma, pediatric renal cell carcinoma, breast cancer, colonic adenocarcinoma, glioblastoma, glioblastoma multiforme and anaplastic thyroid cancer.
38. The method of any one of clauses 9 to 37, wherein the cancer is NSCLC.
39. The method of any one of clauses 1 to 4, 7 or 8, wherein the disease is a cancer mediated by ROS1.
40. The method of any one of clauses 1 to 4, 7 or 8, wherein the disease is a cancer mediated by a genetically altered ROS1.
41. The method of any one of clauses 1 to 4, 7 or 8, wherein the disease is a cancer mediated by a fusion protein comprising a fragment of a protein encoded by an ROS1 gene and a fragment of a protein encoded by a gene selected from the group consisting of FIG, TPM3, SDC4, SLC34A2, CD74, EZR, and LRIG3.
42. The method of clause 41, wherein the fusion protein comprises a fragment of a protein encoded by an ROS1 gene and a fragment of a protein encoded by a CD74 gene.
43. The method of clause 40, wherein the genetically altered ROS1 is a CD74-ROS1 fusion protein.
44. The method of clause 43, wherein the CD74-ROS1 fusion protein is a wild-type protein.
45. The method of clause 43, wherein the CD74-ROS1 fusion protein comprises at least one resistance mutation.
46. The method of clause 43, wherein the CD74-ROS1 fusion protein comprises a G2032R, L2026M or D2033N point mutation.
47. The method of clause 40, wherein the genetically altered ROS1 is a SDC4-ROS1 fusion protein.
48. The method of clause 47, wherein the SDC4-ROS1 fusion protein is a wild-type protein.
49. The method of clause 47, wherein the SDC4-ROS1 fusion protein comprises at least one resistance mutation.
50. The method of clause 47, wherein the SDC4-ROS1 fusion protein comprises a G2032R point mutation.

51. The method of clause 40, wherein the genetically altered ROS1 is a SLC34A2-ROS1 fusion protein.
52. The method of clause 51, wherein the SLC34A2-ROS1 fusion protein is a wild-type protein.
53. The method of clause 51, wherein the SLC34A2-ROS1 fusion protein comprises at least one resistance mutation.
54. The method of clause 51, wherein the SLC34A2-ROS1 fusion protein comprises a G2032R point mutation.
55. The method of any one of clauses 1 to 4, 7, 8 or 39 to 54, wherein the cancer is selected from the group consisting of glioblastoma, glioblastoma multiforme, NSCLC, cholangiocarcinoma, ovarian cancer, gastric adenocarcinoma, colorectal cancer, inflammatory myofibroblastic tumor, angiosarcoma, and epithelioid hemangioendothelioma.
56. The method of any one of clauses 1 to 4, 7, 8 or 39 to 55, wherein the cancer is NSCLC.
57. The method of any one of clauses 1 to 4, 7 or 8, wherein the disease is a cancer mediated by TRKA.
58. The method of any one of clauses 1 to 4, 7 or 8, wherein the disease is a cancer mediated by a genetically altered TRKA.
59. The method of any one of clauses 1 to 4, 7 or 8, wherein the disease is a cancer mediated by a fusion protein comprising a fragment of a protein encoded by a TRKA gene and a fragment of a protein encoded by a TPM3 gene or LMNA gene.
60. The method of clause 58, wherein the genetically altered TRKA is a TPM3-TRKA or LMNA-TRKA fusion protein.
61. The method of clause 60, wherein the TPM3-TRKA or LMNA-TRKA fusion protein is a wild-type protein.
62. The method of clause 60, wherein the TPM3-TRKA or LMNA-TRKA fusion protein comprises at least one resistance mutation, including a LMNA-TRKA fusion protein comprising a G595R point mutation.
63. The method of any one of clauses 1 to 4, 7 or 8, wherein the disease is a cancer mediated by TRKB.
64. The method of any one of clauses 1 to 4, 7 or 8, wherein the disease is a cancer mediated by a genetically altered TRKB, including QKI-TRKB or TEL-TRKB, including TEL-TRKB comprising a G639R point mutation.
65. The method of any one of clauses 1 to 4, 7 or 8, wherein the disease is a cancer mediated by TRKC.
66. The method of any one of clauses 1 to 4, 7 or 8, wherein the disease is a cancer mediated by a genetically altered TRKC, including a ETV6-TRKC fusion protein, including a genetically altered ETV6-TRKC fusion protein, including a ETV6-TRKC fusion protein comprising a G326R point mutation.
67. The method of any one of clauses 1 to 4, 7, 8 or 57 to 66, wherein the cancer is selected from the group consisting of glioblastoma, glioblastoma multiforme, NSCLC, cholangiocarcinoma, intrahepatic cholangiocarcinoma, colorectal cancer, thyroid papillary cancer, spitzoid neoplasms, sarcoma, astrocytoma, brain lower grade glioma, secretory breast carcinoma, mammary analogue carcinoma, breast cancer, acute myeloid leukemia, congenital mesoblastic nephroma, congenital fibrosarcomas, Ph-like acute lymphoblastic leukemia, colon adenocarcinoma, thyroid carcinoma, skin cutaneous melanoma, head and neck squamous cell carcinoma and pediatric glioma.
68. The method of any one of clauses 1 to 4, 7, 8 or 57 to 67, wherein the cancer is NSCLC.
69. The method of any one of clauses 1 to 4, 7, 8 or 57 to 67, wherein the cancer is colorectal cancer.
70. The method of any one of clauses 1 to 4, 7 or 8, wherein the disease is a cancer mediated by JAK1, JAK2 or JAK3.
71. The method of any one of clauses 1 to 4, 7 or 8, wherein the disease is a cancer mediated by a genetically altered JAK2.
72. The method of any one of clauses 1 to 4, 7 or 8, wherein the disease is a cancer mediated by a fusion protein comprising a fragment of a protein encoded by a JAK2 gene and a fragment of a protein encoded by a TEL or PCM1 gene.
73. The method of clause 71, wherein the genetically altered JAK2 is a TEL-JAK2 fusion protein.
74. The method of clause 71, wherein the genetically altered JAK2 is a PCM1-JAK2 fusion protein.
75. The method of clause 71, wherein the genetically altered JAK2 comprises a V617F point mutation.
76. The method of any one of clauses 1 to 4, 7 or 8, wherein the disease is a cancer mediated by SRC.
77. The method of clause 76, wherein the cancer is selected from the group consisting of glioblastoma, glioblastoma multiforme, NSCLC, cholangiocarcinoma, intrahepatic cholangiocarcinoma, colorectal cancer, thyroid papillary cancer, spitzoid neoplasms, sarcoma, astrocytoma, brain lower grade glioma, secretory breast carcinoma, mammary analogue carcinoma, breast cancer, acute myeloid leukemia, congenital mesoblastic nephroma, congenital fibrosarcomas, Ph-like acute lymphoblastic leukemia, colon adenocarcinoma, thyroid carcinoma, skin cutaneous melanoma, head and neck squamous cell carcinoma and pediatric glioma.
78. The method of any one of clauses 1 to 4, wherein the disease is pain.
79. The method of any one of clauses 1 to 4, wherein the disease is pain mediated by TRKA, TRKB or TRKC.
80. The method of clause 79, wherein the pain is mediated by TRKA.
81. The method of clause 79, wherein the pain is mediated by TRKB.
82. The method of clause 79, wherein the pain is mediated by TRKC.
83. The method of any one of clauses 1 to 3, 5 or 6 wherein the disease is selected from the group consisting of psoriasis, rheumatoid arthritis, polycythemia vera, essential thrombocythemia, ulcerative colitis, and myeloid metaplasia with myelofibrosis.
84. The method of any one of clauses 1, 5, 6 or 8, wherein the disease is a cancer exhibiting bypass resistance.
85. A method of treating cancer in a patient previously shown to express a genetically altered tyrosine or serine/threonine kinase comprising, administering to the patient a therapeutically effective amount of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one, or a pharmaceutically acceptable salt thereof.
86. The method of clause 85, wherein the genetically altered tyrosine kinase is selected from the group consisting of a genetically altered ALK, genetically altered ROS1, genetically altered TRK and genetically altered JAK.

87. The method of clause 86, wherein the genetically altered ALK is a fusion protein comprising a fragment of a protein encoded by an ALK gene and a fragment of a protein encoded by a gene selected from the group consisting of NPM, EML4, TPR, TFG, ATIC, CLTC1, TPM4, MSN ALO17 and MYH9.
88. The method of clause 87, wherein the fusion protein comprises a fragment of a protein encoded by an ALK gene and a fragment of a protein encoded by an EML4 gene.
89. The method of clause 86, wherein the genetically altered ALK is an EML4-ALK fusion protein.
90. The method of clause 89, wherein the EML4-ALK fusion protein is a wild-type protein.
91. The method of clause 89, wherein the EML4-ALK fusion protein comprises at least one resistance mutation.
92. The method of clause 89, wherein the EML4-ALK fusion protein comprises at least one mutation selected from the group consisting of L1196M, G1202R, D1203R, L1152P/R, F1174C/L/V, C1156Y, I1171N, G1123S, S1206Y, G1269S/A, and 1151T insertion.
93. The method of clause 87, wherein the fusion protein comprises a fragment of a protein encoded by an ALK gene and a fragment of a protein encoded by a NPM gene.
94. The method of clause 86, wherein the genetically altered ALK is a NPM-ALK fusion protein.
95. The method of clause 87, wherein the fusion protein comprises a fragment of a protein encoded by an ALK gene and a fragment of a protein encoded by a TPR gene.
96. The method of clause 86, wherein the genetically altered ALK is a TPR-ALK fusion protein.
97. The method of clause 96, wherein the TPR-ALK fusion protein is a wild-type protein.
98. The method of clause 96, wherein the TPR-ALK fusion protein comprises at least one resistance mutation.
99. The method of clause 98, wherein the TPR-ALK fusion protein comprises a L1196M point mutation.
100. The method of any one of clauses 85 to 99, wherein the cancer exhibits a bypass resistance mechanism.
101. The method of clause 100, wherein the bypass resistance mechanism is mediated by SRC.
102. The method of any one of clauses 85 to 101, wherein the cancer is selected from the group consisting of ALCL, NSCLC, neuroblastoma, inflammatory myofibroblastic tumor, adult renal cell carcinoma, pediatric renal cell carcinoma, breast cancer, colonic adenocarcinoma, glioblastoma, glioblastoma multiforme and anaplastic thyroid cancer.
103. The method of any one of clauses 85 to 102, wherein the cancer is NSCLC.
104. The method of clause 86, wherein the genetically altered ROS1 is a fusion protein comprising a fragment of a protein encoded by an ROS1 gene and a fragment of a protein encoded by a gene selected from the group consisting of FIG, TPM3, SDC4, SLC34A2, CD74, EZR, and LRIG3.
105. The method of clause 104, wherein the fusion protein comprises a fragment of a protein encoded by an ROS1 gene and a fragment of a protein encoded by a CD74 gene.
106. The method of clause 104, wherein the genetically altered ROS1 is a CD74-ROS1 fusion protein.
107. The method of clause 106, wherein the CD74-ROS1 fusion protein is a wild-type protein.
108. The method of clause 106, wherein the CD74-ROS1 fusion protein comprises at least one resistance mutation.
109. The method of clause 106, wherein the CD74-ROS1 fusion protein comprises a G2032R, L2026M or D2033N point mutation.
110. The method of clause 105, wherein the genetically altered ROS1 is a SDC4-ROS1 fusion protein.
111. The method of clause 110, wherein the SDC4-ROS1 fusion protein is a wild-type protein.
112. The method of clause 110, wherein the SDC4-ROS1 fusion protein comprises at least one resistance mutation.
113. The method of clause 110, wherein the SDC4-ROS1 fusion protein comprises a G2032R point mutation.
114. The method of clause 105, wherein the genetically altered ROS1 is a SLC34A2-ROS1 fusion protein.
115. The method of clause 114, wherein the SLC34A2-ROS1 fusion protein is a wild-type protein.
116. The method of clause 114, wherein the SLC34A2-ROS1 fusion protein comprises at least one resistance mutation.
117. The method of clause 114, wherein the SLC34A2-ROS1 fusion protein comprises a G2032R point mutation.
118. The method of any one of clauses 85, 86 or 104 to 117, wherein the cancer is selected from the group consisting of glioblastoma, glioblastoma multiforme, NSCLC, cholangiocarcinoma, ovarian cancer, gastric adenocarcinoma, colorectal cancer, inflammatory myofibroblastic tumor, angiosarcoma, and epithelioid hemangioendothelioma.
119. The method of any one of clauses 85, 86 or 104 to 118, wherein the cancer is NSCLC.
120. The method of clause 86, wherein the genetically altered TRK is a fusion protein comprising a fragment of a protein encoded by a TRKA gene and a fragment of a protein encoded by a TPM3 gene or LMNA gene.
121. The method of clause 86, wherein the genetically altered TRK is a TPM3-TRKA or LMNA-TRKA fusion protein.
122. The method of clause 121, wherein the TPM3-TRKA or LMNA-TRKA fusion protein is a wild-type protein.
123. The method of clause 121, wherein the TPM3-TRKA or LMNA-TRKA fusion protein comprises at least one resistance mutation.
124. The method of any one of clauses 86, 87 or 120 to 123, wherein the cancer is selected from the group consisting of glioblastoma, glioblastoma multiforme, NSCLC, cholangiocarcinoma, intrahepatic cholangiocarcinoma, colorectal cancer, thyroid papillary cancer, spitzoid neoplasms, sarcoma, astrocytoma, brain lower grade glioma, secretory breast carcinoma, mammary analogue carcinoma, breast cancer, acute myeloid leukemia, congenital mesoblastic nephroma, congenital fibrosarcomas, Ph-like acute lymphoblastic leukemia, colon adenocarcinoma, thyroid carcinoma, skin cutaneous melanoma, head and neck squamous cell carcinoma and pediatric glioma.
125. The method of any one of clauses 85, 86 or 120 to 123, wherein the cancer is NSCLC.
126. The method of any one of clauses 79, 80 or 120 to 123, wherein the cancer is colorectal cancer.
127. The method of clause 86, wherein the genetically altered JAK is fusion protein comprising a fragment of a protein encoded by a JAK2 gene and a fragment of a protein encoded by a TEL or PCM1 gene.

128. The method of clause 86, wherein the genetically altered JAK is a TEL-JAK2 fusion protein.

129. The method of clause 86, wherein the genetically altered JAK is a PCM1-JAK2 fusion protein.

130. A method of treating cancer in a patient comprising;
   i. identifying a genetically altered tyrosine or serine/threonine kinase in the patient, and
   ii. administering to the patient a therapeutically effective amount of (7S,13R)-11-fluoro-7,13-dimethyl-6,7,13,14-tetrahydro-1,15-ethenopyrazolo[4,3-f][1,4,8,10]benzoxatriaza-cyclotridecin-4(5H)-one, or a pharmaceutically acceptable salt thereof.

131. The method of clause 130, wherein the step of identifying comprises subjecting a patient sample to a test selected from the group consisting of FISH, IHC, PCR and gene sequencing.

132. A method of identifying a patient for treatment with (7S,13R)-11-fluoro-7,13-dimethyl-6,7,13,14-tetrahydro-1,15-ethenopyrazolo[4,3-J][1,4,8,10]benzoxatriaza-cyclotridecin-4(5H)-one, or a pharmaceutically acceptable salt thereof, comprising diagnosing the patient with a cancer mediated by a genetically altered tyrosine or serine/threonine kinase.

133. The method of clause 132, wherein the diagnosing comprises subjecting a patient sample to a biological test or biological assay selected from the group consisting of FISH, IHC, PCR and gene sequencing.

134. The method of any one of the preceding clauses, wherein the patient has been previously treated with a cancer therapeutic.

135. The method of any one of the preceding clauses, wherein the patient has been previously treated with a cancer therapeutic, and the cancer has developed resistance to the cancer therapeutic.

136. The method of clause 129, wherein the resistance is an acquired resistance.

137. The method of clause 129, wherein the resistance is a bypass resistance.

138. Use of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one, or a pharmaceutically acceptable salt thereof, in the preparation of a medicament for the treatment of a disease in a patient.

139. Use of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one, or a pharmaceutically acceptable salt thereof, for treating cancer in a patient.

140. Use of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one, or a pharmaceutically acceptable salt thereof, for treating pain in a patient.

141. Use of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one, or a pharmaceutically acceptable salt thereof, for treating cancer in a patient previously shown to express a genetically altered tyrosine or serine/threonine kinase.

142. Use of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one, or a pharmaceutically acceptable salt thereof, for treating cancer in a patient, wherein the patient has been previously treated with a cancer therapeutic, and the cancer has developed resistance to the cancer therapeutic.

143. Use of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one, or a pharmaceutically acceptable salt thereof, for treating cancer in a patient previously shown to express a genetically altered tyrosine or serine/threonine kinase, wherein the patient has been previously treated with a cancer therapeutic, and the cancer has developed resistance to the cancer therapeutic.

BRIEF DESCRIPTION OF THE DRAWINGS

FIGS. 1A-1B show the effect of Compound 1 on apoptosis of Karpas-299 cells. FIG. 1A shows Karpas-299 cell apoptosis after incubation in various concentrations of Compound 1 for 48 hours; FIG. 1B shows Karpas-299 cells were collected, lysed and analyzed by SDS-PAGE and immunoblotted with PARP and Actin antibodies.

FIG. 3 shows results after 4 hour exposure to Compound 1 at 0 nM, 30 nM, 100 nM, 300 nM and 1000 nM; FIG. 3 shows results after 24 hour exposure to Compound 1 at 0 nM, 30 nM, 100 nM, 300 nM and 1000 nM.

FIG. 4 shows results after exposure to Compound 1 at 0 nM, 30 nM, 100 nM, 300 nM and 1000 nM; FIG. 4 shows results after exposure to crizotinib at 0 nM, 30 nM, 100 nM, 300 nM and 1000 nM.

DETAILED DESCRIPTION

Figure 2:
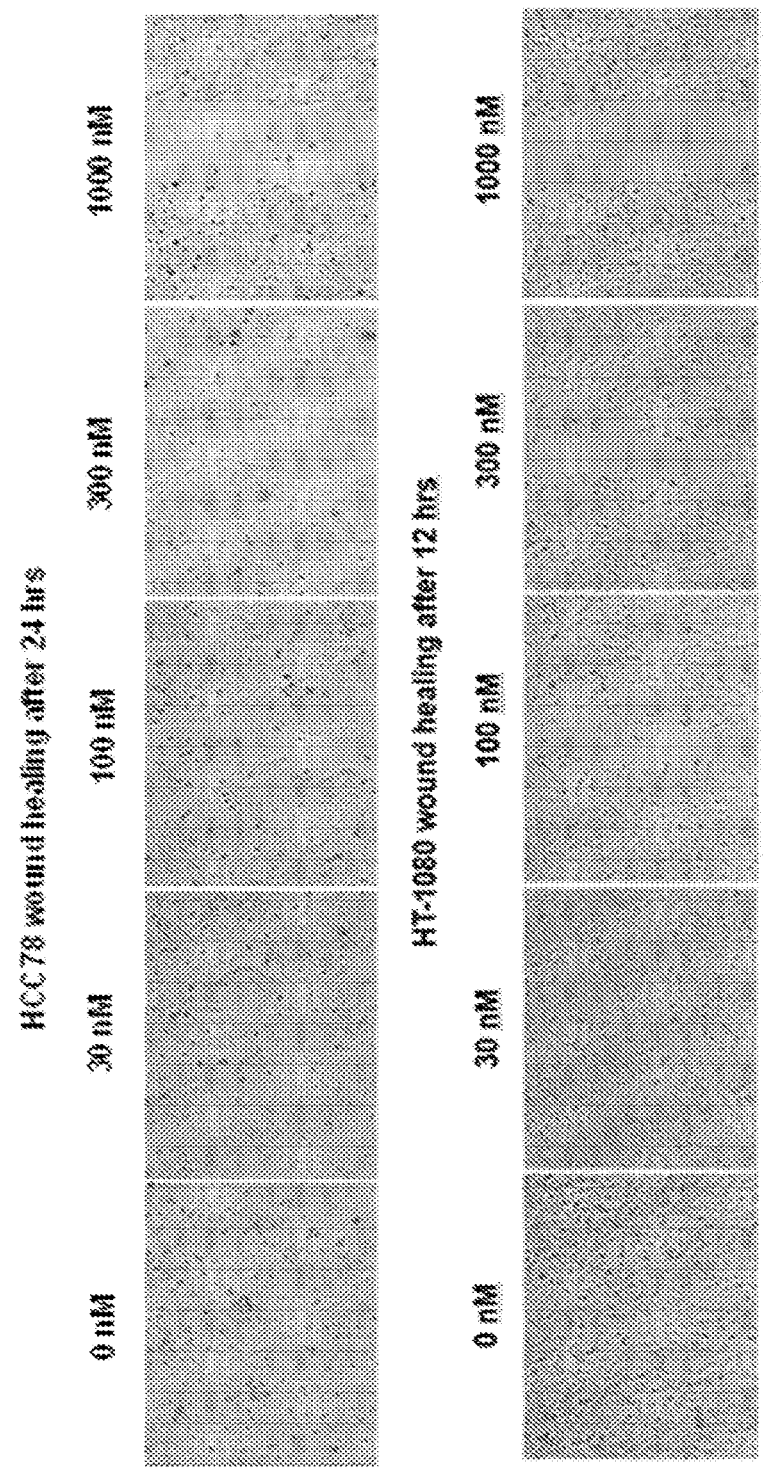
FIG. 2 shows the effect of Compound 1 on wound healing in HCC78 and HT-1080 cells.

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Definitions

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$. Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like. Illustrative examples of cycloalkyl groups shown in graphical representations include the following entities, in the form of properly bonded moieties:

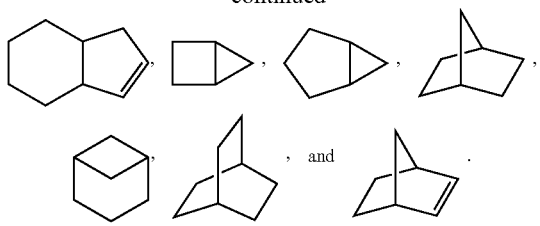

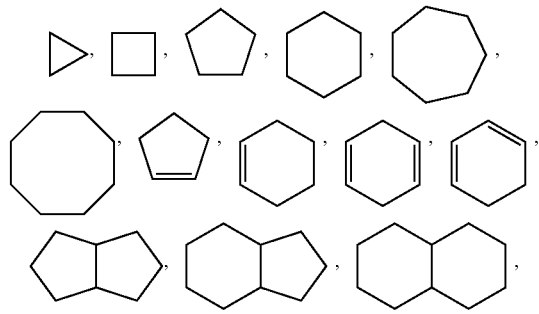

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like. Illustrative examples of heterocycloalkyl groups shown in graphical representations include the following entities, in the form of properly bonded moieties:

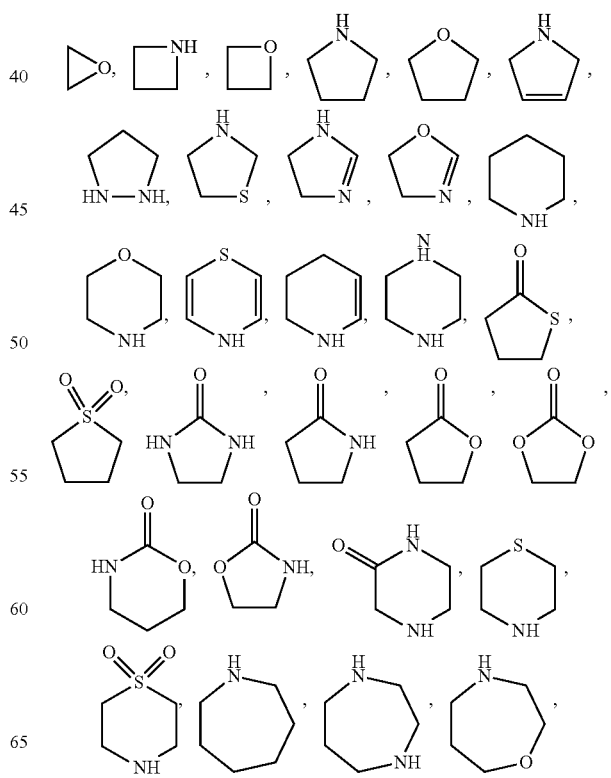

-continued

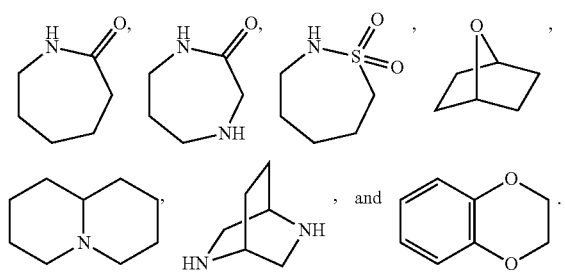

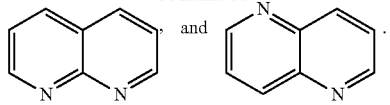

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

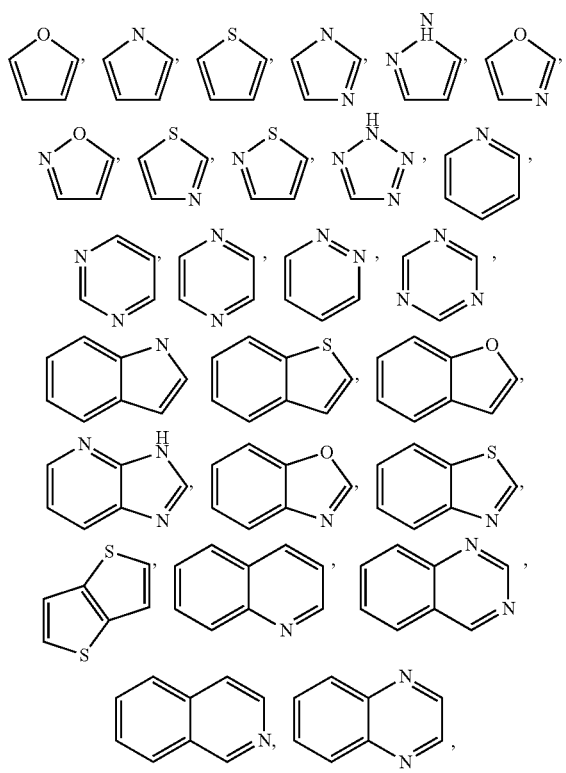

As used herein, "hydroxy" or ""hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

The term "oxo" represents a carbonyl oxygen. For example, a cyclopentyl substituted with oxo is cyclopentanone.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula I that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The disclosure also relates to pharmaceutically acceptable prodrugs of the compounds of Formula I, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present disclosure also relates to pharmaceutically active metabolites of compounds of Formula I, and uses of such metabolites in the methods of the disclosure. A "pharmaceutically active metabolite" means a pharmacologically active product of metabolism in the body of a compound of Formula I or salt thereof. Prodrugs and active metabolites of a compound may be determined using routine techniques known or available in the art. See, e.g., Bertolini et al., J. Med. Chem. 1997, 40, 2011-2016; Shan et al., J. Pharm. Sci. 1997, 86 (7), 765-767; Bagshawe, Drug Dev. Res. 1995, 34, 220-230; Bodor, Adv. Drug Res. 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

As used herein, the term "genetically altered" refers to a permanent alteration in the DNA sequence that makes up a gene that can result in a change in the protein sequence encoded by the gene. A gene that is "genetically altered" as described herein, can possess changes in DNA sequence, and/or protein sequence encoded by the DNA sequence, that range in size; for example, a single nucleotide (a.k.a. a single nucleotide polymorphism, SNP or point mutation), a multiple nucleotide polymorphism (MNPs), a large segment of a chromosome that includes multiple genes, such as a gene fusion, and the like. Examples of gene fusions include, but are not limited to, those which are the result of a chromosomal inversion in which a portion of a chromosomal DNA encoding one or more genes rearranges to provide a fusion of two genes not ordinarily in communication in the DNA sequence, such as EML4-ALK (see for example, Soda, M. et al., Nature, 2007, 448, 561-567), those which are the result of a deletion in the DNA sequence (an "interstitial deletion") in which part of a DNA sequence of a chromosome is deleted to provide a fusion of two genes not ordinarily in communication in the DNA sequence, such as TMPRSS2-ERG (see for example, Yu J. et al., Cancer Cell, 2010, 17, 5, 443-54), or those which are the result of a translocation in which a portion of chromosomal DNA is spliced and inserted into the same or a different chromosome to provide a fusion of two genes not ordinarily in communication in the DNA sequence, such as BCR-ABL (see for example, Advani, A. S. et al. Leukemia Research, 2002, 26, 8, 713-720). One of skill in the art will readily appreciate that such gene fusions can be found in multiple variants depending on the individual in which the gene fusion has occurred, and each of such variants is contemplated by the methods described herein.

A "genetically altered" gene, or the protein encoded by such gene, can occur as hereditary mutations which can be inherited from a parent and are sometimes referred to as germline mutations, or a "genetically altered" gene, or the protein encoded by such gene, can occur as an acquired (or somatic) mutation that occurs at some point during a person's life. In some instances, a "genetically altered" gene can be described as a de novo (new) mutation, and can be either hereditary or somatic. It will be further understood that "genetically altered" can refer to a situation in which more than one of the changes in DNA sequence described herein can occur in a patient simultaneously, such as a SNP (or point mutation) and a translocation. Such situations can arise from, but are not solely the result of, so-called "acquired resistance" in which a patient having been treated with a kinase inhibitor can develop a mutation in the DNA sequence that reduces the effectiveness of the treatment. Non-limiting examples of such acquired resistance mutations include the point mutation L1196M, G1202R, L1152P, F1174C, C1156Y, I1171N, G1269S, and the 1151T insertion that occur in the EML4-ALK gene fusion.

As used herein, the term "intrinsic resistance" refers to the pre-existing resistance of disease cells, especially cancer cells, to drug treatment, especially chemotherapy treatment. It will be appreciated that intrinsic resistance can result in resistance of the cells to a single drug, a small group of structurally related drugs, or a several drugs of differing chemical structure (so-called "multidrug resistance" or "MDR"). (Monti, E. 2007. Molecular Determinants of Intrinsic Multidrug Resistance in Cancer Cells and Tumors In B. Teicher (Ed.), Cancer Drug Resistance (pp. 241-260). Totowa, New Jersey: Humana Press Inc.). It will be appreciated that intrinsic resistance can be the result of one or more host-related factors and/or the genetic make-up of the cells. Such factors include but are not limited to immunomodulation; pharmacogenetic factors such as failure to achieve optimal serum drugs levels due to altered ADME or low tolerance to drug-induced side effects; restricted drug access to the tumor site; and microenvironmental cues. Such genetic make-up factors include, but are not limited to altered expression of drug transporters; qualitative alterations of drug target(s); quantitative alterations of drug target(s); changes in intracellular drug handling/metabolism; changes in DNA repair activities, and alteration in apoptotic pathways. (Gottesman, M. M., Annu. Rev. Med., 2002, 53, 516-527).

As used herein, the term "therapeutically effective amount" refers to that amount of active compound or pharmaceutical agent that elicits the biological or medicinal response in a patient, which includes alleviation of the symptoms of the disease or disorder being treated. In one aspect, the therapeutically effective amount is that which may treat or alleviate the disease or symptoms. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors. An exemplary dose is in the range of about from about 0.1 mg to 1 g daily, or about 1 mg to 50 mg daily, or about 50 to 250 mg daily, or about 250 mg to 1 g daily. The total dosage may be given in single or divided dosage units (e.g., BID, TID, QID).

As used herein, the term "disease" includes, but is not limited to, cancer, pain, psoriasis, rheumatoid arthritis, polycythemia vera, essential thrombocythemia, ulcerative colitis, and myeloid metaplasia with myelofibrosis.

As used herein, the term "cancer" includes, but is not limited to, ALCL, NSCLC, neuroblastoma, inflammatory myofibroblastic tumor, adult renal cell carcinoma, pediatric renal cell carcinoma, breast cancer, $ER^+$ breast cancer, colonic adenocarcinoma, glioblastoma, glioblastoma multiforme, anaplastic thyroid cancer, cholangiocarcinoma, ovarian cancer, gastric adenocarcinoma, colorectal cancer, inflammatory myofibroblastic tumor, angiosarcoma, epithelioid hemangioendothelioma, intrahepatic cholangiocarcinoma, thyroid papillary cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, skin cutaneous melanoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, and serous and clear cell endometrial cancer.

EMBODIMENTS

In some embodiments, the methods described herein relate to the treatment of disease comprising administering to a patient in need of treatment a therapeutically effective amount of a compound having activity against at least one tyrosine kinase selected from the group consisting of ALK, ROS1, TRK, JAK and SRC. In some embodiments, the compound has activity against at least one tyrosine or serine/threonine kinase selected from the group consisting of ALK, ROS1, TRKA, TRKB, TRKC, JAK2, SRC, FAK and ARK5. In some embodiments, the compound has activity against at least two tyrosine or serine/threonine kinases selected from the group consisting of ALK, ROS1, TRKA, TRKB, TRKC, JAK2, SRC, FAK and ARK5. In some embodiments, the at least one, or the at least two of the tyrosine or serine/threonine kinases are genetically altered. In some embodiments, the compound is of the formula I

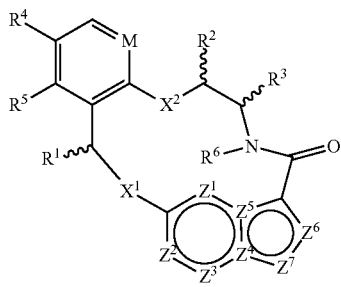

wherein $X^1$, $X^2$, $Z^1$, $Z^2$, $Z^3$, $Z^4$, $Z^5$, $Z^6$, $Z^7$, M, $R^1$, $R^2$, $R^3$, $R^4$, $R^5$ and $R^6$ are defined as described herein, or a pharmaceutically acceptable salt thereof.

It will be appreciated that the disease can be any of a number of diseases associated with the tyrosine kinases described herein against which the compounds of the formula I have activity. For example, the methods described herein can be used for the treatment of diseases such as cancer, pain, psoriasis, rheumatoid arthritis, polycythemia vera, essential thrombocythemia, ulcerative colitis, myeloid metaplasia with myelofibrosis, and the like. It will be appreciated that the disease can be any disease associated with the activity of a tyrosine kinase described herein. It will be further appreciated that the disease can be any disease associated with a genetically altered tyrosine or serine/threonine kinase selected from the group consisting of ALK, ROS1, TRKA, TRKB, TRKC, JAK2, SRC, FAK and ARK5. It will be further appreciated that the disease can be any disease associated with up-regulation of JAK2, SRC, FAK or ARK5. In some embodiments, the disease is a cancer mediated by or associated with a tyrosine kinase. In some embodiments, the disease is a cancer mediated by or associated with a serine/threonine kinase. In some embodiments, the disease is a cancer mediated by or associated with a genetically altered tyrosine kinase. In some embodiments, the disease is a cancer mediated by or associated with a genetically altered serine/threonine kinase. In some embodiments, the disease is a cancer mediated by or associated with up-regulation of JAK2, SRC, FAK or ARK5. In some embodiments, the disease is a cancer mediated by or associated with a genetically altered tyrosine kinase selected from the group consisting of ALK, ROS1, TRKA, TRKB, TRKC, JAK2, SRC and FAK. In some embodiments, the disease is a cancer mediated by or associated with a genetically altered serine/threonine kinase, such as ARK5.

It will be appreciated that the cancer can be any cancer mediated by or associated with a genetically altered tyrosine kinase selected from the group consisting of ALK, ROS1, TRKA, TRKB, TRKC and JAK2, or up-regulation of JAK2, SRC, FAK or ARK5, including but not limited to, ALCL, NSCLC, neuroblastoma, inflammatory myofibroblastic tumor, adult renal cell carcinoma, pediatric renal cell carcinoma, breast cancer, colonic adenocarcinoma, glioblastoma, glioblastoma multiforme, anaplastic thyroid cancer, cholangiocarcinoma, ovarian cancer, gastric adenocarcinoma, colorectal cancer, inflammatory myofibroblastic tumor, angiosarcoma, epithelioid hemangioendothelioma, intrahepatic cholangiocarcinoma, thyroid papillary cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, skin cutaneous melanoma, head and neck squamous cell carcinoma, pediatric glioma CML, and prostate cancer. In some embodiments, the cancer is NSCLC. In some embodiments, the cancer is colorectal cancer. In some embodiments, the cancer is neuroblastoma.

In some embodiments, the present disclosure provides methods of treating disease in a patient that has received a prior treatment with one or more therapeutic agents. In some embodiments, the patient has been previously treated with one or more chemotherapeutic agents. In still other embodiments, the patent has been previously treated with one or more chemotherapeutic agents and developed an acquired resistance to the treatment. In still other embodiments, the patent has been previously treated with one or more chemotherapeutic agents and developed bypass resistance to the treatment. In still other embodiments, the patent has been previously treated with one or more chemotherapeutic agents and developed bypass resistance to the treatment regulated by SRC or JAK2.

Other chemotherapeutic agents which the patient may be been treated with prior to treatment with one or more of the compounds described herein include but are not limited to kinase inhibitors, adrenocorticoids and corticosteroids, alkylating agents, peptide and peptidomimetic signal transduction inhibitors, antiandrogens, antiestrogens, androgens, aclamycin and aclamycin derivatives, estrogens, antimetabolites, platinum compounds, amanitins, plant alkaloids, mitomycins, discodermolides, microtubule inhibitors, epothilones, inflammatory and proinflammatory agents, purine analogs, pyrimidine analogs, camptothecins and dolastatins. In some embodiments, the chemotherapeutic agent the patient received previous to treatment with one or more compounds described herein can be one or more of afatinib, axitinib, alectinib, bosutinib, brigatini, cabozantinib, ceritinib, crizotinib, dabrefenib, dasatinib, erlotinib, everolimus, gefitinib, ibrutinib, imatinib, lapatinib, lenvatinib, nilotinib, nintedanib, palbociclib, pazopanib, ponatinib, regorafenib, ruxolitinib, sirolimus, sorafenib, sunitinib, tofacitinib, temsirolimus, trametinib, vandetanib, vemurafenib, methotrexate, busulfan, carboplatin, chlorambucil, cisplatin, tamoxiphen, taxol, paclitaxel, docetaxel, cytosine arabinoside, cyclophosphamide, daunomycin, rhizoxin, prednisone, hydroxyurea, teniposide, vincristine, vinblastine, eribulin, camptothecin, irinotecan, geldanamycin, estramustine and nocodazole. In some embodiments, the methods described herein provide treatment of a patient previously treated with a kinase inhibitor selected from the group consisting of afatinib, alectinib, axitinib, bosutinib, brigatini, cabozantinib, ceritinib, crizotinib, dabrefenib, dasatinib, erlotinib, everolimus, gefitinib, ibrutinib, imatinib, lapatinib, lenvatinib, nilotinib, nintedanib, palbociclib, pazopanib, ponatinib, regorafenib, ruxolitinib, sirolimus, sorafenib, sunitinib, tofacitinib, temsirolimus, trametinib, vandetanib and vemurafenib. In some embodiments, the patient was previously treated with crizotinib.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.1 mg to 1 g daily, or about 1 mg to 50 mg daily, or about 50 to 250 mg daily, or about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier. The inventive compositions may be formulated for rectal administration as a suppository.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

Drug Combinations

The compounds described herein may be used in pharmaceutical compositions or methods in combination with one or more additional active ingredients in the treatment of the diseases and disorders described herein. Further additional active ingredients include other therapeutics or agents that mitigate adverse effects of therapies for the intended disease targets. Such combinations may serve to increase efficacy, ameliorate other disease symptoms, decrease one or more side effects, or decrease the required dose of an inventive compound. The additional active ingredients may be administered in a separate pharmaceutical composition from a compound of the present invention or may be included with a compound of the present invention in a single pharmaceutical composition. The additional active ingredients may be administered simultaneously with, prior to, or after administration of a compound of the present invention.

Combination agents include additional active ingredients are those that are known or discovered to be effective in treating the diseases and disorders described herein, including those active against another target associated with the disease. For example, compositions and formulations of the invention, as well as methods of treatment, can further comprise other drugs or pharmaceuticals, e.g., other active agents useful for treating or palliative for the target diseases or related symptoms or conditions.

Other chemotherapeutic agents suitable for use in combination in the methods described herein include but are not limited to kinase inhibitors, adrenocorticoids and corticosteroids, alkylating agents, peptide and peptidomimetic signal transduction inhibitors, antiandrogens, antiestrogens, androgens, aclamycin and aclamycin derivatives, estrogens, antimetabolites, platinum compounds, amanitins, plant alkaloids, mitomycins, discodermolides, microtubule inhibitors, epothilones, inflammatory and proinflammatory agents, purine analogs, pyrimidine analogs, camptothecins and dolastatins. In some embodiments, chemotherapeutic agents suitable for combination treatments in the methods described herein include but are not limited to one or more of afatinib, alectinib, axitinib, bosutinib, brigatini, cabozantinib, ceritinib, crizotinib, dabrefenib, dasatinib, erlotinib, everolimus, gefitinib, ibrutinib, imatinib, lapatinib, lenvatinib, nilotinib, nintedanib, palbociclib, pazopanib, ponatinib, regorafenib, ruxolitinib, sirolimus, sorafenib, sunitinib, tofacitinib, temsirolimus, trametinib, vandetanib, vemurafenib, methotrexate, busulfan, carboplatin, chlorambucil, cisplatin, tamoxiphen, taxol, paclitaxel, docetaxel, cytosine arabinoside, cyclophosphamide, daunomycin, rhizoxin, prednisone, hydroxyurea, teniposide, vincristine, vinblastine, eribulin, camptothecin, irinotecan, geldanamycin, estramustine and nocodazole. chemotherapeutic agents suitable for combination treatments in the methods described herein include but are not limited to one or more kinase inhibitor selected from the group consisting of afatinib, alectinib, axitinib, bosutinib, brigatini, cabozantinib, ceritinib, crizotinib, dabrefenib, dasatinib, erlotinib, everolimus, gefitinib, ibrutinib, imatinib, lapatinib, lenvatinib, nilotinib, nintedanib, palbociclib, pazopanib, ponatinib, regorafenib, ruxolitinib, sirolimus, sorafenib, sunitinib, tofacitinib, temsirolimus, trametinib, vandetanib and vemurafenib. In some embodiments, the patient was previously treated with crizotinib. For pain indications, suitable combination agents include anti-inflammatories such as NSAIDs. The pharmaceutical compositions of the invention may additional comprise one or more of such active agents, and methods of treatment may additionally comprise administering an effective amount of one or more of such active agents.

Diagnostic Tests

In some embodiments, the present disclosure provides methods for treating disease in a patient previously identified as having a genetically altered tyrosine or serine/threonine kinase, such as a gene fusion. In some embodiments, the present disclosure provides methods for treating cancer in a patient previously identified as having a genetically altered tyrosine or serine/threonine kinase, such as a gene fusion. In some embodiments, the present disclosure provides methods for treating disease in a patient comprising (i) identifying a genetically altered tyrosine or serine/threonine kinase in the patient, and (ii) administering to the patient a therapeutically effective amount of a compound useful in the treatment of such disease.

It will be appreciated that the diagnosing or identifying a patient as having a genetically altered tyrosine or serine threonine kinase can be accomplished by any number of diagnostic tests known to one of skill in the art. For example, such diagnostic tests include, but are not limited to, fluorescence in situ hybridization (FISH), polymerase chain reaction (PCR), immunohistochemistry (IHC), whole genome sequencing, next generation sequencing, and the like. It will also be appreciated that any of the methods known in the art and applicable to diagnosing a patient or identifying a patient in connection with the present disclosure involve the transformation of a biological sample from one state of matter to another by direct modification, synthesis or by direct non-covalent connection to provide a modified sample that can be used to determine whether the subject has or does not have a genetically altered tyrosine or serine threonine kinase. In some embodiments, "diagnosing" or "identifying" with respect to the disease state of a patient means applying a diagnostic test, such as FISH, PCR or IHC, to a biological sample obtained from the patient.

It will be appreciated that FISH is a test that "maps" the genetic material in a person's cells. This test can be used to visualize specific genes or portions of genes. FISH is a cytogenetic technique that uses fluorescent probes that bind to only those parts of the chromosome with a high degree of sequence complementarity. Such FISH tests can be used to identify a patient with a genetically altered tyrosine or serine/threonine kinase by any method known in the art, and such test can be used in combination with the methods described herein as either a means of prior identification of a patient for treatment, or the concomitant identification of a patient for treatment.

It will be appreciated that IHC refers to the process of detecting antigens (e.g., proteins) in cells of a tissue section by exploiting the principle of antibodies binding specifically to antigens in biological tissues. Immunohistochemical staining is widely used in the diagnosis of abnormal cells such as those found in cancerous tumors. Specific molecular markers are characteristic of particular cellular events such as proliferation or cell death (apoptosis). Visualising an antibody-antigen interaction can be accomplished in a number of ways. In the most common instance, an antibody is conjugated to an enzyme, such as peroxidase, that can catalyse a colour-producing reaction. Alternatively, the antibody can also be tagged to a fluorophore, such as fluorescein or rhodamine. Such IHC tests can be used to identify a patient with a genetically altered tyrosine or serine/threonine kinase by any method known in the art, and such test can be used in combination with the methods described herein as either a means of prior identification of a patient for treatment, or the concomitant identification of a patient for treatment.

It will be appreciated that PCR refers to a technology in molecular biology used to amplify a single copy or a few copies of a piece of DNA across several orders of magnitude, generating thousands to millions of copies of a particular DNA sequence. Such PCR tests can be used to identify a patient with a genetically altered tyrosine or serine/threonine kinase by any method known in the art, and such test can be used in combination with the methods described herein as either a means of prior identification of a patient for treatment, or the concomitant identification of a patient for treatment.

It will be appreciated that whole genome sequencing or next-generation sequencing refers to a process that determines the complete DNA sequence of an organism's genome at a single time. This entails sequencing all of an organism's chromosomal DNA as well as DNA contained in the mitochondria. Such whole genome sequencing tests can be used to identify a patient with a genetically altered tyrosine or serine/threonine kinase by any method known in the art, and such test can be used in combination with the methods described herein as either a means of prior identification of a patient for treatment, or the concomitant identification of a patient for treatment.

EXAMPLES

The examples and preparations provided below further illustrate and exemplify particular aspects of embodiments of the disclosure. It is to be understood that the scope of the present disclosure is not limited in any way by the scope of the following examples.

Abbreviations

The examples described herein use materials, including but not limited to, those described by the following abbreviations known to those skilled in the art:

| | |
|---|---|
| g | grams |
| eq | equivalents |
| mmol | millimoles |
| mol | moles |
| mL | milliliters |
| L | liters |
| EtOAc or EA | ethyl acetate |
| MeCN | acetonitrile |
| DCM | dichloromethane |
| DEAD | diethyl azodicarboxylate |
| MHz | megahertz |
| δ | chemical shift |
| THF | tetrahydrofuran |
| PE | petroleum ether |
| $R_f$ | retardation factor |
| DMSO-$d_6$ | deuterated dimethyl sulfoxide |
| CDCl$_3$ | deuterated chloroform |
| n-BuOH | n-butanol |
| DIEA | n,n-diisopropylethylamine |
| TMSCl | trimethylsilyl chloride |
| min | minutes |
| hrs, hr or h | hours |
| TLC | thin layer chromatography |
| M | molar |
| MS | mass spectrum |
| m/z | mass-to-charge ratio |
| FDPP | pentafluorophenyl diphenylphosphinate |
| DMAP | 4-(dimethylamino)pyridine |
| DMF | N,N-dimethylformamide |

Synthesis of Compound 1

Compound 1 was prepared according to the following synthetic scheme:

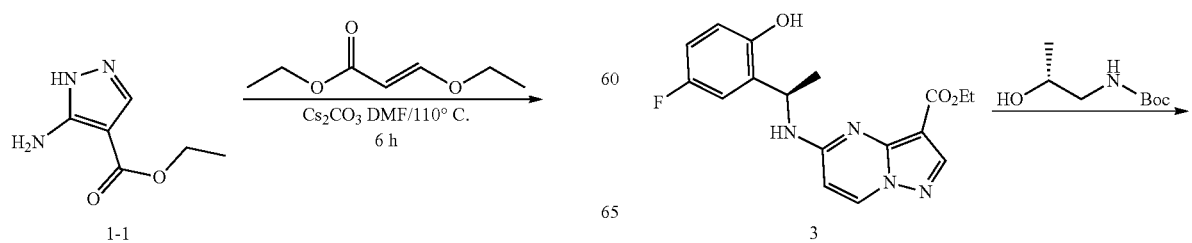

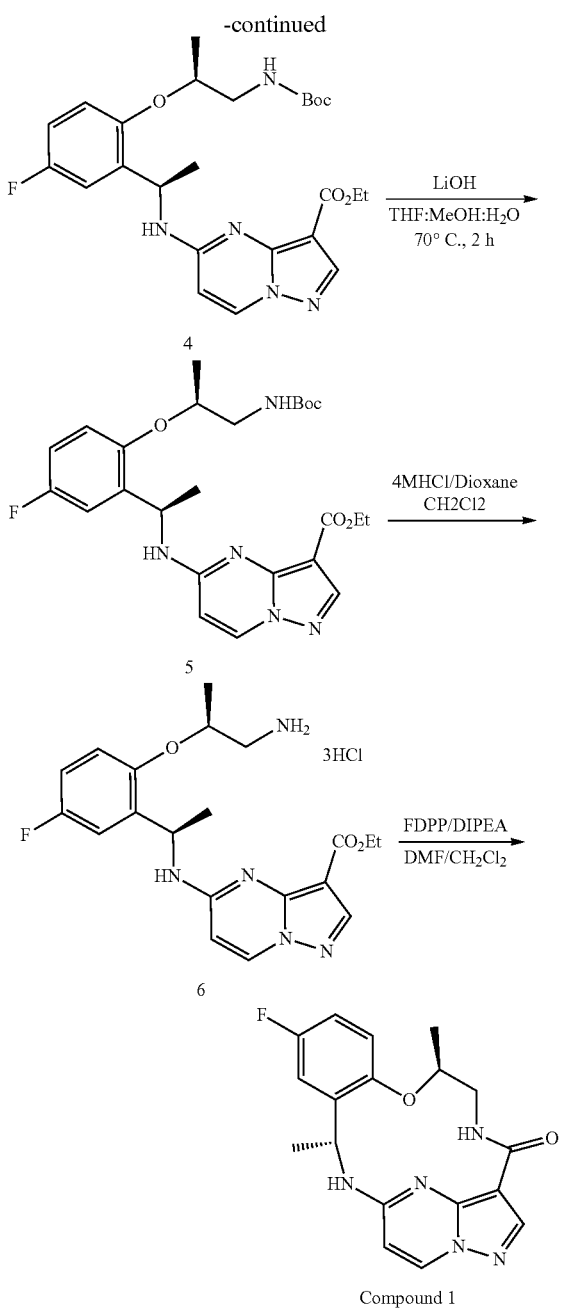

Example 1: Preparation of 5-chloropyrazolo[1,5-a]pyrimidine-3-carboxylate (1a)

Step 1: Preparation of ethyl 5-oxo-4H-pyrazolo[1,5-a]pyrimidine-3-carboxylate (1-2)

To a mixture of ethyl 5-amino-1H-pyrazole-4-carboxylate (Sigma-Aldrich, 150.00 g, 1.08 mmol) and ethyl (E)-3-ethoxyprop-2-enoate (Sigma-Aldrich, 292.16 g, 2.03 mol) in DMF (3.2 L) was added $Cs_2CO_3$ (656.77 g, 2.02 mol) in one portion at 20° C. under $N_2$. The mixture was stirred at 110° C. for 6 h. TLC (PE:EtOAc=1:1) showed the reaction was completed. The mixture was cooled to 20° C. and filtered through a celite pad. The filter cake was washed with ethyl acetate (3×30 mL). The filtrate was added to $H_2O$ (2 L) and acidified with HOAc to pH=4. The resultant precipitate was filtered to afford 1-2 (173.00 g, 834.98 mmol, 86.36% yield) as a white solid: $^1H$ NMR (400 MHz, DMSO-$d_6$) δ 8.54 (d, J=7.91 Hz, 1H), 8.12 (s, 1H), 6.13 (d, J=7.91 Hz, 1H), 4.27 (q, J=7.11 Hz, 2H), 1.28 (t, J=7.09 Hz, 3H).

Step 2: Preparation of 5-chloropyrazolo[1,5-a]pyrimidine-3-carboxylate (1)

To a mixture of 1-2 (158.00 g, 762.59 mmol) in MeCN (1.6 L) was added $POCl_3$ (584.64 g, 3.81 mol) at 20° C. under $N_2$. The mixture was stirred at 100° C. for 2 h. TLC (PE:EA=1:1) showed the reaction was completed. The mixture was cooled to 20° C. and poured into ice-water (5000 mL) in portions at 0° C. and stirred for 20 min. The precipitate was filtered and dried to afford 1a (110.00 g, 487.52 mmol, 63.93% yield) as a white solid: $^1H$ NMR (400 MHz, DMSO-$d_6$) δ 9.33 (d, J=7.28 Hz, 1H), 8.66 (s, 1H), 7.41 (d, J=7.15 Hz, 1H), 4.31 (q, J=7.15 Hz, 2H), 1.32 (t, J=7.09 Hz, 3H).

Example 2: Preparation of (R)-2-(1-aminoethyl)-4-fluorophenol (2)

Step 1: Preparation of (R)—N-(5-fluoro-2-hydroxybenzylidene)-2-methylpropane-2-sulfinamide (2-2)

To a solution of (R)-2-methylpropane-2-sulfinamide (Sigma-Aldrich, 150.00 g, 1.24 mol, 1.00 eq.) and 5-fluoro-2-hydroxybenzaldehyde (2-1) (Sigma-Aldrich, 173.74 g, 1.24 mol, 1.00 eq.) in DCM (2.00 L) was added $Cs_2CO_3$ (646.43 g, 1.98 mol, 1.60 eq.). The mixture was stirred at 16° C. for 16 hours. TLC (PE:EtOAc=5:1) showed the reaction was completed. The reaction mixture was quenched by addition of $H_2O$ (1000 mL) at 0° C. and then extracted with EtOAc (500 mL×4). The combined organic layers were washed with brine (1000 mL) and dried over $Na_2SO_4$, filtered and concentrated under reduced pressure to give 2-2 (230.00 g, 945.33 mmol, 76.24% yield). $^1HNMR$ (CDCl$_3$, 400 MHz) δ 8.64 (s, 1H), 7.22-7.11 (m, 2H), 7.03-6.95 (m, 1H), 1.28 (s, 9H).

Step 2: Preparation of (R)—N—((R)-1-(5-fluoro-2-hydroxyphenyl)ethyl)-2-methylpropane-2-sulfinamide (2-3R)

To a solution of (R)—N-(5-fluoro-2-hydroxybenzylidene)-2-methylpropane-2-sulfinamide (2-2) (200.00 g, 822.03 mmol, 1.00 eq.) in THF (2.5 L) was added MeMgBr (490.09 g, 4.11 mol, 5.00 eq.) drop-wise at −65° C. under $N_2$ over a period of 30 min. The mixture was then warmed to ambient temperature and stirred for 18 hours. TLC (PE:EtOAc=1:1) showed the reaction was complete with the production of two diastereomers. The reaction mixture was quenched by addition of $H_2O$ (2 L) at 0° C., the mixture was extracted with EtOAc (500 mL×3). The combined organic layers were washed with brine (500 mL), dried over $Na_2SO_4$, filtered and concentrated under reduced pressure to give a residue. The residue was purified by column chromatography ($SiO_2$, Petroleum ether/Ethyl acetate=50/1 to 1:1) to give (R)—N—((R)-1-(5-fluoro-2-hydroxyphenyl)ethyl)-2-methylpropane-2-sulfinamide (2-3R) (125 g, the top, less polar spot with Rf: 0.5, PE:EA=1:1). $^1HNMR$ (CDCl$_3$, 400 MHz) δ: 9.17 (s, 1H), 6.68 (dd, J=3.0, 8.8 Hz, 1H), 6.47 (dt, J=3.0, 8.4 Hz, 1H), 6.31 (dd, J=4.8, 8.8 Hz, 1H), 5.11 (d, J=8.0 Hz, 1H), 4.28 (quin, J=7.2 Hz, 1H), 1.43 (d, J=6.8 Hz, 3H), 1.20 (s, 9H).

Step 3: Preparation of (R)-2-(1-aminoethyl)-4-fluorophenol (2)

A solution of (R)—N—((R)-1-(5-fluoro-2-hydroxyphenyl)ethyl)-2-methylpropane-2-sulfinamide (2-3R) (125 g, 481.99 mmol, 1.00 eq.) in HCl/dioxane (1.5 L, 4N) was stirred at ambient temperature for 2 hours. TLC (PE:EtOAc=2:1) showed the reaction was complete. The mixture was filtered to give (R)-2-(1-aminoethyl)-4-fluorophenol (2) HCl salt (85 g, 443.56 mmol, 90.03% yield) as a white solid. $^1$HNMR (d-DMSO, 400 MHz) δ 10.24 (s, 1H), 8.48 (br. s., 3H), 7.31 (dd, J=2.9, 9.7 Hz, 1H), 7.05-6.99 (m, 1H), 6.98-6.93 (m, 1H), 4.59-4.45 (m, 1H), 1.46 (d, J=6.8 Hz, 3H).

Example 3: Preparation of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one (Compound 1)

Step 1: Preparation of ethyl (R)-5-((1-(5-fluoro-2-hydroxyphenyl)ethyl)amino)pyrazolo[1,5-a]pyrimidine-3-carboxylate (3)

To a solution of (R)-2-(1-aminoethyl)-4-fluorophenol (2) (85 g, 443.56 mmol, 1.00 eq.) and ethyl 5-chloropyrazolo[1,5-a]pyrimidine-3-carboxylate (1a) (100.08 g, 443.56 mmol, 1.00 eq.) in n-BuOH (2 L) was added DIEA (343.96 g, 2.66 mol, 6.00 eq.). The mixture was stirred at 120° C. for 2 hrs. TLC (PE:EtOAc=1:1) showed the reaction was completed. The reaction mixture was diluted with H$_2$O (500 mL) at 16° C., and extracted with EtOAc (500 mL×3). The combined organic layers were washed with brine (500 mL), dried over Na$_2$SO$_4$, filtered and concentrated under reduced pressure to give a residue. The residue was purified by column chromatography (SiO$_2$, Petroleum ether/Ethyl acetate=10/1 to 1:3) to give ethyl (R)-5-((1-(5-fluoro-2-hydroxyphenyl)ethyl)amino)pyrazolo[1,5-a]pyrimidine-3-carboxylate (3) (122 g, 349.34 mmol, 78.76% yield, ee>99% purity) as a white solid. $^1$HNMR (CDCl$_3$, 400 MHz) δ 9.28 (br. s., 1H), 8.26 (s, 1H), 8.14 (d, J=7.5 Hz, 1H), 6.95-6.89 (m, 2H), 6.87-6.80 (m, 1H), 6.18 (d, J=7.5 Hz, 1H), 5.98 (d, J=8.3 Hz, 1H), 5.71-5.54 (m, 1H), 4.50-4.35 (m, 2H), 1.60 (d, J=6.8 Hz, 3H), 1.42 (t, J=7.2 Hz, 3H).

Step 2: Preparation of ethyl 5-(((R)-1-(2-(((S)-1-((tert-butoxycarbonyl)amino)propan-2-yl)oxy)-5-fluorophenyl)ethyl)amino)pyrazolo[1,5-a]pyrimidine-3-carboxylate (4)

A mixture of ethyl (R)-5-((1-(5-fluoro-2-hydroxyphenyl)ethyl)amino)pyrazolo[1,5-a]pyrimidine-3-carboxylate (3) (10.00 g, 29.04 mmol) and tert-butyl (R)-(2-hydroxypropyl)carbamate (Combi-Blocks, 7.63 g, 43.56 mmol) was azetrope dried from DCM/toluene, and then re-dissolved in DCM (11.62 mL). To the solution was added PPh$_3$ (11.43 g, 43.56 mmol), and the mixture was stirred until the starting materials were completely dissolved. To the solution was added DEAD (8.81 g, 43.56 mmol) over 5 min with mixing. The reaction was stirred for 3 hours. The reaction mixture was diluted with DCM (125 mL), followed by addition of aqueous NaOH solution (2M, 100 mL). The mixture was stirred vigorously for 12 hours and the layers were separated. The aqueous layer was further extracted with DCM (3×50 mL). The combined extracts were washed with brine (50 mL), dried with Na$_2$SO$_4$, and concentrated under reduced pressure. The residue was purified with flash chromatography (Teledyne ISCO system, silica (330 g), 0-40% ethyl acetate in hexane to provide ethyl 5-(((R)-1-(2-(((S)-1-((tert-butoxycarbonyl)amino)propan-2-yl)oxy)-5-fluorophenyl)ethyl)amino)-pyrazolo[1,5-a]pyrimidine-3-carboxylate (4) (8.88 g, 60.9% yield). LC-MS m/z 502.2 (M+H)$^+$. $^1$HNMR (400 MHz, CHLOROFORM-d) δ 8.24 (s, 1H), 8.21 (d, J=7.6 Hz, 1H), 7.04 (d, J=8.4 Hz, 1H), 6.87 (d, J=6.0 Hz, 2H), 6.13 (d, J=7.2 Hz, 1H), 5.91 (br. s., 1H), 4.58 (d, J=3.6 Hz, 1H), 4.43-4.28 (m, 2H), 3.52-3.34 (m, 2H), 1.54 (d, J=6.8 Hz, 3H), 1.47-1.36 (m, 12H), 1.30 (d, J=6.4 Hz, 3H).

Step 3: Preparation of 5-(((R)-1-(2-(((S)-1-((tert-butoxycarbonyl)amino)propan-2-yl)oxy)-5-fluorophenyl)ethyl)amino)pyrazolo[1,5-a]pyrimidine-3-carboxylic acid (5)

To a solution of ethyl 5-(((R)-1-(2-(((S)-1-((tert-butoxycarbonyl)amino)propan-2-yl)oxy)-5-fluorophenyl)ethyl)amino)pyrazolo[1,5-a]pyrimidine-3-carboxylate (4) (6.98 g, 13.92 mmol, 1 eq.) in methanol (65 mL) and THF (20 mL) was added LiOH (2M, 47.9 mL, 95.8 mmol). The mixture was heated at 70° C. for 3 hrs, cooled to ambient temperature, and then quenched with aq. HCl (2M, 95.8 mL) to adjust pH<5. The reaction mixture was extracted with CH$_2$Cl$_2$ (3×50 mL), and dried over Na$_2$SO$_4$. After filtration, evaporation, and high vacuum dry, a white solid of 5-(((R)-1-(2-(((S)-1-((tert-butoxycarbonyl)amino)propan-2-yl)oxy)-5-fluorophenyl)ethyl)amino)pyrazolo[1,5-a]pyrimidine-3-carboxylic acid (5) was obtained which was used in the next step without further purification. LC-MS m/z 474.2 (M+H)$^+$.

Step 4: Preparation of 5-(((R)-1-(2-(((S)-1-aminopropan-2-yl)oxy)-5-fluorophenyl)ethyl)amino)pyrazolo[1,5-a]pyrimidine-3-carboxylic acid (6)

To a solution of 5-(((R)-1-(2-(((S)-1-((tert-butoxycarbonyl)amino)propan-2-yl)oxy)-5-fluorophenyl)ethyl)amino)pyrazolo[1,5-a]pyrimidine-3-carboxylic acid (5) (6.59 g, 13.92 mmol) in CH$_2$Cl$_2$ (130 mL) was added HCl in dioxane (4 M, 30.4 mL). Keep stirring at room temperature for 2 hours until the reaction was shown to be completed by LC-MS. The reaction mixture was concentrated, and high vacuum dried to provide compound 6 as a white solid which was used in the next step without further purification. LC-MS m/z 374.2 (M+H)$^+$.

Step 5: Preparation of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one (Compound 1)

5-(((R)-1-(2-(((S)-1-aminopropan-2-yl)oxy)-5-fluorophenyl)ethyl)amino)pyrazolo[1,5-a]pyrimidine-3-carboxylic acid (6) (5.20 g, 13.93 mmol) was dissolved in DMF (75 mL) to make Solution A. To a solution of Hunig's base (DIPEA) (14.40 g, 111.4 mmol) in DMF (150 mL) and DCM (350 mL) was added solution A (25 mL) and one third of the total FDPP (5.62 g, 14.63 mmol) sequentially. The reaction was stirred for 1 hour, and LC-MS showed the completion of the coupling reaction. The same process was repeated for 2 more times. The final solution was stirred at ambient temperature for 63 hour (or until the reaction was shown to be completed by LC-MS). The reaction was quenched by addition of aqueous $Na_2CO_3$ solution (2M, 150 mL), and the mixture was stirred for 15 min, and extracted with DCM (3×150 mL). The combined extracts were dried with $Na_2SO_4$, concentrated under reduced pressure, and purified on a flash chromatography (Teledyne ISCO system, silica (220 g), 0-7.5% methanol in dichloromethane) to provide (7S,13R)-11-fluoro-7,13-dimethyl-6,7,13,14-tetrahydro-1, 15-ethenopyrazolo[4,3-f][1,4,8,10]benzoxatriazacyclotridecin-4(5H)-one (Compound 1) (4.38 g, 12.33 mmol, 88.5% yield) as a white solid. LC-MS: m/z [M+H]+ 356.2. $^1H$ NMR (500 MHz, DMSO-$d_6$) δ ppm 9.82 (dd, J=8.02, 2.29 Hz, 1H), 8.81 (d, J=6.87 Hz, 1H), 8.58 (d, J=7.45 Hz, 1H), 8.04 (s, 1H), 7.12 (dd, J=9.45, 3.15 Hz, 1H), 6.99-7.05 (m, 1H), 6.94-6.99 (m, 1H), 6.36 (d, J=7.45 Hz, 1H), 5.53 (m, 1H), 4.45-4.52 (m, 1H), 3.90 (ddd, J=13.46, 8.31, 4.01 Hz, 1H), 3.10-3.17 (m, 1H), 1.46 (d, J=6.30 Hz, 3H), 1.44 (d, J=7.45 Hz, 3H).

In-Vitro Assays

Materials and Methods

Kinase Binding Assay Method

Kinase binding assays were performed at DiscoveRx using the general KINOMEscan $K_d$ Protocol (Fabian, M. A. et al., "A small molecule-kinase interaction map for clinical kinase inhibitors," Nat. Biotechnol. 2005, 23(3):329-36). For most assays, kinase-tagged T7 phage strains were prepared in an E. coli host derived from the BL21 strain. E. coli were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding. Binding reactions were assembled by combining kinases, liganded affinity beads, and test compounds in 1×binding buffer (20% SeaBlock, 0.17×PBS, 0.05% Tween 20, 6 mM DTT). All reactions were performed in polystyrene 96-well plates in a final volume of 0.135 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

Binding constants ($K_d$s) were calculated with a standard dose-response curve using the Hill equation: Response=Background+(Signal−Background)/(1+ ($Kd^{Hill\ Slope}/Dose^{Hill\ Slope}$)) The Hill Slope was set to −1. Curves were fitted using a non-linear least square fit with the Levenberg-Marquardt algorithm.

Biochemical Kinase Assay Method

The biochemical kinase assay was performed at Reaction Biology Corporation (www.reactionbiology.com, Malvern, PA) following the procedures described in the reference (Anastassiadis T, et al Nat Biotechnol. 2011, 29, 1039). Specific kinase/substrate pairs along with required cofactors were prepared in reaction buffer; 20 mM Hepes pH 7.5, 10 mM MgCl2, 1 mM EGTA, 0.02% Brij35, 0.02 mg/ml BSA, 0.1 mM Na3VO4, 2 mM DTT, 1% DMSO (for specific details of individual kinase reaction components see Supplementary Table 2). Compounds were delivered into the reaction, followed ~20 minutes later by addition of a mixture of ATP (Sigma, St. Louis MO) and $^{33}P$ ATP (Perkin Elmer, Waltham MA) to a final concentration of 10 μM. Reactions were carried out at room temperature for 120 min, followed by spotting of the reactions onto P81 ion exchange filter paper (Whatman Inc., Piscataway, NJ). Unbound phosphate was removed by extensive washing of filters in 0.75% phosphoric acid. After subtraction of background derived from control reactions containing inactive enzyme, kinase activity data was expressed as the percent remaining kinase activity in test samples compared to vehicle (dimethyl sulfoxide) reactions. $IC_{50}$ values and curve fits were obtained using Prism (GraphPad Software).

Cell Lines and Cell Culture:

Human lung cancer cell line NCI-H2228 was obtained from ATCC. Cell lines 293T, NIH3T3, Ba/F3, and HCC78 were purchased from DSMZ. Karpas-299 cell line was purchased from Sigma. KM12 cell line was obtained from NCI.

NIH3T3 was maintained in DMEM medium supplemented with 10% fetal bovine serum and 100 U/mL of penicillin/streptomycin. HCC78, Karpas-299 and H2228 were maintained in RPMI-1640 supplemented with 10% fetal bovine serum with 100 U/mL of penicillin/streptomycin. Ba/F3 cells were maintained in RPMI-1640 supplemented with 10% fetal bovine serum, 10% (Vol/Vol) conditioned media from the WIHI-3B myelomonocytic IL-3 secreting cells and 100 U/mL of penicillin/streptomycin. BaF3 stable cell lines were maintained in RPMI-1640 supplemented with 10% fetal bovine serum, 100 U/mL of penicillin, and 0.5 μg/mL puromycin solution.

Cloning and Ba/F3 or NIH3T3 Stable Cell Line Creation

The EML4-ALK gene (variant 1) was synthesized at GenScript and cloned into pCDH-CMV-MCS-EF1-Puro plasmid (System Biosciences, Inc). EML4-ALK point mutations G1202R, L1196M, L1152P, F1174C, C1156Y, I1171N, G1269S, and 1151T insertion were generated at GenScript by PCR and confirmed by sequencing. Ba/F3-EML4-ALK wild type and mutants were generated by transducing Ba/F3 cells with lentivirus containing EML4-ALK wide type or mutants. Stable cell lines were selected by puromycin treatment, followed by IL-3 withdrawal. Briefly, 5×10⁶ Ba/F3 cells were transduced with lentivirus supernatant in the presence of 8 μg/mL protamine sulfate. The transduced cells were subsequently selected with 1 μg/mL puromycin in the presence of IL3-containing medium RPMI1640, plus 10% FBS. After 10-12 days of selection, the surviving cells were further selected for IL3 independent growth.

SDC4-ROS1 wild type, CD74-ROS1 wild type, and their G2032R mutant genes were synthesized at GenScript and cloned into pCDH-CMV-MCS-EF1-Puro plasmid (System Biosciences, Inc), and confirmed by sequencing. Ba/F3 SDC4-ROS1, CD74-ROS1 and corresponding G2032R mutants were generated by transducing Ba/F3 cells with lentivirus containing the fusion genes. Stable cell lines were selected by puromycin treatment, followed by IL-3 withdrawal. Briefly, 5×10⁶ Ba/F3 cells were transduced with lentivirus supernatant in the presence of 8 μg/mL protamine sulfate. The transduced cells were subsequently selected with 1 μg/mL puromycin in the presence of IL3-containing medium RPMI1640, plus 10% FBS. After 10-12 days of selection, the surviving cells were further selected for IL3 independent growth.

Ba/F3 TPR-ALK and Ba/F3 TPR-ALK L1196M cell lines were created at Advanced Cellular Dynamics, Inc. and cell proliferation assays were performed there. The ACD panel itself is comprised of 92 unique kinases individually expressed in a common lymphoid cell line (mouse Ba/F3 cells). Each cell line is dependent upon activity of the recombinant kinase for survival.

SDC4-ROS1 L2026M and D2033N mutant genes were synthesized at GenScript and cloned into pCDH-CMV-MCS-EF1-Puro plasmid (System Biosciences, Inc), and confirmed by sequencing. Ba/F3 CD74-ROS1 L2026M and D2033N mutants were generated by transducing Ba/F3 cells with lentivirus containing the fusion genes. Stable cell lines were selected by puromycin treatment, followed by IL-3 withdrawal. Briefly, $5 \times 10^6$ Ba/F3 cells were transduced with lentivirus supernatant in the presence of 8 µg/mL protamine sulfate. The transduced cells were subsequently selected with 1 µg/mL puromycin in the presence of IL3-containing medium RPMI1640, plus 10% FBS. After 10-12 days of selection, the surviving cells were further selected for IL3 independent growth.

LMNA-TRKA wild type, and its G595R mutant genes were synthesized at GenScript and cloned into pCDH-CMV-MCS-EF1-Puro plasmid (System Biosciences, Inc), and confirmed by sequencing. Ba/F3 LMNA-TRKA and corresponding G595R mutant were generated by transducing Ba/F3 cells with lentivirus containing the fusion genes. Stable cell lines were selected by puromycin treatment, followed by IL-3 withdrawal. Briefly, $5 \times 10^6$ Ba/F3 cells were transduced with lentivirus supernatant in the presence of 8 µg/mL protamine sulfate. The transduced cells were subsequently selected with 1 µg/mL puromycin in the presence of IL3-containing medium RPMI1640, plus 10% FBS. After 10-12 days of selection, the surviving cells were further selected for IL3 independent growth.

TEL-TRKB (also named as ETV6-TRKB) wild type and its G639R mutant genes were synthesized at GenScript and cloned into pCDH-CMV-MCS-EF1-Puro plasmid (System Biosciences, Inc), and confirmed by sequencing. Ba/F3 TEL-TRKB and corresponding G639R mutants were generated by transducing Ba/F3 cells with lentivirus containing the fusion genes. Stable cell lines were selected by puromycin treatment, followed by IL-3 withdrawal. Briefly, $5 \times 10^6$ Ba/F3 cells were transduced with lentivirus supernatant in the presence of 8 µg/mL protamine sulfate. The transduced cells were subsequently selected with 1 µg/mL puromycin in the presence of IL3-containing medium RPMI1640, plus 10% FBS. After 10-12 days of selection, the surviving cells were further selected for IL3 independent growth.

TEL-TRKC (also named as ETV6-TRKC) wild type and its G623R mutant genes were synthesized at GenScript and cloned into pCDH-CMV-MCS-EF1-Puro plasmid (System Biosciences, Inc), and confirmed by sequencing. Ba/F3 TEL-TRKC and corresponding G623R mutant were generated by transducing Ba/F3 cells with lentivirus containing the fusion genes. Stable cell lines were selected by puromycin treatment, followed by IL-3 withdrawal. Briefly, $5 \times 10^6$ Ba/F3 cells were transduced with lentivirus supernatant in the presence of 8 µg/mL protamine sulfate. The transduced cells were subsequently selected with 1 µg/mL puromycin in the presence of IL3-containing medium RPMI1640, plus 10% FBS. After 10-12 days of selection, the surviving cells were further selected for IL3 independent growth.

NIH3T3 ALK or ROS1 stable cell lines were generated by transducing the cells with lentivirus containing EML4-ALK wild type and G1202R mutant genes, SDC4-ROS1 wild type, CD74-ROS1 wild type and their G2032R mutant genes. The transduced cells were subsequently selected with 1 µg/mL puromycin.

NIH3T3 ROS1, or TRKA, or TRKB, or TRKC stable cell lines were generated by transducing the cells with lentivirus containing CD74-ROS1 L2026M and D2033N mutant genes, LMNA-TRKA wild type and G595R mutant genes, TEL-TRKB wild type and G639R mutant genes, TEL-TRKB wild type and G623R mutant genes, respectively. The transduced cells were subsequently selected with 1 µg/mL puromycin.

Cell Proliferation Assays:

Two thousand cells per well were seeded in 384 well white plate for 24 hrs, and then treated with compounds for 72 hours (37° C., 5% $CO_2$). Cell proliferation was measured using CellTiter-Glo luciferase-based ATP detection assay (Promega) following the manufactures's protocol. $IC_{50}$ determinations were performed using GraphPad Prism software (GraphPad, Inc., San Diego, CA).

The cell proliferation assay of Ba/F3 TPR-ALK and Ba/F3 TPR-ALK L1196M cell lines were performed at Advanced Cellular Dynamics, Inc. The inhibition of kinase activity leads to cell death, which is monitored via ATP concentration using CellTiter-Glo (Promega). Cell lines were maintained in RPMI-1640 culture media containing 10% fetal calf serum and antibiotics. Cells in logarithmic-phase growth were harvested and 5,000 cells were distributed into each well of a 384-well plate in 50 µL of growth media. Parental cells (only) were seeded in the presence of 10 ng/mL IL3 to support cell growth and survival. Fifty nanoliters diluted compound were added to appropriate wells, in duplicate, and the cells were cultured for 48 hours at 37 C in a humidified 5% CO2 atmosphere. Viability was determined by adding 15 µL CellTiter-Glo and measuring luminescence, which is reported as relative light units (RLU) measured in counts per second.

Immunoblotting for Cellular Kinase Phosphorylation Assays

NSCLC cell line H2228 (harboring endogenous EML4-ALK fusion gene), HCC78 cells (harboring endogenous SLC34A2-ROS1 fusion gene), Karpas-299 cells (harboring endogenous NPM-ALK fusion gene) or SET-2 (harboring endogenous JAK2V617F activating mutation) were cultured in RPMI medium, and KM12 (harboring endogenous TPM3-TRKA fusion gene) cell line was cultured in DMEM medium, both supplemented with 10% fetal bovine serum and 100 U/mL of penicillin/streptomycin. Ba/F3 and NIH3T3 cells stably expressing ALK or ROS1 (WT or mutant) were culture as mentioned above. Half a million cells per well were seeded in 24 well plate for 24 hrs, and then treated with compounds for 4 hours. Cells were collected after treatment and lysed in RIPA buffer (50 mM Tris, pH 7.4, 150 mM NaCl, 1% NP-40, 0.5% Deoxycholate, 0.1% SDS) supplemented with 10 mM EDTA, 1×Halt protease and phosphatase inhibitors (Thermo Scientific). Protein lysates (approximately 20 µg) was resolved on 4-12% Bolt Bis-Tris precasted gels with MES running buffer (Life Technologies), transferred to nitrocellulose membranes using Trans-Blot Turbo Transfer System (Bio-Rad) and detected with antibodies targeting phosphorylated ALK Y1604 (Cell Signaling Technology), total ALK (Cell Signaling Technology), phosphorylated ROS1 and total ROS1 (Cell Signaling Technology), phosphorylated TRK A/B (Cell Signaling Technology), total TRKA antibody (Santa Cruz Biotechnology), phosphorylated STAT3 and STAT5, total STAT3 and STAT5 (Cell Signaling Technology), phosphorylated AKT (Cell Signaling Technology), total AKT (Cell Signaling Technology), phosphorylated ERK (Cell Signaling Technology), total ERK (Cell Signaling Technology) and Tubulin (Sigma). Antibodies were typically incubated overnight at 4° C. with gentle shake, followed by washes and incubation with the appropriate HRP-conjugated secondary antibodies. Membranes were incubated with chemiluminescent substrate for 5 min at room temperature (SuperSignal West Femto, Thermo Scientific). The chemiluminescent images were acquired with a C-DiGit Imaging System (LI-COR Biosciences). The relative density of the chemiluminescent bands were quantified via Image Studio Digits from LICOR. The half inhibitory concentration ($IC_{50}$) value is calculated using non-linear regression analysis through GraphPad Prism software (GraphPad, Inc., San Diego, CA).

NSCLC cell line H2228 (harboring endogenous EML4-ALK fusion gene) was cultured in RPMI medium supplemented with 10% fetal bovine serum and 100 U/mL of penicillin/streptomycin. Ba/F3 and NIH3T3 cells stably expressing ROS1, or TRKA, or TRKB, or TRKC (WT or mutant) were cultured as mentioned above. Half a million cells per well were seeded in 24 well plate for 24 hrs, and then treated with compounds for 4 hours. Cells were collected after treatment and lysed in RIPA buffer (50 mM Tris, pH 7.4, 150 mM NaCl, 1% NP-40, 0.5% Deoxycholate, 0.1% SDS) supplemented with 10 mM EDTA, 1×Halt protease and phosphatase inhibitors (Thermo Scientific). Protein lysates (approximately 20 µg) was resolved on 4-12% Bolt Bis-Tris precasted gels with MES running buffer (Life Technologies), transferred to nitrocellulose membranes using Trans-Blot Turbo Transfer System (Bio-Rad) and detected with antibodies targeting phosphorylated phosphorylated ROS1 and total ROS1 (Cell Signaling Technology), phosphorylated TRK A/B (Cell Signaling Technology), total TRKA antibody (Santa Cruz Biotechnology), phosphorylated SRC Y416 (Cell Signaling Technology), total SRC (Cell Signaling Technology), phosphorylated FAK Y576/577 (Cell Signaling Technology), total FAK (Cell Signaling Technology), phosphorylated paxillin Y118 (Cell Signaling Technology), total paxillin (Cell Signaling Technology), phosphorylated EGFR and total EGFR, CD44, and Tubulin (Sigma). Antibodies were typically incubated overnight at 4° C. with gentle shake, followed by washes and incubation with the appropriate HRP-conjugated secondary antibodies. Membranes were incubated with chemiluminescent substrate for 5 min at room temperature (SuperSignal West Femto, Thermo Scientific). The chemiluminescent images were acquired with a C-DiGit Imaging System (LI-COR Biosciences). The relative density of the chemiluminescent bands were quantified via Image Studio Digits from LICOR. The half inhibitory concentration ($IC_{50}$) value is calculated using non-linear regression analysis through GraphPad Prism software (GraphPad, Inc., San Diego, CA).

Apoptosis/Caspase Activity Assays.

Karpas-299 cells were maintained in RPMI medium supplemented with 10% fetal bovine serum and antibiotics. Five hundred thousand cells per well were seeded in 12-well plate and various concentration of compounds were introduced and incubated for 48 hrs. The cells were then collected and lysed in a lysis buffer (20 mM HEPES, 150 mM NaCl, 10 mM KCl, 5 mM EDTA, 1% NP40) supplemented with Halt protease and phosphatase inhibitors (Thermo Scientific). For caspase assays, approximately 20 µg of cell lysate were incubated with 20 µl of caspase-3 glo reagent (Promega), and the enzyme activity was measured by the release of luminescence after 20 min incubation at 37° C. For western blotting, cell lysate were boiled and analyzed by SDS-PAGE/immunoblotting using anti-caspase-3 (Cell Signaling Technology), anti-PARP (Cell Signaling Technology), or anti-actin (Cell Signaling Technology) antibodies. Antibodies were typically incubated overnight at 4° C. with gentle shake, followed by washes and incubation with the appropriate HRP-conjugated secondary antibodies. Membranes were incubated with chemiluminescent substrate for 5 min at room temperature (SuperSignal West Femto, Thermo Scientific), and the chemiluminescent images were obtained with a C-DiGit Imaging System (LI-COR Biosciences).

Scratch Wound Healing Assay

HT1080 or HCC78 cells in RPMI medium supplemented with 10% fetal bovine serum and antibiotics were seeded in 24-well plate. After 12-24 hours, confluent cell monolayers were gently scraped with a sterile pipette tip to form a scratch. The plates were washed with fresh medium, and the cells were incubated with medium alone or medium containing various concentration of compounds. After 12-24 hours, the plates were examined and recorded by an EVOS FL microscopy (Life Technology) to monitor resealing of the cell monolayer.

In-Vivo Methods

Cell Lines

Cell lines were cultured using standard techniques in DMEM or RPMI-1640 medium (Corning, Inc) with 10% fetal bovine serum (Thermo Fisher Scientific, Inc) at 37° C. in a humidified atmosphere with 5% $CO_2$. For implantation, cells were harvested and pelleted by centrifugation at 250 g for 2 minutes. Cells were washed once and resuspended in serum-free medium, with 50% matrigel (v/v) as needed.

Subcutaneous Xenograft Models in Immune Compromised Mice

Female athymic nude mice and SCID/Beige mice (5-8 weeks of age) were obtained from Charles River Laboratory and were housed in Innovive IVC disposable cages on HEPA filtered ventilated racks with ad libitum access to rodent chow and water. Five million cells in 100 µL serum-free medium were implanted subcutaneously in the right flank region of the mouse. Karpas299 cells were implanted into the SCID/Beige mice. KM12 cells, NIH3T3 EML4-ALK wild type mutant cells, and NIH3T3 SCD4-ROS1 wild type mutant cells were implanted into the athymic nude mice, respectively. All models except KM12 were implanted with 50% matrigel (Corning, Inc) in the medium. Tumor size and body weight were measured on designated days. Tumor size was measured with an electronic caliper and tumor volume was calculated as the product of length*width$^2$*0.5. Mice were randomized by tumor size into treatment groups when tumor volume reached about 100-200 mm$^3$ and Compound 1 were administered orally (BID) at determined dosage.

Female athymic nude mice and SCID/Beige mice (5-8 weeks of age) were obtained from Charles River Laboratory and were housed in Innovive IVC disposable cages on HEPA filtered ventilated racks with ad libitum access to rodent chow and water. Five million cells in 100 µL serum-free medium were implanted subcutaneously in the right flank region of the mouse. Ba/F3 EML4-ALK wild type and G1202R mutant cells, Ba/F3 CD74-ROS1 wild type and G2032R mutant cells were implanted into the SCID/Beige mice. NIH3T3 CD74-ROS1 G2032 mutant cells, NIH3T3 LMNA-TRKA wild type and G595R mutant cells were implanted into the athymic nude mice, respectively. All models were implanted with 50% matrigel (Corning, Inc) in the medium. Tumor size and body weight were measured on designated days. Tumor size was measured with an electronic caliper and tumor volume was calculated as the product of length*width$^2$*0.5. Mice were randomized by tumor size into treatment groups when tumor volume reached about 100-200 mm$^3$ and Compound 1 were administered orally (BID) at determined dosage.

Tumor Processing and Immunoblotting for In Vivo Pharmacodynamic Studies

Mice bearing xenograft tumors were humanely euthanized and tumors were resected and snap frozen in liquid nitrogen and stored at −80° C. Frozen tumor samples were processed at 4° C. in 1×Cell Lysis Buffer (Cell Signaling Technologies) to extract proteins. SDS loading samples were prepared by adding one volume of 4×LDS Sample Buffer (Life Technologies, Inc) to three volumes of protein lysate. Tumor SDS protein samples were processed by SDS-PAGE and immunoblotted with rabbit anti-phosphorylated ALK and mouse anti-actin antibodies (Cell Signaling Technologies). The signals from immunoblot were detected by C-DiGit Blot Scanner from LI-COR and the signal intensity were quantified using the Image Studio Digit software (LI-COR).

Data and Results:

Example 4a: Kinase Binding Affinities and Enzymatic Kinase Activities of Compound 1

The kinase binding affinity of Compound 1 was screened at DiscoveRx in a panel of 460 kinases followed by the determination of the $K_d$ for the hits. Compound 1 demonstrated strong binding affinities with ALK, ROS1, TRKA/B/C, JAK2, SRC, FAK and ARK5 (Table 1). Furthermore, the enzymatic kinase inhibition activities of Compound 1 at 10 μM ATP concentration were determined at Reaction Biology, and the results of $IC_{50}$ were summarized in Table 1.

TABLE 1

| Target | ALK | ROS1 | TRKA | TRKB | TRKC | JAK2 | SRC | FAK | ARK5 |
|---|---|---|---|---|---|---|---|---|---|
| $K_d$ (nM) | 5.7 | 0.19 | 0.019 | 0.054 | 0.088 | 0.082 | 12.0 | 27 | 3.7 |
| $IC_{50}$ (nM) | 1.04 | 0.0706 | 0.826 | 0.0517 | 0.0956 | 1.04 | 5.29 | 6.96 | 4.46 |

Example 4b: Enzymatic Kinase Activities of Compound 1

The kinase binding affinity of Compound 1 was screened at DiscoveRx in a panel of 460 kinases. The kinase hits of compound 1 were further configured in the recombined enzymatic kinase inhibition assay using 10 μM ATP concentration at Reaction Biology, and the $IC_{50}$ results were summarized in Table 1b.

TABLE 1b

| Target | $IC_{50}$ (nM) at 10 μM ATP | Target | $IC_{50}$ (nM) at 10 μM ATP | Target | $IC_{50}$ (nM) at 10 μM ATP |
|---|---|---|---|---|---|
| TRKB | 0.05 | SNARK | 13.0 | JAK3 | 50 |
| ROS1 | 0.07 | HCK | 16.4 | EPHA8 | 50.2 |
| TRKC | 0.1 | IRR | 18.1 | IGFR | 111 |
| TRKA | 0.83 | LCK | 18.6 | PLK4 | 126 |
| ALK | 1.04 | JAK1 | 19 | AXL | 149 |
| JAK2 | 1.04 | TYK2 | 21.6 | MARK3 | 512 |
| FYN | 1.05 | LTK | 21.8 | | |
| LYN | 1.66 | DDR2 | 23 | | |
| YES | 2.15 | BTK | 23.7 | | |
| FGR | 3.05 | TNK2 | 24.1 | | |
| TXK | 3.17 | EPHA1 | 25.0 | | |
| ARK5 | 4.46 | BLK | 32.3 | | |
| SRC | 5.3 | GRK7 | 35.2 | | |
| DDR1 | 5.7 | PYK2 | 39.9 | | |
| FAK | 6.96 | RET | 47.1 | | |

Example 5: Assessment of Compound 1 Activity Against a Panel of ALK Mutations

Compound 1 was evaluated against ALK resistant mutations in enzymatic kinase assays with 10 μM ATP concentration at Reaction Biology, Inc. The results were summarized in Table 2. Potent inhibition by Compound 1 was observed among wild type and mutant ALKs and ROSIs.

TABLE 2

| | NPM-ALK | ALK Wild | ALK T1151M | ALK 1151Tins | ALK L1152R | ALK C1156Y | ALK F1174L |
|---|---|---|---|---|---|---|---|
| $IC_{50}$ (nM) | 1.23 | 1.04 | 0.49 | 2.16 | 1.23 | 0.93 | 1.46 |

| | ALK F1174S | ALK L1196M | ALK G1202R | ALK S1206R | ALK G1269A | ALK G1269S | ALK R1275Q |
|---|---|---|---|---|---|---|---|
| $IC_{50}$ (nM) | 1.02 | 1.08 | 1.21 | 0.53 | 5.5 | 14.1 | 2.79 |

| | ROS1 WT | ROS1 G2032R | ROS1-TPM3 |
|---|---|---|---|
| $IC_{50}$ (nM) | 0.0706 | 0.456 | 0.113 |

Example 6: Compound 1 Potently Inhibited Cell Proliferation in Primary Cell Lines with Oncogenic Fusion or Mutated Genes of ALK, ROS1, TRKA or JAK2

ALK fusions are major malignancy drivers in multiple cancer types and cancer cell lines, including lymphoma cell line Karpas-299 harboring NPM-ALK fusion gene, non-small cell lung cancer cell line H2228 harboring EML4-ALK fusion gene, non-small cell lung cancer cell line HCC78 harboring SLC34A2-ROS1 fusion gene, colorectal cancer cell line KM12 harboring TPM3-TRKA fusion gene, and leukemia cell line SET-2 harboring JAK2 V617F mutation. The anti-proliferating activities of Compound 1 on these cell lines were evaluated and the results were summarized in Table 3.

Example 7: Evaluation of Compound 1 Activity Against a Panel of ALK Gene Mutations in Engineered Ba/F3 Cell Lines Furthermore, we used Ba/F3 cells engineered to express wild type EML4-ALK fusion gene and mutant EML4-ALKs. The growth of Ba/F3 cells is dependent on interleukin-s (IL-3). With ectopic expression of EML4-ALK gene, Ba/F3 cell growth becomes IL-3 independent, and relies on the kinase activity of the oncogenic fusion ALK. Compound 1 potently inhibited the cell proliferation of various Ba/F3 cell lines with engineered expression of wild and mutant EML4-ALKs, and the results were summarized in Table 3.

The inhibition of cell proliferation of Ba/F3 TPR-ALK and Ba/F3 TPR-ALK L1196M cell lines were performed at Advanced Cellular Dynamics. Compound 1 demonstrated potent inhibition in both cell lines (Table 3).

Example 8: Evaluation of Compound 1 Activity Against ROS1 in Engineered Ba/F3 Cell Lines Ba/F3 cells were engineered to express the oncogenic SDC4-ROS1, SDC4-ROS1$^{G2032R}$, CD74-ROS1, and CD74-ROS1$^{G2032R}$ fusion genes, respectively. The engineered Ba/F3 cells with fusion ROS1 genes were used to examine the inhibiting activity of Compound 1 on wild and mutant ROS1 fusion genes. The results of cell growth inhibition were summarized in Table 3.

Ba/F3 cells were engineered to express the oncogenic CD74-ROS1$^{L2026M}$, and CD74-ROS1$^{D2033N}$ fusion genes, respectively. The engineered Ba/F3 cells with fusion ROS1 genes were used to examine the inhibiting activity of Compound 1. The results of cell growth inhibition were summarized in Table 3.

Ba/F3 cells were engineered to express the oncogenic LMNA-TRKA and LMNA-TRKA$^{G595R}$ fusion genes, respectively. The engineered Ba/F3 cells with fusion TRKA genes were used to examine the inhibiting activity of Compound 1. The results of cell growth inhibition were summarized in Table 3.

Ba/F3 cells were engineered to express the oncogenic TEL-TRKB (also named as ETV6-TRKB) and TEL-TRKB$^{G639R}$ fusion genes, respectively. The engineered Ba/F3 cells with fusion TRKB genes were used to examine the inhibiting activity of Compound is. The results of cell growth inhibition were summarized in Table 3.

Ba/F3 cells were engineered to express the oncogenic TEL-TRKC (also named as ETV6-TRKC), and TEL-TRKC$^{G623R}$ fusion genes, respectively. The engineered Ba/F3 cells with fusion TRKC genes were used to examine the inhibiting activity of Compound 1. The results of cell growth inhibition were summarized in Table 3.

TABLE 3

| Assays | $IC_{50}$ (nM) |
|---|---|
| Cell proliferation of Karpas-299 cell line | 23.7 |
| Cell proliferation of NCI-H2228 cell line | 73 |
| Cell proliferation of HCC78 cell line | 0.3 |
| Cell proliferation of KM12 cell line | 0.3 |
| Cell proliferation of SET-2 cell line | 169 |
| Cell proliferation of Ba/F3 EML4-ALK wild type cell line | 17.8 |
| Cell proliferation of Ba/F3 EML4-ALK G1202R cell line | 20.5 |
| Cell proliferation of Ba/F3 EML4-ALK L1152P cell line | 85 |
| Cell proliferation of Ba/F3 EML4-ALK L1196M cell line | 50 |
| Cell proliferation of Ba/F3 EML4-ALK F1174C cell line | 54 |
| Cell proliferation of Ba/F3 EML4-ALK C1156Y cell line | 98 |
| Cell proliferation of Ba/F3 TPR-ALK wild type cell line | 12 |
| Cell proliferation of Ba/F3 TPR-ALK L1196M cell line | 13.4 |
| Cell proliferation of Ba/F3 CD74-ROS1 wild type cell line | 0.2 |
| Cell proliferation of Ba/F3 CD74-ROS1 G2032R cell line | 8.4 |
| Cell proliferation of Ba/F3 SDC4-ROS1 wild type cell line | 0.2 |
| Cell proliferation of Ba/F3 SDC4-ROS1 G2032R cell line | 5 |
| Cell proliferation of Ba/F3 + IL3 parental | 1236 |
| Cell proliferation of Ba/F3 CD74-ROS1 L2026M cell line | 5 |
| Cell proliferation of Ba/F3 CD74-ROS1 D2033N cell line | 0.2 |
| Cell proliferation of Ba/F3 LMNA-TRKA cell line | 0.2 |
| Cell proliferation of Ba/F3 LMNA-TRKA G595R cell line | 0.4 |
| Cell proliferation of Ba/F3 TEL-TRKB (ETV6-TRKB) cell line | 0.2 |
| Cell proliferation of Ba/F3 TEL-TRKB (ETV6-TRKB) G639R cell line | 0.6 |

TABLE 3-continued

| Assays | IC$_{50}$ (nM) |
|---|---|
| Cell proliferation of Ba/F3 TEL-TRKC (ETV6-TRKC) cell line | 0.2 |
| Cell proliferation of Ba/F3 TEL-TRKC (ETV6-TRKC) G623R cell line | 3 |

Example 9: Mechanism of Action of Compound 1 in Cells

The pharmacodynamic inhibiting activity of Compound 1 on ALK, ROS1, TRKA and SRC, and the corresponding downstream signaling in cells was evaluated, and the results were summarized in Table 4. Compound 1 caused suppression of ALK autophosphorylation as well as the downstream STAT3 and AKT phosphorylation at IC$_{50}$s of around 1-3 nM in Karpas-299 cell line, which harbors NPM-ALK fusion gene. Compound 1 inhibited ROS1 autophosphorylation as well as the downstream STAT3 and AKT phosphorylation at IC$_{50}$s around 1-3 nM in HCC78 cell line, which harbors SLC34A2-ROS1 fusion gene. Compound 1 inhibited TRKA autophosphorylation as well as the downstream AKT and ERK phosphorylation at IC$_{50}$s around 0.3 nM in KM12 cell line, which harbors TPM3-TRKA fusion gene. Compound 1 inhibited STAT5 phosphorylation at IC$_{50}$ around 158 nM in SET-2 cell line, which harbors JAK2 V617F mutation. Compound 1 inhibited autophosphorylation of ALK with IC$_{50}$ of 20-30 nM in Ba/F3 engineered stable cell lines encoding wild type or G1202R mutant EML4-ALK v1 fusion genes. Compound 1 inhibited autophosphorylation of ROS1 in Ba/F3 engineered stable cell lines encoding wild type or G2032R mutant CD74-ROS1 or SDC4-ROS1 fusion genes. The pharmacodynamic inhibiting activity of Compound 1 on TRKA, TRKB, TRKC, and FAK signaling in cells was evaluated, and the results were summarized in Table 4a. Compound 1 inhibited FAK phosphorylation as well as the SRC substrate paxillin phosphorylation at IC$_{50}$ around 103 nM in NCI-H2228 cell line, which harbors EML4-ALK fusion gene with upregulated SRC and FAK signaling. Compound 1 inhibited autophosphorylation of ROS1 in Ba/F3 engineered stable cell lines encoding L2026M, or D2033N mutant CD74-ROS1 fusion genes. Compound 1 inhibited autophosphorylation of TRKA in NIH3T3 engineered stable cell lines encoding wild type or G595R mutant LMNA-TRKA fusion genes. Compound 1 inhibited autophosphorylation of TRKB in NIH3T3 engineered stable cell lines encoding wild type or G639R mutant TEL-TRKB, also named as ETV6-TRKB fusion genes.

TABLE 4

| Assays | IC$_{50}$ (nM) |
|---|---|
| ALK phosphorylation of Karpas-299 cell line | 0.9 |
| ALK phosphorylation of NCI-H2228 cell line | 5.8 |
| ALK phosphorylation of Ba/F3 EML4-ALK WT cell line | 29.9 |
| ALK phosphorylation of Ba/F3 EML4-ALK G1202R cell line | 18.4 |
| ROS1 phosphorylation of HCC78 cell line | 2 |
| ROS1 phosphorylation of Ba/F3 CD74-ROS1 WT cell line | 0.3 |
| ROS1 phosphorylation of Ba/F3 CD74-ROS1 G2032R cell line | 3 |
| ROS1 phosphorylation of Ba/F3 SDC4-ROS1 WT cell line | 0.5 |
| ROS1 phosphorylation of Ba/F3 SDC4-ROS1 G2032R cell line | 2 |
| TRKA phosphorylation of KM12 cell line | 0.35 |
| STAT5 phosphorylation of SET-2 cell line | 158 |
| SRC phosphorylation of H2228 cell line | 102 1 |

TABLE 4-continued

| Assays | IC$_{50}$ (nM) |
|---|---|
| ROS1 phosphorylation of Ba/F3 CD74-ROS1 L2026M cell line | 10 |
| ROS1 phosphorylation of Ba/F3 CD74-ROS1 D2033N cell line | <1 |
| TRKA phosphorylation of NIH3T3 LMNA-TRKA cell line | 0.01 |
| TRKA phosphorylation of NIH3T3 LMNA-TRKA G595R cell | 0.1 |
| TRKB phosphorylation of NIH3T3 TEL-TRKB cell line | <0.1 |
| TRKB phosphorylation of NIH3T3 TEL-TRKB G639R cell | 1 |
| FAK phosphorylation of NCI-H2228 cell line | 100 |

Compound 1 increased the number of apoptotic Karpas-299 cells. After 48 hours treatment with Compound 1, Karpas-299 cells were lysed and evaluated with the caspase 3/7 cleavage caspase 3 glo assay or PARP in western blotting assay. The results were presented in FIG. 1.

Compound 1 inhibited HCC78 or HT1080 cell migration after 12 hour treatment in the scratch wound healing assays. The results were presented in FIG. 2

Compound 1 Down-Regulated EGFR Expression in H2228 Cells

Figure 3:
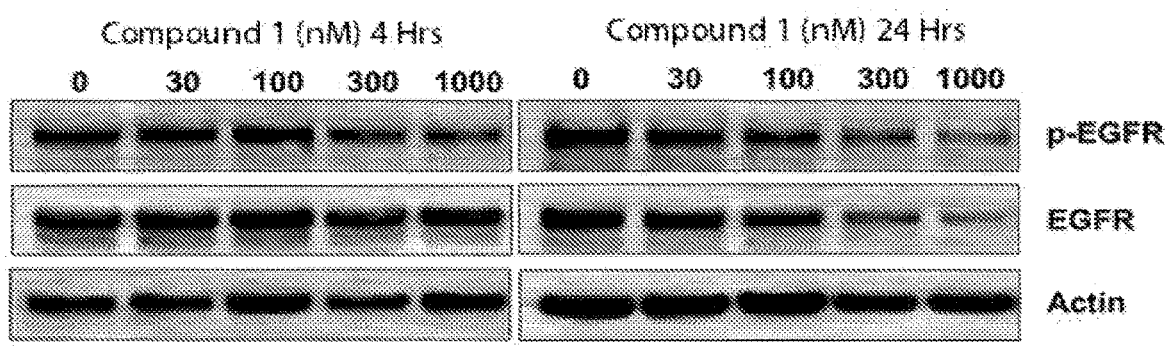
FIG. 3 shows gels demonstrating that Compound 1 downregulates EGFR expression.

The activation of SRC kinase activity upregulates RTK expression level, leading to the bypass signaling pathway resistance. The inhibition of SRC will result in the down regulation of RTKs. Compound 1 down-regulated EGFR expression in a dose- and time-dependent manner as shown in FIG. 3.

Compound 1 Down-Regulated EGFR Expression in H2228 Cells

Figure 4:
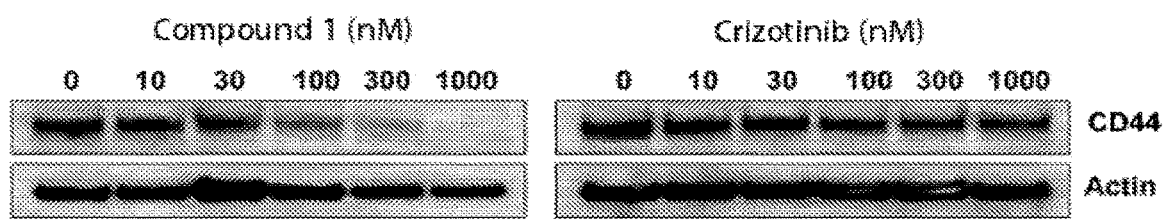
FIG. 4 shows gels demonstrating that Compound 1 downregulates CD44 expression as compared to the same experiment with crizotinib which does not show down-regulation of CD44 expression.

CD44 is a biomarker of cancer stemness. A high expression level of CD44 was discovered in H2228 cells. Compound 1 suppressed CD44 expression level in H2228 cells in a concentration-dependent manner after 48 hours treatment as shown in FIG. 4, indicating that compound 1 has the potential to inhibit cancer stemness.

In-Vivo Studies

Antitumor Efficacy of Compound 1 in Xenograft Tumor Models

The antitumor efficacy of Compound 1 was evaluated in several tumor xenograft models representing cancer populations in which dysregulation of ALK, ROS1 or TRKA is implicated.

Example 10: Karpas 299 ALCL Model

Figure 5:
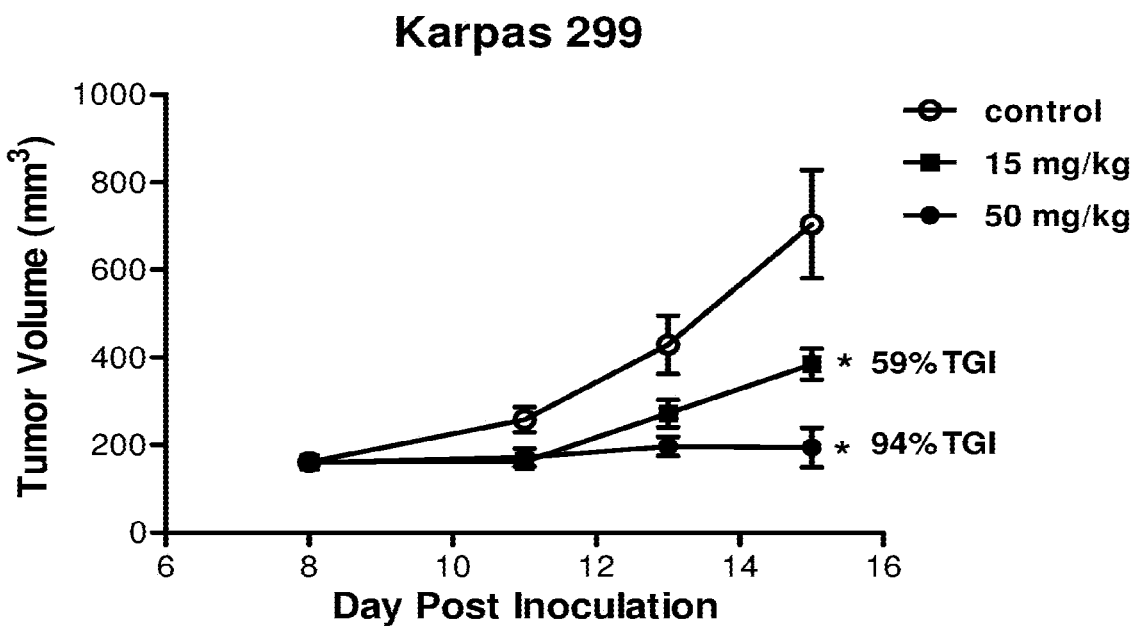
FIG. 5 shows the effect of Compound 1 on tumor growth in the Karpas-299 in vivo model at various doses, (○) control, (■) 15 mg/kg, (■) 50 mg/kg.
Figure 6:
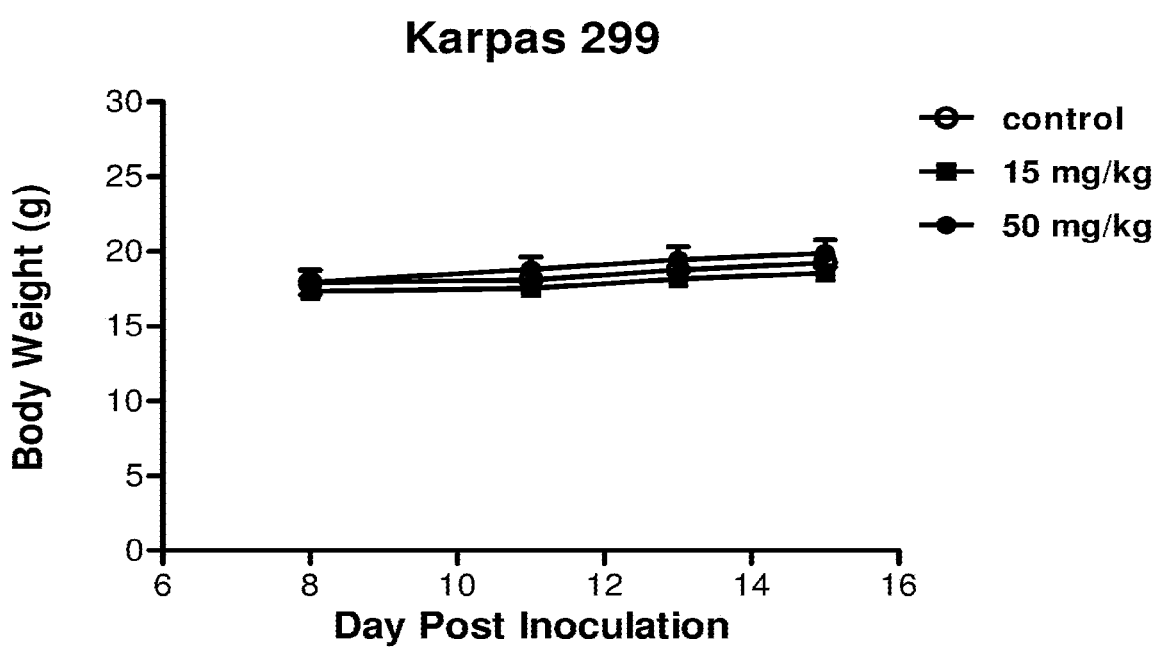
FIG. 6 shows the stability of animal body weight in the Karpas-299 in vivo model following administration of Compound 1 at various doses, (○) control, (■) 15 mg/kg, (●) 50 mg/kg.

The NPM-ALK fusion gene in Karpas 299 cells is proved as the driver for tumor growth. SCID/Beige mice bearing Karpas 299 tumors (at the average tumor size of 160 mm$^3$) were dosed with Compound 1 orally BID for seven days (FIG. 5). The control group of mice were given vehicle only. Tumor volume (TMV) was measured by caliper on the indicated days and is shown at mean±sem in FIG. 5. An * denotes that the mean TMVs are significantly lower in the treated group compared to that of the control group (p<0.05) as determined by two-way repeated ANOVA followed by post hoc analysis. Tumor growth inhibition (TGI) was calculated as $100\% * \{1 - [(TMV_{Treated\ Last\ Day\ of\ Treatment} - TMV_{Treated\ First\ Day\ of\ Treatment}) / (TMV_{Control\ on\ Last\ Day\ of\ Treatment} - TMV_{Control\ on\ First\ Day\ of\ Treatment})]\}$ when $TMV_{Treated\ Last\ Day\ of\ Treatment} \geq TMV_{Treated\ First\ Day\ of\ Treatment}$. In the case of $TMV_{Treated\ Last\ Day\ of\ Treatment} < TMV_{Treated\ First\ Day\ of\ Treatment}$, tumor regression (REG) was calculated as $100\% * (1 - TMV_{Treated\ Last\ Day\ of\ Treatment} / TMV_{Treated\ First\ Day\ of\ Treatment})$. In this study, Compound 1 demonstrated the ability to inhibit tumor growth at 59% and 94% at the dosages of 15 mg/kg and 50 mg/kg BID, respectively. In addition, 4 of 8 mice in the 50 mg/kg treatment group exhibited tumor regression. Body weight of the mice were measured on the designated days of the mice and no body weight loss was observed in the Compound 1 treatment groups (FIG. 6).

Example 11: NIH3T3 EML4-ALK Wildtype (WT) Model

Figure 7:
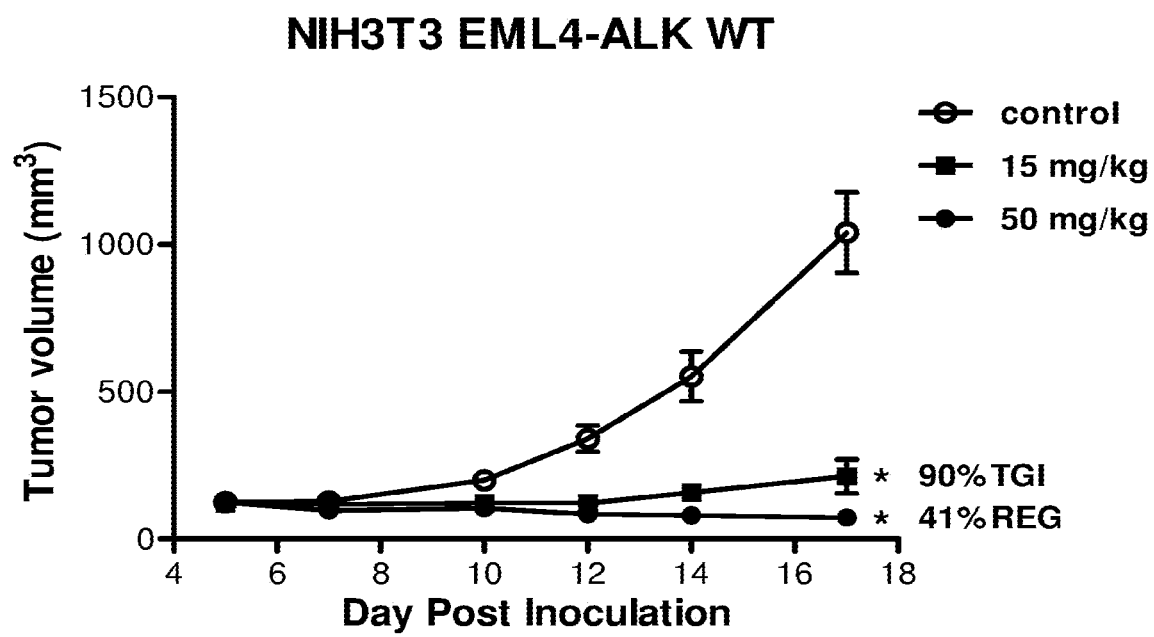
FIG. 7 shows the effect of Compound 1 on tumor growth in the NIH3T3 EML4-ALK WT in vivo model at various doses, (○) control, (■) 15 mg/kg, (■) 50 mg/kg.
Figure 8:
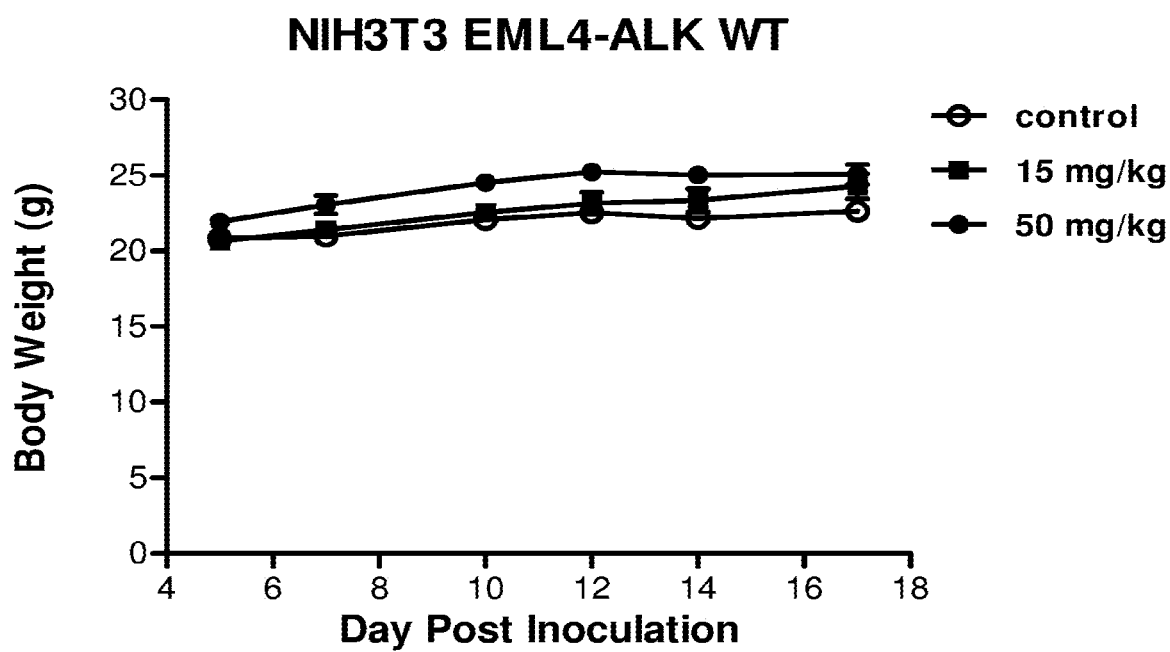
FIG. 8 shows the stability of animal body weight in the NIH3T3 EML4-ALK WT in vivo model following administration of Compound 1 at various doses, (○) control, (■) 15 mg/kg, (●) 50 mg/kg.

Athymic nude mice bearing the NIH3T3 EML4-ALK WT tumors (at the average tumor size of 120 mm$^3$) were dosed with Compound 1 orally BID for 12 days (FIG. 7). The control group of mice were given vehicle only. Tumor volume was measured by caliper on the indicated days and is shown as mean±sem in FIG. 7. An * denotes that the mean tumor volumes are significantly lower in the treated group compared to that of the control group (p<0.05) as determined by two-way repeated ANOVA followed by post hoc analysis. In this study, treatment of Compound 1 at 50 mg/kg/BID resulted in 41% tumor regression, with 8 of 8 mice exhibited tumor regression. Compound 1 at the dosage of 15 mg/kg/BID demonstrated the ability to inhibit tumor growth at a TGI of 90%, with 2 of 8 mice exhibited tumor regression. Body weight of the mice were measured on the designated days of the mice and no body weight loss was observed in the Compound 1 treatment groups (FIG. 8).

Example 12: NIH3T3 SDC4-ROS1 WT Model

Figure 9:
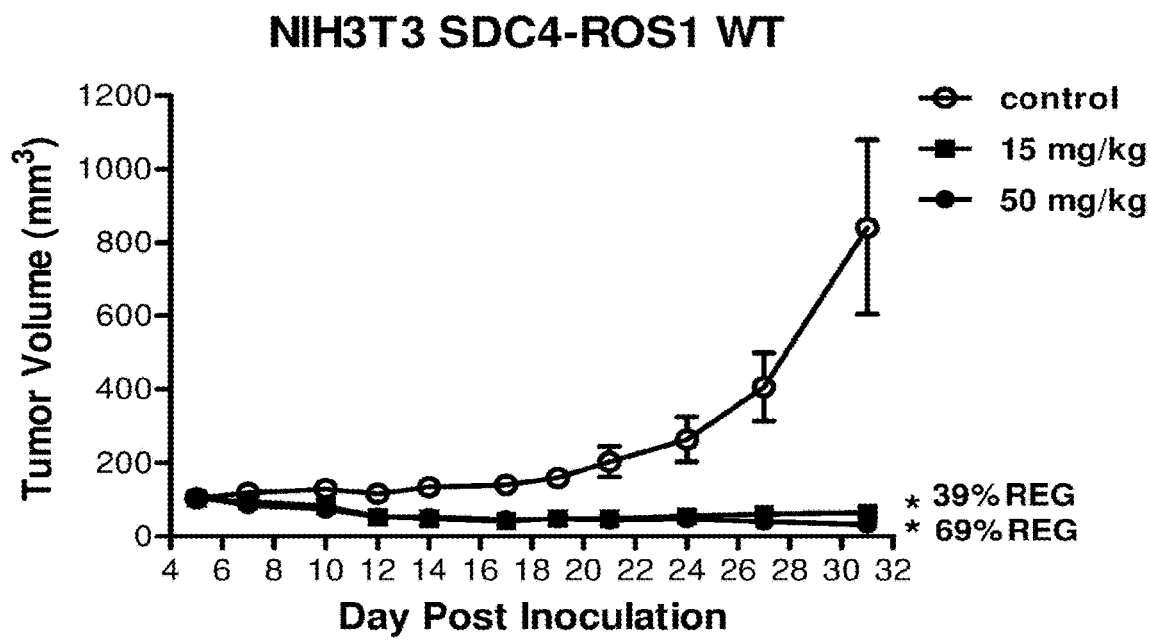
FIG. 9 shows the effect of Compound 1 on tumor growth in the NIH3T3 SDC4-ROS1 WT in vivo model at various doses, (○) control, (■) 15 mg/kg, (●) 50 mg/kg.

The SDC4-ROS1 fusion gene is considered as the driver for tumor progression in NSCLC. Athymic nude mice bearing the NIH3T3 SDC4-ROS1 WT tumors (at the average tumor size of 100 mm$^3$) were dosed with Compound 1 orally BID for 26 days (FIG. 9). The control group of mice were given vehicle only. Tumor volume was measured by caliper on the indicated days and is shown at mean±sem in FIG. 9. An * denotes that the mean tumor volumes are significantly less in the treated group compared to that of the control group (p<0.05) as determined by two-way repeated ANOVA followed by post hoc analysis. In this study, treatment of Compound 1 at 50 mg/kg resulted in 69% tumor regression, with 7 of 7 mice exhibited tumor regression. Mice in the 15 mg/kg Compound 1 group also demonstrated 39% tumor regression, with 7 of 8 mice in this group exhibited tumor regression.

Example 13: KM12 Colorectal Cancer Model

Figure 10:
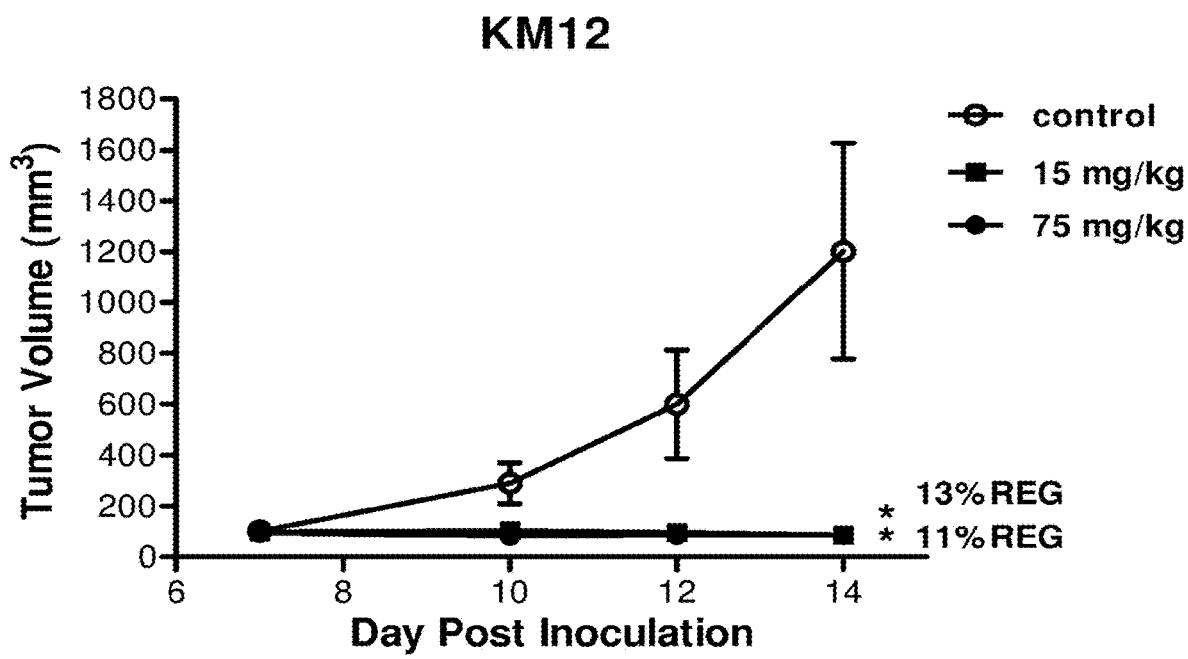
FIG. 10 shows the effect of Compound 1 on tumor growth in the KM12 in vivo model at various doses, (○) control, (■) 15 mg/kg, (●) 75 mg/kg.
Figure 11:
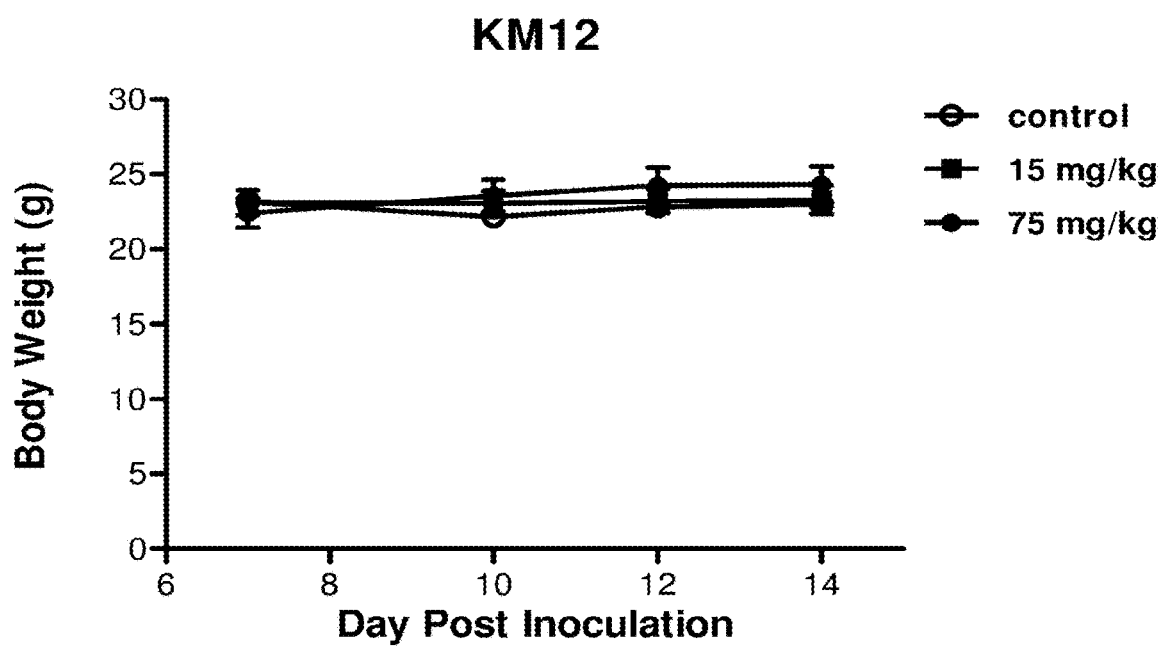
FIG. 11 shows the stability of animal body weight in the KM12 in vivo model following administration of Compound 1 at various doses, (○) control, (■) 15 mg/kg, (●) 75 mg/kg.

The aberrant activity of the TPM3-TRKA is considered as the underlying driver for tumor growth in the KM12 model. Athymic nude mice bearing the KM12 tumors (at the average tumor size of 100 mm$^3$) were dosed with Compound 1 orally BID for seven days (FIG. 10). Tumor volume was measured by caliper on the indicated days and is shown at mean±sem in FIG. 10. An * denotes that the mean tumor volumes are significantly lower in the treated group compared to that of the control group (p<0.05) as determined by two-way repeated ANOVA followed by post hoc analysis. In this study, Compound 1 at the dosage of 15 mg/kg and 75 mg/kg resulted in 13% and 11% tumor regression, respectively. In the 15 mg/kg group, 8 of 8 mice exhibited tumor regression. In the 75 mg/kg group, 5 of 8 mice exhibited tumor regression. No loss of body weight were observed in mice treated with Compound 1 compared to those with vehicle control (FIG. 11).

Example 14: Relationship of ALK Inhibition to Anti-Tumor Efficacy Following Oral Administration of Compound 1

Figure 12:
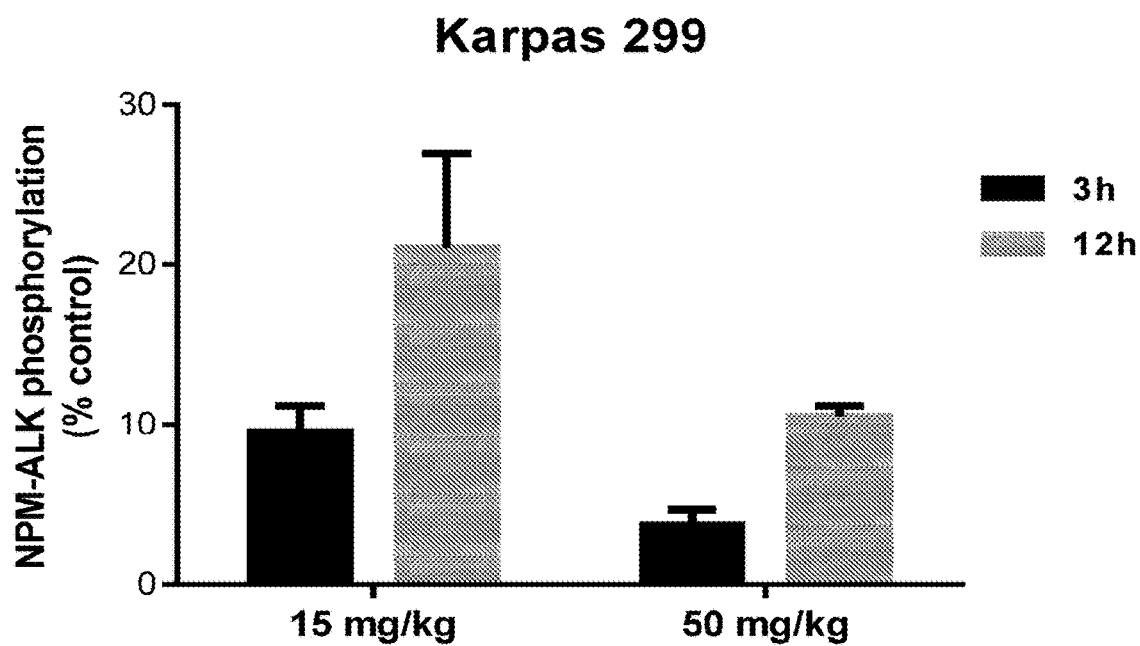
FIG. 12 shows the inhibition of NPM-ALK phosphorylation by Compound 1 in the Karpas-299 in vivo model.

To evaluate the effect of Compound 1 on the inhibition of ALK phosphorylation, Karpas 299 tumors were harvested at either 3 hour or 12 hour after last dose of Compound 1 in a repeated dosing study (15 mg/kg or 50 mg/kg, BID for seven days). The level of ALK phosphorylation was determined by immunoblotting combined with signal quantification by the Image Studio Digit Software. The ability of Compound 1 to inhibit ALK phosphorylation was illustrated in FIG. 12. At the dose of 50 mg/kg, ALK phosphorylation was reduced to <5% of the control level at 3 hours post oral administration of Compound 1 and was maintained at about 10% of the control level at 12 hours post dosing. This level of phosphorylation inhibition corresponds to 94% TGI. At the dose of 15 mg/kg, ALK phosphorylation was reduced to <10% of the control level at 3 hours post oral administration and was maintained at about 21% of the control level at 12 hours post dosing. This level of ALK phosphorylation corresponds to 59% of TGI. These results support the link between inhibition of ALK, the target of Compound 1, and the degree of antitumor efficacy in a NPM-ALK-dependent tumor model.

Example 15: Dose Dependent Studies in KM12 Colorectal Cancer Model

Figure 13:
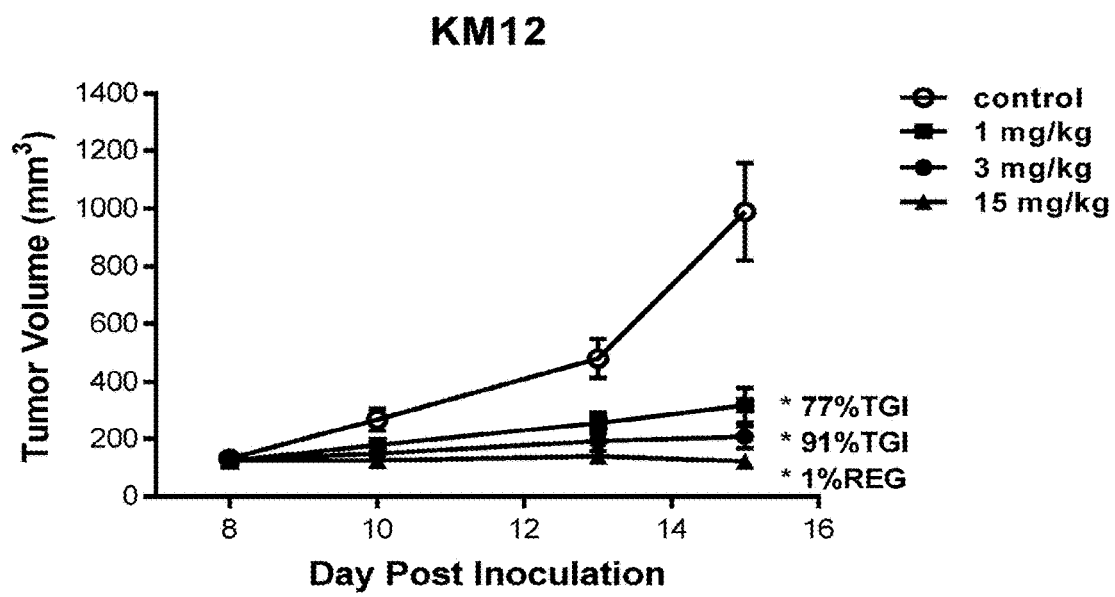
FIG. 13 shows the effect of Compound 1 on tumor growth in the KM12 in vivo model at various doses, (○) control, (■) 1 mg/kg, (●) 3 mg/kg, (▲) 15 mg/kg.
Figure 14:
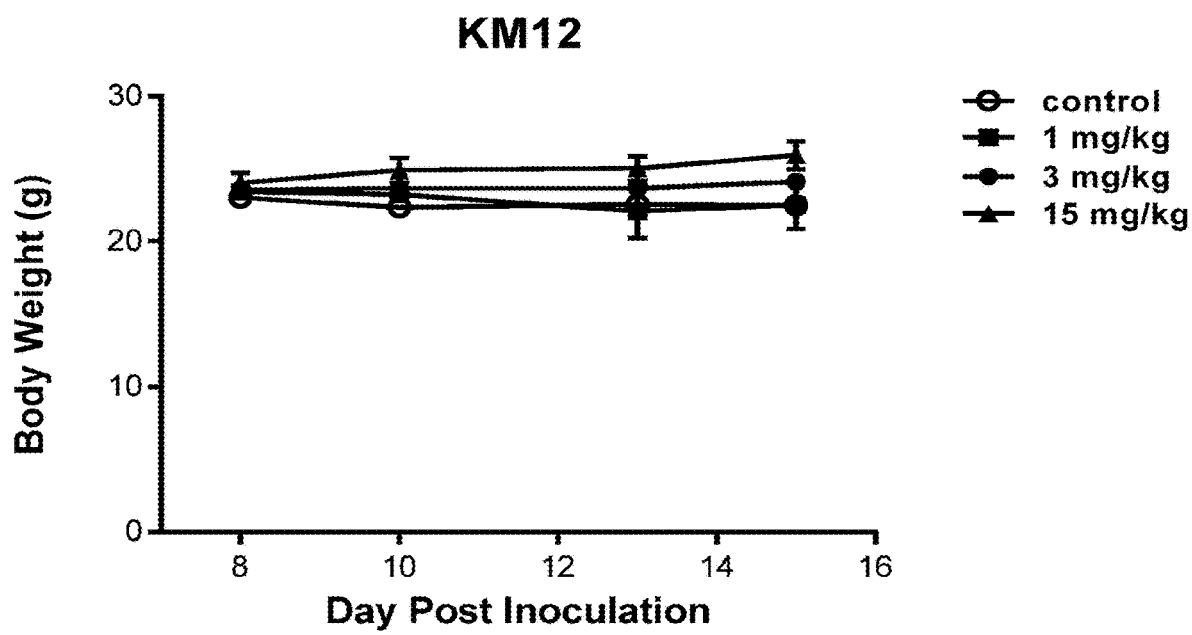
FIG. 14 shows the stability of animal body weight in the KM12 in vivo model following administration of Compound 1 at various doses, (○) control, (■) 1 mg/kg, (●) 3 mg/kg, (▲) 15 mg/kg.

To investigate the dose-dependent effect of Compound 1 on tumor inhibition in the KM12 colorectal cancer model, athymic nude mice bearing the KM12 tumors (at the average tumor size of 125 mm$^3$) were dosed with Compound 1 orally BID for seven days at dosages equal or lower than 15 mg/kg for seven days (FIG. 13). Tumor volume was measured by caliper on the indicated days and is shown at mean±sem in FIG. 13. An * denotes that the mean tumor volumes are significantly lower in the treated group compared to that of the control group (p<0.05) as determined by two-way repeated ANOVA followed by post hoc analysis. In this study, Compound 1 inhibited tumor growth in a dose-dependent manner. Treatment with Compound 1 at the dosage of 15 mg/kg resulted in 1% tumor regression, with 5 of 10 mice exhibiting tumor regression. Compound 1 at the dosage of 3 mg/kg demonstrated the ability to inhibit tumor growth at a TGI of 910%, with 2 of 10 mice exhibiting tumor regression. Compound 1 at the dosage of 1 mg/kg demonstrated the ability to inhibit tumor growth at a TGI of 77%. No loss of body weight were observed in mice treated with Compound 1 compared to those with vehicle control (FIG. 14).

Example 16: Ba/F3 EML4-ALK WT Model

Figure 15:
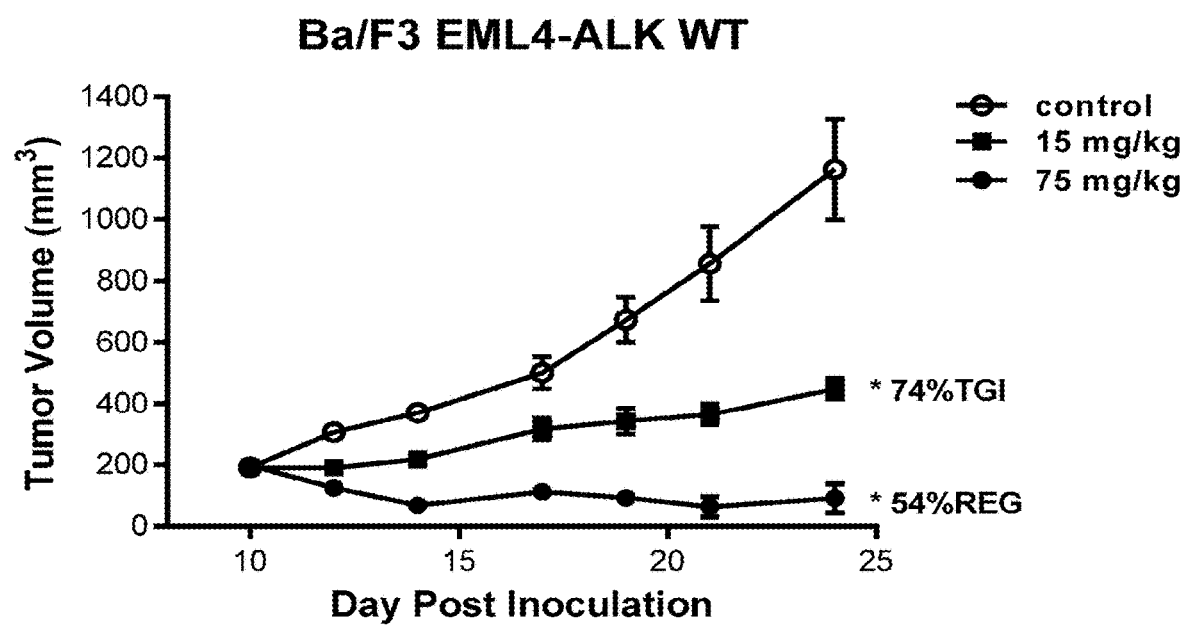
FIG. 15 shows the effect of Compound 1 on tumor growth in the Ba/F3 EML4-ALK WT in vivo model at various doses, (○) control, (■) 15 mg/kg, (●) 75 mg/kg.
Figure 16:
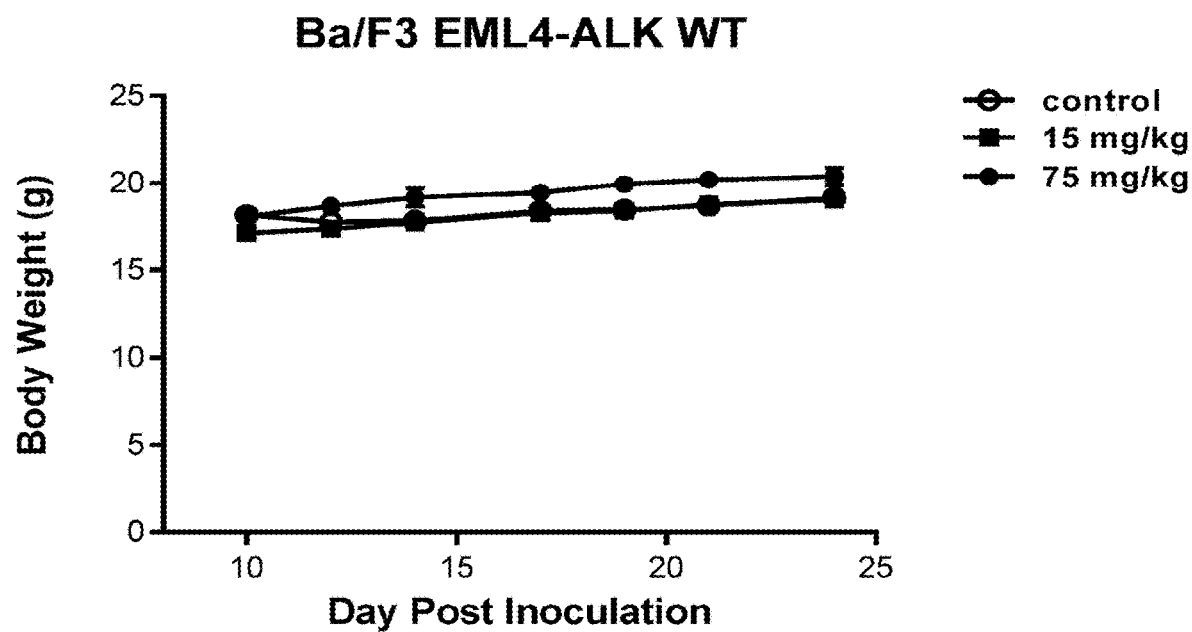
FIG. 16 shows the stability of animal body weight in the Ba/F3 EML4-ALK WT in vivo model following administration of Compound 1 at various doses, (○) control, (■) 15 mg/kg, (●) 75 mg/kg.

SCID/Beige mice bearing the Ba/F3 EML4-ALK WT tumors (at the average tumor size of 190 mm$^3$) were dosed with Compound 1 orally BID for 14 days (FIG. 15). The control group of mice were given vehicle only. Tumor volume was measured by caliper on the indicated days and is shown as mean±sem in FIG. 15. An * denotes that the mean tumor volumes are significantly lower in the treated group compared to that of the control group (p<0.05) as determined by two-way repeated ANOVA followed by post hoc analysis. In this study, treatment with Compound 1 at 75 mg/kg resulted in 54% tumor regression, with 6 of 8 mice exhibiting tumor regression. Compound 1 at the dosage of 15 mg/kg/BID demonstrated the ability to inhibit tumor growth at a TGI of 74%. Body weight of the mice were measured on the designated days and no body weight loss was observed in the Compound 1 treatment groups (FIG. 16).

Example 17: Ba/F3 EML4-ALK G1202R Model

Figure 17:
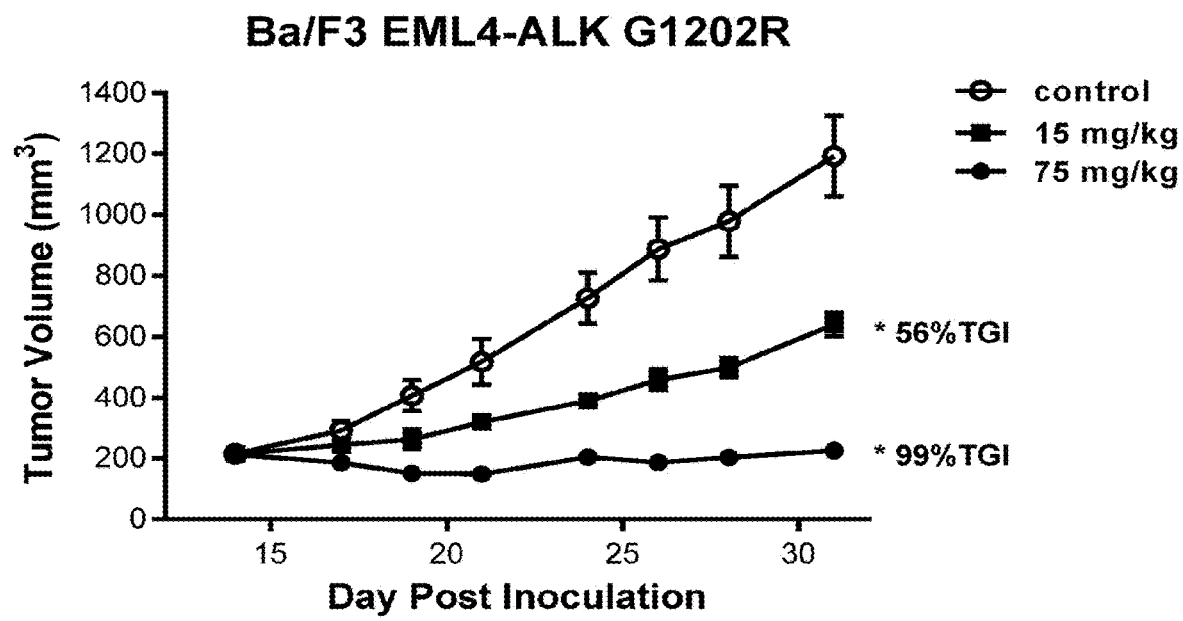
FIG. 17 shows the effect of Compound 1 on tumor growth in the Ba/F3 EML4-ALK G1202R in vivo model at various doses, (○) control, (■) 15 mg/kg, (●) 75 mg/kg.
Figure 18:
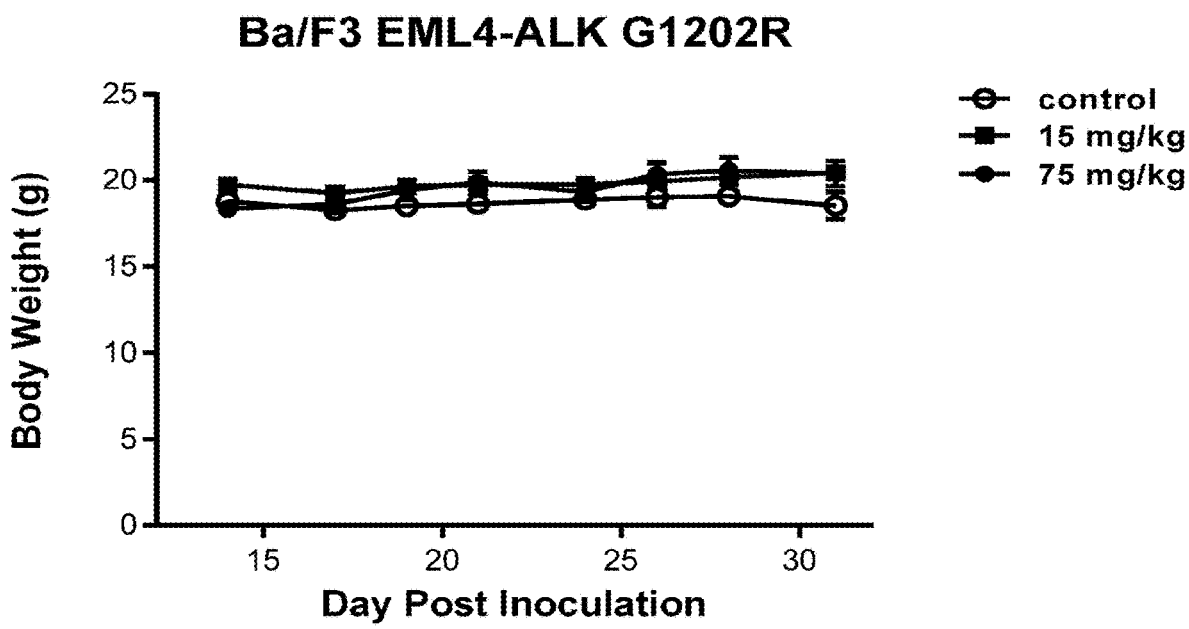
FIG. 18 shows the stability of animal body weight in the Ba/F3 EML4-ALK G1202R in vivo model following administration of Compound 1 at various doses, (○) control, (■) 15 mg/kg, (●) 75 mg/kg.

To investigate the effect of Compound 1 on inhibiting the growth of tumors containing the drug-resistant solvent front mutations, SCID/Beige mice bearing the Ba/F3 EML4-ALK G1202R tumors (at the average tumor size of 210 mm$^3$) were dosed with Compound 1 orally BID for 17 days (FIG. 17). The control group of mice were given vehicle only. Tumor volume was measured by caliper on the indicated days and is shown as mean±sem in FIG. 17. An * denotes that the mean tumor volumes are significantly lower in the treated group compared to that of the control group (p<0.05) as determined by two-way repeated ANOVA followed by post hoc analysis. In this study, treatment of Compound 1 at 75 mg/kg resulted in tumor growth inhibition with a TGI of 99%. 4 of 8 mice exhibited tumor regression in this group. Compound 1 at the dosage of 15 mg/kg demonstrated the ability to inhibit tumor growth at a TGI of 56%. Body weight of the mice were measured on the designated days and no body weight loss was observed in the Compound 1 treatment groups (FIG. 18).

Example 18: Ba/F3 CD74-ROS1 WT Model

Figure 19:
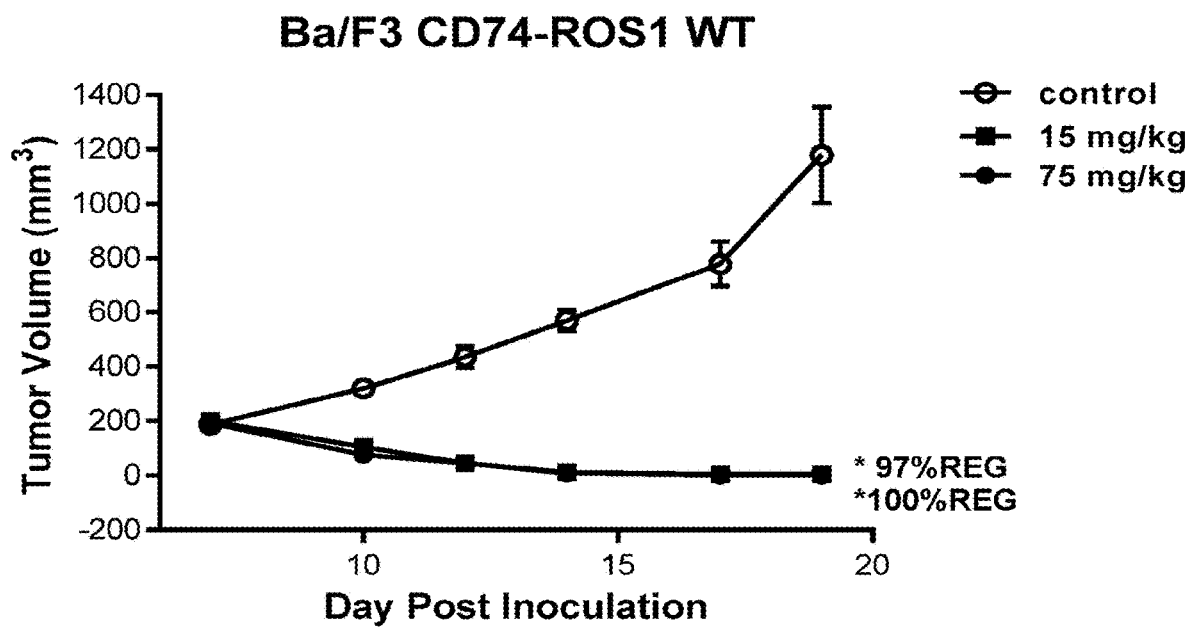
FIG. 19 shows the effect of Compound 1 on tumor growth in the Ba/F3 CD74-ROS1 WT in vivo model at various doses, (○) control, (■) 15 mg/kg, (●) 75 mg/kg.
Figure 20:
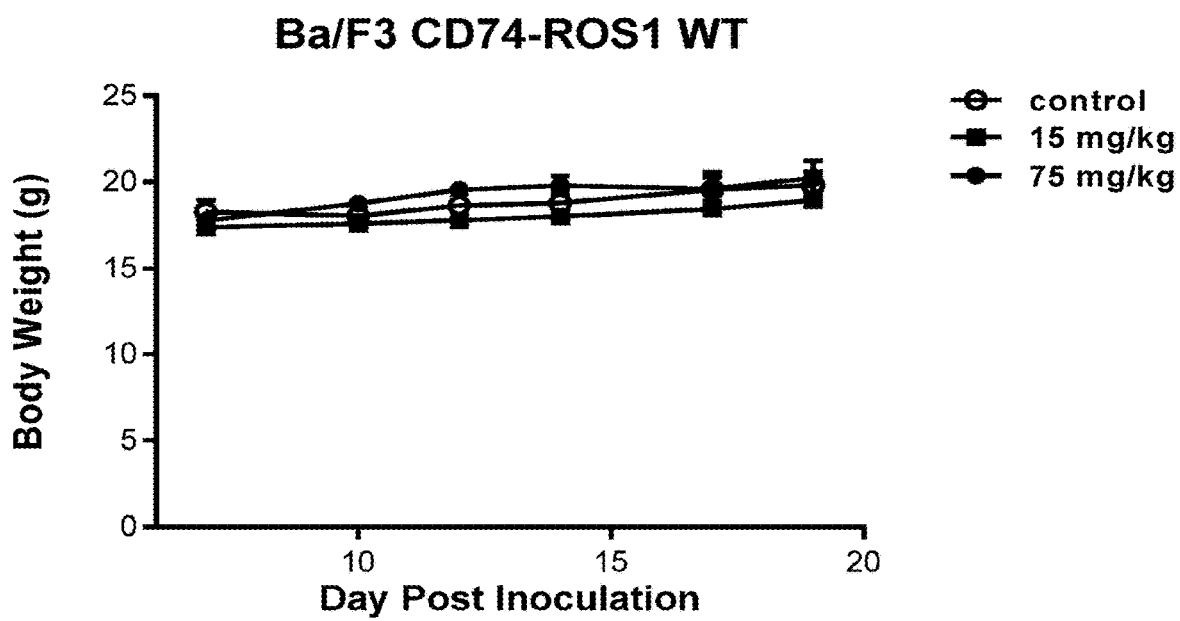
FIG. 20 shows the stability of animal body weight in the Ba/F3 CD74-ROS1 WT in vivo model following administration of Compound 1 at various doses, (○) control, (■) 15 mg/kg, (●) 75 mg/kg.

The CD74-ROS1 fusion gene is considered as one of the drivers for tumor progression in NSCLC. SCID/Beige mice bearing the Ba/F3 CD74-ROS1 WT tumors (at the average tumor size of 200 mm$^3$) were dosed with Compound 1 orally BID for 12 days (FIG. 19). The control group of mice were given vehicle only. Tumor volume was measured by caliper on the indicated days and is shown at mean±sem in FIG. 19. An * denotes that the mean tumor volumes are significantly less in the treated group compared to that of the control group (p<0.05) as determined by two-way repeated ANOVA followed by post hoc analysis. In this study, treatment with Compound 1 at 75 mg/kg resulted in 100% tumor regression, with 8 of 8 mice exhibiting complete tumor regression. Mice in the 15 mg/kg Compound 1 group also demonstrated 97% tumor regression, with 8 of 8 mice in this group exhibiting tumor regression. Body weight of the mice were measured on the designated days and no body weight loss was observed in the Compound 1 treatment groups (FIG. 20).

Example 19: Ba/F3 CD74-ROS1 G2032R Model

Figure 21:
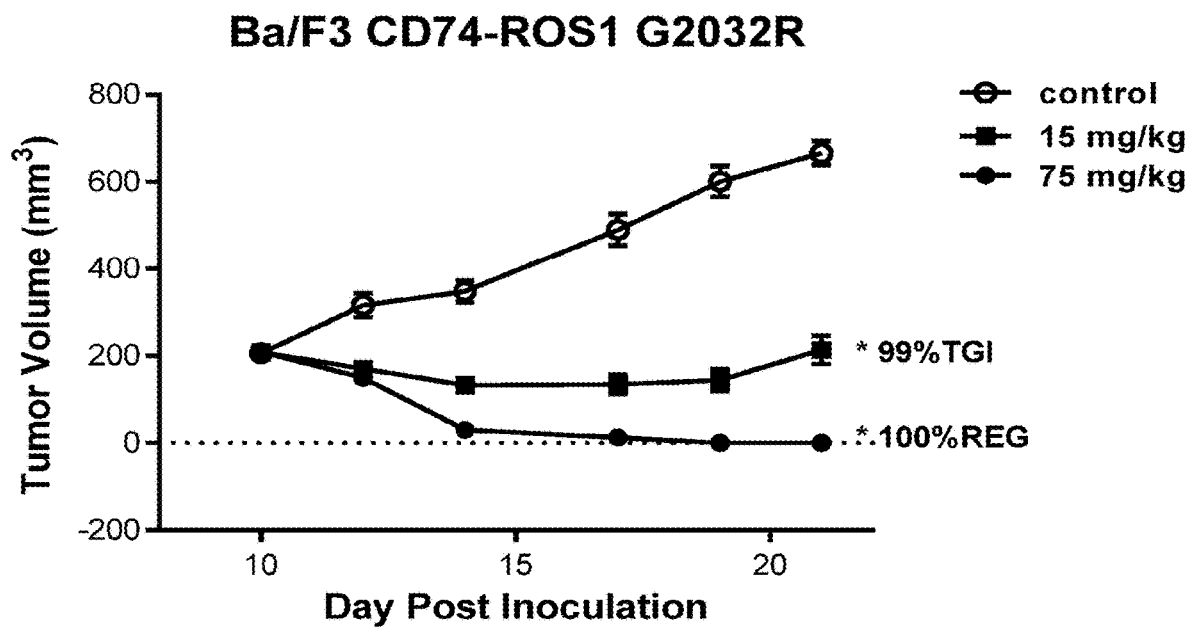
FIG. 21 shows the effect of Compound 1 on tumor growth in the Ba/F3 CD74-ROS1 G2032R in vivo model at various doses, (○) control, (■) 15 mg/kg, (●) 75 mg/kg.
Figure 22:
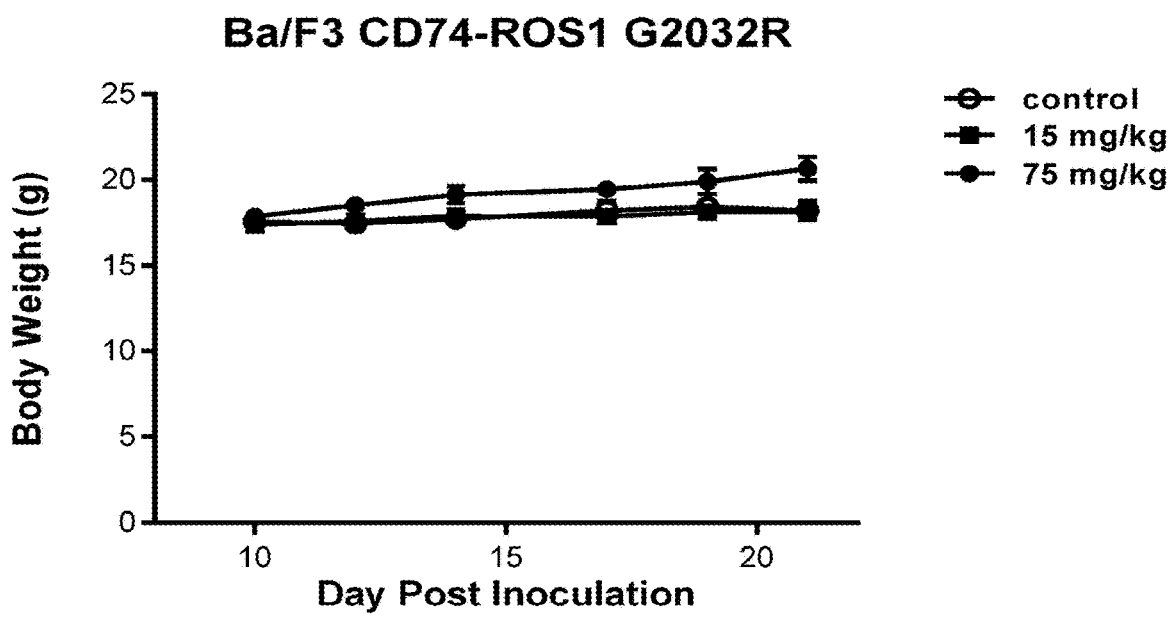
FIG. 22 shows the stability of animal body weight in the Ba/F3 CD74-ROS1 G2032R in vivo model following administration of Compound 1 at various doses, (○) control, (■) 15 mg/kg, (●) 75 mg/kg.

To investigate the effect of Compound 1 on inhibiting the growth of tumors containing the drug-resistant solvent front mutations, SCID/Beige mice bearing the Ba/F3 CD74-ROS1 G2032R tumors (at the average tumor size of 210 mm$^3$) were dosed with Compound 1 orally BID for 11 days (FIG. 21). The control group of mice were given vehicle only. Tumor volume was measured by caliper on the indicated days and is shown at mean±sem in FIG. 21. An * denotes that the mean tumor volumes are significantly less in the treated group compared to that of the control group (p<0.05) as determined by two-way repeated ANOVA followed by post hoc analysis. In this study, treatment with Compound 1 at 75 mg/kg resulted in 100% tumor regression, with 8 of 8 mice exhibiting complete tumor regression. Compound 1 at the dosage of 15 mg/kg/BID demonstrated the ability to inhibit tumor growth at a TGI of 99%, with 2 of 8 mice in this group exhibiting tumor regression. Body weight of the mice were measured on the designated days and no body weight loss was observed in the Compound 1 treatment groups (FIG. 22).

Example 20: NIH3T3 LMNA-TRKA WT Model

Figure 23:
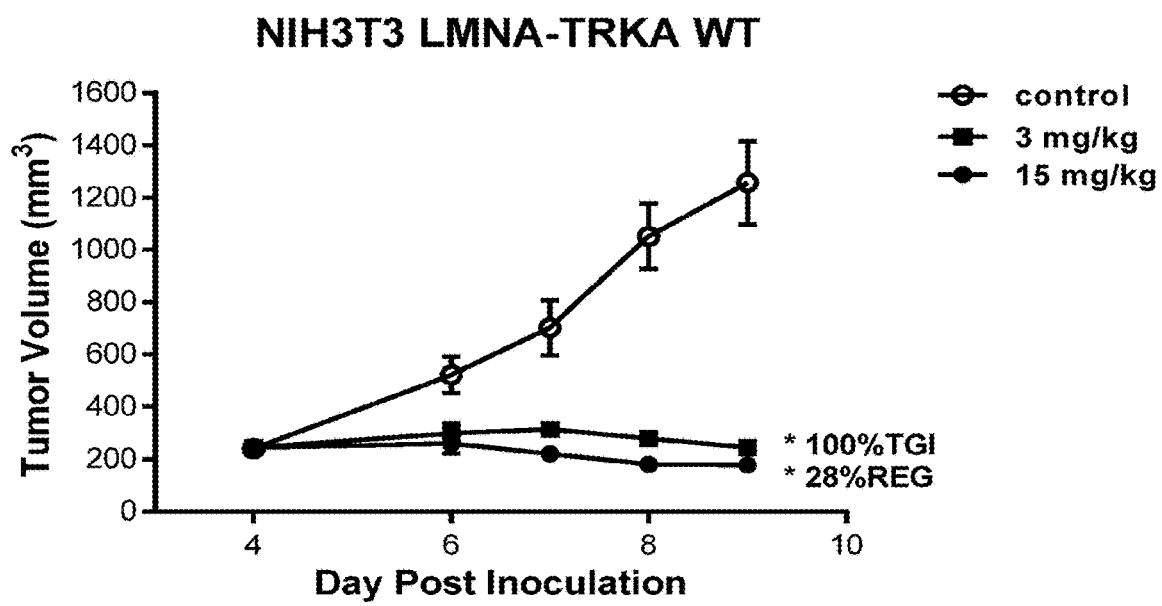
FIG. 23 shows the effect of Compound 1 on tumor growth in the NIH3T3 LMNA-TRKA WT in vivo model at various doses, (○) control, (■) 3 mg/kg, (●) 15 mg/kg.
Figure 24:
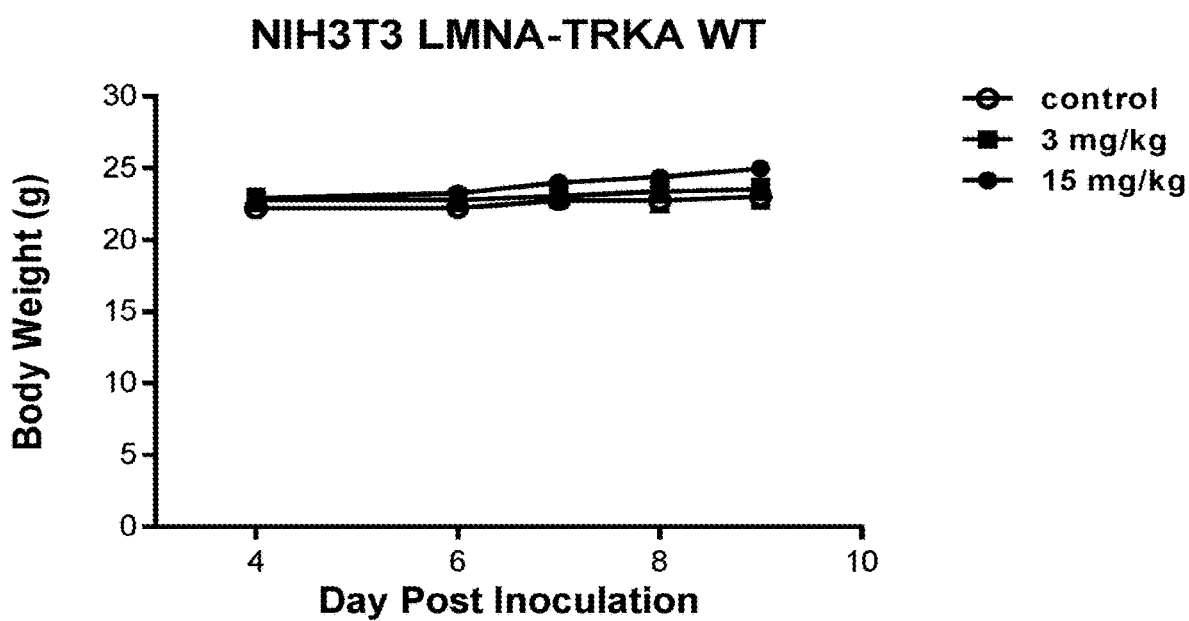
FIG. 24 shows the stability of animal body weight in the NIH3T3 LMNA-TRKA WT in vivo model following administration of Compound 1 at various doses, (○) control, (■) 3 mg/kg, (9) 15 mg/kg.

The LMNA-TRKA fusion gene is considered as one of the drivers for tumor progression in colorectal cancer. Athymic nude mice bearing the NIH3T3 LMNA-TRKA WT tumors (at the average tumor size of 240 mm$^3$) were dosed with Compound 1 orally BID for five days (FIG. 23). Tumor volume was measured by caliper on the indicated days and is shown at mean±sem in FIG. 23. An * denotes that the mean tumor volumes are significantly lower in the treated group compared to that of the control group (p<0.05) as determined by two-way repeated ANOVA followed by post hoc analysis. In this study, treatment with Compound 1 at the dosage of 15 mg/kg resulted in 28% tumor regression, with 7 of 8 mice exhibiting tumor regression. Compound 1 at the dosage of 3 mg/kg demonstrated the ability to inhibit tumor growth at a TGI of 100%, with 3 of 8 mice exhibiting tumor regression. No loss of body weight were observed in mice treated with Compound 1 compared to those with vehicle control (FIG. 24).

Example 21: NIH3T3 LMNA-TRKA G595R Model

Figure 25:
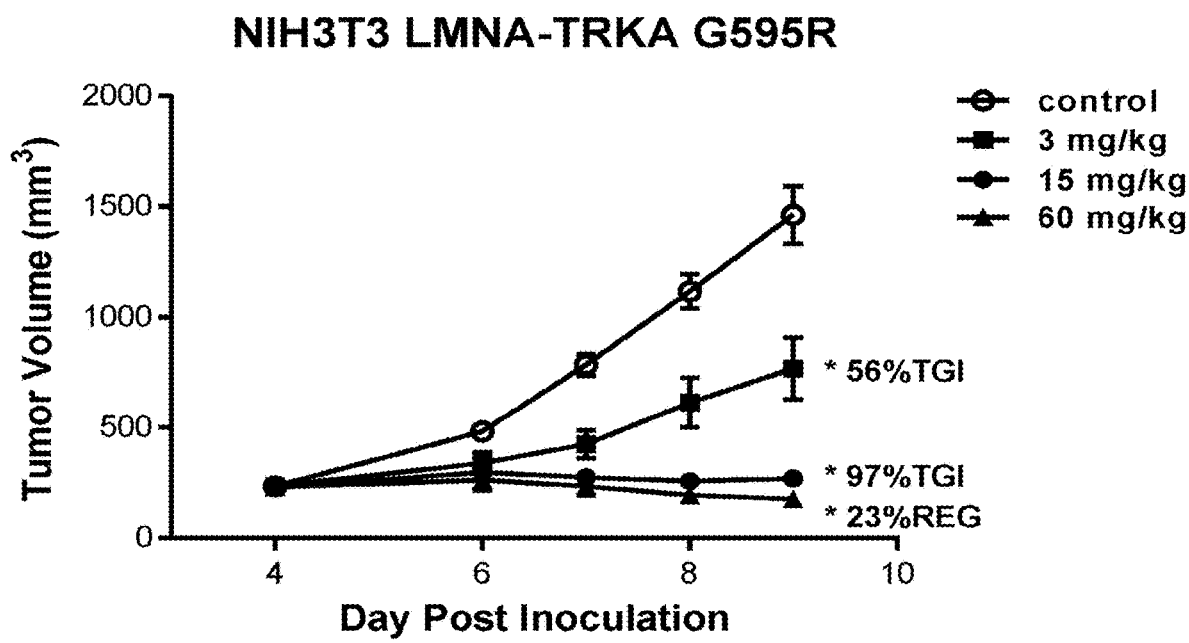
FIG. 25 shows the effect of Compound 1 on tumor growth in the NIH3T3 LMNA-TRKA G595R in vivo model at various doses, (○) control, (■) 3 mg/kg, (●) 15 mg/kg, (▲) 60 mg/kg.
Figure 26:
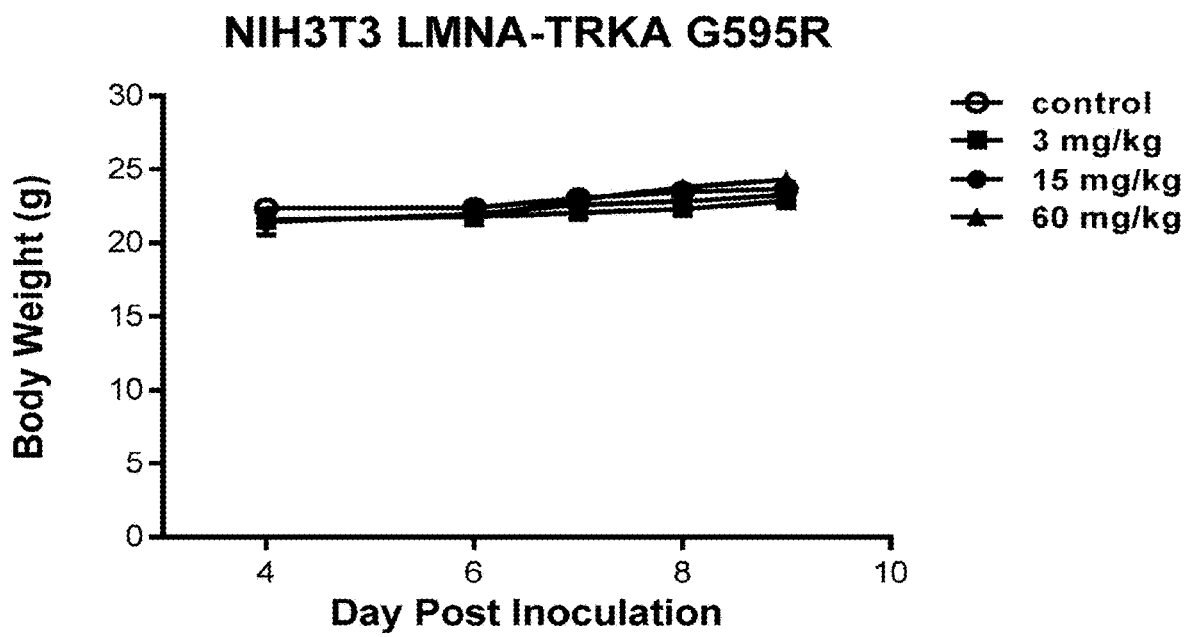
FIG. 26 shows the stability of animal body weight in the NIH3T3 LMNA-TRKA G595R in vivo model following administration of Compound 1 at various doses, (○) control, (■) 3 mg/kg, (●) 15 mg/kg, (▲) 60 mg/kg.

To investigate the effect of Compound 1 on inhibiting the growth of tumors containing the drug-resistant solvent front mutations, athymic nude mice bearing the NIH3T3 LMNA-TRKA G595R tumors (at the average tumor size of 230 mm$^3$) were dosed with Compound 1 orally BID for five days (FIG. 25). The control group of mice were given vehicle only. Tumor volume was measured by caliper on the indicated days and is shown at mean±sem in FIG. 25. An * denotes that the mean tumor volumes are significantly less in the treated group compared to that of the control group (p<0.05) as determined by two-way repeated ANOVA followed by post hoc analysis. In this study, treatment with Compound 1 at 60 mg/kg resulted in 23% tumor regression, with 10 of 10 mice exhibiting tumor regression. Compound 1 at the dosage of 15 mg/kg demonstrated the ability to inhibit tumor growth at a TGI of 97%, with 3 of 8 mice in this group exhibiting tumor regression. Compound 1 at the dosage of 3 mg/kg demonstrated the ability to inhibit tumor growth at a TGI of 56%. Body weight of the mice were measured on the designated days and no body weight loss was observed in the Compound 1 treatment groups (FIG. 26).

What is claimed is:

1. A method of treating a cancer in a patient in need thereof, comprising administering to the patient a therapeutically effective amount of Compound 1:

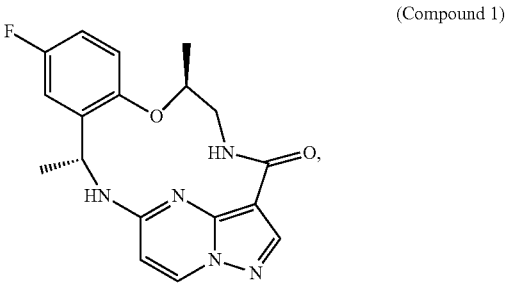 [SMILES: C[C@H]1CNC(=O)c2cnn3ccc(nc23)N[C@H](C)c2cc(F)ccc2O1]

(Compound 1)

wherein the cancer is mediated by a ROS1 kinase.

2. The method of claim 1, wherein the cancer is mediated by a genetically altered ROS1 kinase.

3. The method of claim 1 wherein the cancer is mediated by a fusion protein comprising a fragment of a protein encoded by an ROS1 gene and a fragment of a protein encoded by a gene selected from the group consisting of FIG, TPM3, SDC4, SLC34A2, CD74, EZR, and LRIG3.

4. The method of claim 3, wherein the fusion protein comprises a fragment of a protein encoded by an ROS1 gene and a fragment of a protein encoded by a CD74 gene.

5. The method of claim 2, wherein the genetically altered ROS1 kinase is a CD74-ROS1 fusion protein.

6. The method of claim 5, wherein the CD74-ROS1 fusion protein is a wild-type protein.

7. The method of claim 5, wherein the CD74-ROS1 fusion protein comprises at least one resistance mutation.

8. The method of claim 5, wherein the CD74-ROS1 fusion protein comprises a G2032R, L2026M or D2033N point mutation.

9. The method of claim 2, wherein the genetically altered ROS1 kinase is a SDC4-ROS1 fusion protein.

10. The method of claim 9, wherein the SDC4-ROS1 fusion protein is a wild-type protein.

11. The method of claim 9, wherein the SDC4-ROS1 fusion protein comprises at least one resistance mutation.

12. The method of claim 9, wherein the SDC4-ROS1 fusion protein comprises a G2032R point mutation.

13. The method of claim 2, wherein the genetically altered ROS1 kinase is a SLC34A2-ROS1 fusion protein.

14. The method of claim 13, wherein the SLC34A2-ROS1 fusion protein is a wild-type protein.

15. The method of claim 13, wherein the SLC34A2-ROS1 fusion protein comprises at least one resistance mutation.

16. The method of claim 13, wherein the SLC34A2-ROS1 fusion protein comprises a G2032R point mutation.

17. The method of claim 1, wherein the cancer is selected from the group consisting of glioblastoma, glioblastoma multiforme, non-small cell lung cancer (NSCLC), cholangiocarcinoma, ovarian cancer, gastric adenocarcinoma, colorectal cancer, inflammatory myofibroblastic tumor, angiosarcoma, and epithelioid hemangioendothelioma.

18. The method of claim 1, wherein the cancer is non-small cell lung cancer (NSCLC).

19. The method of claim 1, wherein the patient has been previously treated with a cancer therapeutic.

20. The method of claim 19, wherein the cancer has developed resistance to the cancer therapeutic.

21. The method of claim 1, wherein the therapeutically effective amount of Compound 1 comprises about 250 mg to 1 g daily.

22. The method of claim 1, wherein the therapeutically effective amount of Compound 1 comprises about 50 to 250 mg daily.

23. The method of claim 1, wherein the patient was previously identified as having a cancer mediated by a ROS1 kinase through fluorescence in situ hybridization (FISH), polymerase chain reaction (PCR), or next generation sequencing.

24. The method of claim 1, wherein the administering comprises oral administration.

25. The method of claim 1, comprising administering the therapeutically effective amount of Compound 1 once daily.

26. The method of claim 1, comprising administering the therapeutically effective amount of Compound 1 twice daily.

27. A method of treating a non-small cell lung cancer (NSCLC) in a patient in need thereof, comprising orally administering to the patient a therapeutically effective amount of Compound 1:

(Compound 1)

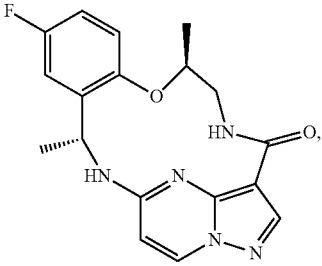

wherein the NSCLC is mediated by a ROS1 kinase.

* * * * *